(12) United States Patent
Horan et al.

(10) Patent No.: US 11,339,436 B2
(45) Date of Patent: May 24, 2022

(54) METHODS FOR EARLY IDENTIFICATION OF BONE HEALING ABILITY IN INJURED PATIENTS

(71) Applicant: The Trustees of the University of Pennsylvania, Philadelphia, PA (US)

(72) Inventors: Annamarie D. Horan, Philadelphia, PA (US); Samir Mehta, Haddonfield, NJ (US); Donald A. Baldwin, Newtown Square, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 716 days.

(21) Appl. No.: 15/548,535

(22) PCT Filed: Feb. 3, 2016

(86) PCT No.: PCT/US2016/016404
§ 371 (c)(1),
(2) Date: Aug. 3, 2017

(87) PCT Pub. No.: WO2016/126844
PCT Pub. Date: Aug. 11, 2016

(65) Prior Publication Data
US 2018/0016638 A1    Jan. 18, 2018

Related U.S. Application Data

(60) Provisional application No. 62/283,443, filed on Sep. 1, 2015, provisional application No. 62/231,935, filed on Feb. 3, 2015.

(51) Int. Cl.
*C12Q 1/6883* (2018.01)
*G01N 33/68* (2006.01)

(52) U.S. Cl.
CPC .......... *C12Q 1/6883* (2013.01); *G01N 33/68* (2013.01); *G01N 33/6887* (2013.01); *G01N 33/6893* (2013.01); *C12Q 2600/106* (2013.01); *C12Q 2600/158* (2013.01); *C12Q 2600/178* (2013.01); *G01N 2570/00* (2013.01); *G01N 2800/10* (2013.01)

(58) Field of Classification Search
CPC .............. G01N 33/68; G01N 33/6887; G01N 33/6893; G01N 2570/00; G01N 2800/10; C12Q 1/6883; C12Q 2600/106; C12Q 2600/158; C12Q 2600/178
See application file for complete search history.

(56) References Cited

U.S. PATENT DOCUMENTS

| 2011/0033516 A1 | 2/2011 | Markwald et al. |
| 2012/0213837 A1 | 8/2012 | Botchwey et al. |
| 2014/0100137 A1 | 4/2014 | Gangji et al. |

FOREIGN PATENT DOCUMENTS

| WO | 2008134054 A1 | 11/2008 |
| WO | 2014201516 A2 | 12/2014 |

OTHER PUBLICATIONS

Affymetrix, Affymetrix GeneChip Gene ST Array Package Insert, published online 2012. pp. 1-2. (Year: 2012).*
Extended European Search Report and Written Opinion for European Patent Application No. 16747207.5 dated Sep. 26, 2018.
Partial European Search Report for European Patent Application No. 16747207.5 dated Jun. 25, 2018.
Ajal, et al. Evaluation of Serum Alkaline Phosphatase as Biomarker of Healing Process Progression of Simple Diaphyseal Fractures in Adult Patients, International Research Journal of Biological Sciences 2(2) ,2013 ,40-43.
Pountos, et al., Fracture non-union: Can biomarkers predict outcome?, Injury 44(12) ,2013 ,1725-1732.
PCT International Search Report and Written Opinion for PCT International Application No. PCT/US2016/016404 dated Jun. 23, 2016.
Panteli, et al., "Biological and molecular profile of fracture non-union tissue: current insights", J Cell Mol Med. 19(4), 2015, 685-713.
Stewart, et al., "Pre-clinical evaluation of therapies to prevent or treat bone non-union: a systematic review protocol", Syst Rev. 4, 2015, 161.

* cited by examiner

*Primary Examiner* — Antonio Galisteo Gonzalez
*Assistant Examiner* — Khaleda B Hasan
(74) *Attorney, Agent, or Firm* — Saul Ewing Arnstein & Lehr LLP; Alireza Behrooz

(57) ABSTRACT

The present invention relates to the discovery that the expression levels of some RNA molecules, comprising messenger RNA (mRNA), non-coding RNA (ncRNA) and/or microRNA (miRNA), and protein can be used as a diagnostic signature to predict or monitor the bone healing ability in an acutely injured subject or in a chronic nonunion subject. In certain embodiments, the invention relates to methods and compositions useful for differentiating between a nonunion, slow healing, and/or normal healing of a fractured bone and treatment recommendations. The invention further includes a kit comprising biomarker probes for assessing the bone healing ability in an acutely injured subject or in a nonunion subject after receiving therapeutic treatment.

13 Claims, 30 Drawing Sheets
Specification includes a Sequence Listing.

Fig. 1

| RNA | SEQ ID | Time period: 1a | | | Time period: 2 | | | | Time period: 3 | | | Time period: 4 | | | Time period: 6 | | | Time period: 7 | | |
|---|---|---|---|---|---|---|---|---|---|---|---|---|---|---|---|---|---|---|---|---|
| | | Atxnorm | Atslow | Atnu | Atxnorm | Atslow | Atxnorm | Atslow | Atnu | Atxnorm | Atslow | Atnu | Atxnorm | Atslow | Atxnorm | Atslow | Atnu | Atxnorm | Atslow | Atnu |
| ANXA3 | 349 | 74 | 84 | 1,533 | -60 | -56 | | | | | | | -91 | -582 | 10,106 | 197,282 | | | | -3,453 |
| HIF8 | 194 | 58 | 31 | | | | | | | | | | -1,030 | -5,232 | 2.7 | 3.4 | | -277 | -6,145 | |
| LDHB | 125 | 24 | 31 | | | | | | | | | | -5,823 | -21,395 | | | | -1,271 | -2.9 | -4.0 |
| S100A13 | 5,618 | 6.9 | 6.7 | | | | | | | | | | -3.1 | -4.2 | | | | -2.7 | | |
| RPS27 | 347 | 1.8 | | 2.8 | 1.8 | 2.0 | | | | | | | | | | | | | | |
| CLIC2 | 512 | 1.7 | | 3.5 | 1.7 | 1.8 | | | | | | | | | | | | | | |
| SNORA19 | 78 | 1.4 | 1.5 | | | | | | | | | | | | | | | 1.8 | -1.7 | -2.0 |
| C3T7 | 293 | -1.5 | -1.5 | | | | | | | | | | | | | 1.9 | | -2.0 | -2.0 | -1.9 |
| PECAM1 | 1838 | | | | 1.6 | | | | | | | | | | 2.0 | | 2.2 | | | |
| IFIT1B | 64,654 | | | | 2.2 | 2.2 | | | | | | | | | | | | | | |
| HMR8 | 89,677 | | | | 1.6 | 1.8 | | | | | | | | | 2.1 | | | | | 3.0 |
| PFDPF | 291 | | | | 1.7 | 1.7 | | | | | | | | | 2.1 | | | | | |
| RAD23A | 239 | | | | 1.5 | 1.6 | | | | | | | | | | | | 2.2 | | |
| AIF1 | 1,515,408,512 | | | | 1.4 | 1.5 | | | | | | | | | 2.0 | | | 1.4 | | |
| RPS15 | 279 | | | | 1.4 | 1.5 | 1.4 | 1.4 | 2.0 | | 1.5 | | | | 1.8 | | | | | |
| NEUFA2 | 401 | | | | 1.3 | | 1.7 | 1.7 | | | | | | | | | | | | |
| TSTA3 | 471 | | | | | 1.8 | | | | | | | | | | | | | | |
| ANKRO22 | 75 | | | | | | | | | | | | -4.9 | -8.0 | | | | | | |
| TRMN | 7,30,497 | | | | | | 1.5 | 1.4 | 2.4 | | | | | | 2.3 | 2.0 | 3.2 | | | |
| MXD3 | 279 | | | | | | 1.4 | 1.5 | | | | | | | 1.6 | | | | | |
| RPRD1B | 293 | | | | | | 1.3 | | 1.8 | | | | | | | | | | | |
| SNORD34E | 104 | | | | | | 1.3 | 1.2 | | | | | | | | -1.3 | | | | |
| HSPD1 | 283 | | | | | | 1.2 | | | | | | | | | | | | | |
| RPL36A | 442 | | | | | | 1.2 | 1.2 | | | | | | | | | | | | |
| EIF4B | 132 | | | | | | | | 1.5 | | | | | | | | | | | |
| miR-25a stem-loop | 449 | | | | | | | | | | | | 5.7 | | | | | | | |
| IL2RB | 2 | | | | | | | | | | | | 1.3 | 1.4 | | | | 1.7 | 1.7 | 1.7 |
| MT1X | 191 | | | | | | | | | | | | -1.7 | -1.8 | | | | -2.0 | -2.4 | |
| HSPA9 | 400 | | | | | | | | | | | | | | -1.7 | -1.9 | | | | |
| ARG1 | 413 | | | | | | | | | | | | | | | 2.5 | | | | |
| CLEC4D | 109,702 | | | | | | | | | | | | | | | 2.8 | | | 6.9 | |
| FAM83A | 459 | | | | | | | | | | | | | | | | | 1.5 | | 1.3 |
| NFATC2 | 4 | | | | | | | | | | | | | | -1.6 | -1.6 | | -1.3 | -1.3 | -1.3 |
| SNORD13 | 228 | | | | | | | | | | | | | | -1.5 | -1.5 | | -1.3 | | |
| SNORD25 | 6 | | | | | | | | | | | | | | | | | | -433 | |

Fig. 2

| Within subject mRNA expression change | | | | | Average fold change | |
|---|---|---|---|---|---|---|
| from time | to time | RNA | SEQ ID | p-value | AInorm | AIslow |
| 1a | 1b | ARPP19 | 388 | 0.001 | nc | 21 |
| 1a | 1b | TRNN | 7, 30, 497 | 0.001 | nc | -11 |
| 1a | 1b | RPS15 | 279 | 0.002 | nc | -14 |
| 1a | 1b | SNORD59B | 134 | 0.003 | nc | -6.2 |
| 1a | 1b | MXD3 | 270 | 0.005 | nc | -4.1 |
| 1a | 1b | NFATC2 | 4 | 0.005 | nc | -2.3 |
| 1a | 1b | PPDPF | 291 | 0.005 | 1.6 | -4.0 |
| 1a | 1b | RPS27 | 347 | 0.006 | nc | -9.9 |
| 1a | 1b | CST7 | 290 | 0.01 | -1.6 | -4.3 |
| 1a | 1b | MT1E | 189 | 0.01 | nc | 23 |
| 1a | 1b | EIF4B | 132 | 0.01 | nc | 2.3 |
| 1a | 1b | IL2RB | 2 | 0.01 | nc | -3.0 |
| 1a | 1b | TLR5 | 53 | 0.01 | -2.7 | nc |
| 1a | 1b | MT1X | 191 | 0.02 | nc | 1.8 |
| 1a | 1b | RAD23A | 239 | 0.02 | nc | -5.2 |
| 1a | 1b | NDUFA2 | 401 | 0.02 | nc | -3.0 |
| 1a | 1b | ANKRD22 | 75 | 0.02 | -1.7 | 2.7 |
| 1a | 1b | IRF8 | 194 | 0.02 | -80.0 | 751 |
| 1a | 1b | TSTA3 | 471 | 0.03 | nc | -5.3 |
| 1a | 1b | RPL36A | 442 | 0.03 | nc | 11 |
| 1a | 1b | AIF1 | 1, 408, 513, 515 | 0.04 | -1.6 | -3.8 |
| 1a | 1b | PECAM1 | 1838 | 0.05 | -1.5 | nc |
| 1a | 2 | IRF8 | 194 | 0.04 | 5.7 | -123 |
| 1b | 2 | IRF8 | 194 | 0.03 | 18.7 | -1,513 |
| 1b | 2 | ANXA3 | 349 | 0.03 | 5.1 | -4,220 |
| 1a | 4 | IL2RB* | 2 | 0.02 | nc | 2.0 |
| 1a | 4 | LDHB | 126 | 0.04 | 39.0 | -4,339 |
| 1a | 4 | ANXA3 | 349 | 0.05 | 81.7 | -5,204 |
| 1a | 4 | PECAM1 | 1838 | 0.05 | 1.7 | -1.7 |
| 2 | 3 | MXD3 | 270 | 0.05 | -1.7 | nc |
| 2 | 4 | SNORA19 | 78 | 0.001 | 1.5 | -1.7 |
| 2 | 4 | CLEC4D | 109, 702 | 0.01 | nc | -2.6 |
| 2 | 4 | HMBS | 89, 677 | 0.03 | nc | -1.5 |
| 2 | 4 | ANKRD22 | 75 | 0.03 | 1.5 | -7.1 |
| 2 | 4 | TLR5 | 53 | 0.04 | nc | -2.0 |
| 2 | 4 | CLIC2 | 512 | 0.04 | nc | -2.2 |
| 2 | 4 | ARPP19 | 388 | 0.04 | nc | -1.5 |

Fig. 3

| Within subject miRNA expression change | | | | Average fold change | | | p-value | | |
|---|---|---|---|---|---|---|---|---|---|
| from time | to time | microRNA | SEQ ID | AInorm | AIslow | AInu | AIslow vs. AInorm | AInu vs. AInorm | AInu vs. AIslow |
| week 1 | weeks 2+3 | hsa-let-7f-5p | 518 | -3.1 | -2,353 | 49 | 0.10 | 0.27 | 0.04 |
| week 1 | weeks 2+3 | hsa-miR-551a | 549 | -2.4 | nc | 202 | 0.76 | 0.05 | 0.15 |
| week 1 | weeks 2+3 | hsa-miR-664a-5p | 552 | nc | nc | 365 | 0.78 | 0.002 | 0.01 |
| week 1 | weeks 2+3 | hsa-miR-199a-5p | 531 | nc | 2.4 | 433 | 0.70 | 0.01 | 0.05 |
| week 1 | weeks 2+3 | hsa-miR-1270 | 523 | 1.6 | 2.2 | 1,046 | 0.84 | 0.006 | 0.025 |
| 1a | 1b | hsa-let-7f-5p | 518 | -4.5 | -6,041 | 49 | 0.04 | 0.26 | 0.02 |
| 1a | 1b | hsa-miR-664a-5p | 552 | nc | 12 | 365 | 0.20 | 0.04 | 0.27 |
| 1a | 2 | hsa-miR-182-3p | 528 | -2 | -3 | 1,149 | 0.77 | 0.006 | 0.006 |
| 1a | 2 | hsa-let-7f-5p | 518 | 8.3 | -3.9 | 833,140 | 0.27 | 0.07 | 0.03 |
| 1b | 2 | hsa-miR-182-3p | 528 | nc | 2 | 3,423 | 0.57 | 0.001 | 0.003 |
| 1a+1b | 2 | hsa-miR-1270 | 523 | nc | 5.8 | nc | 0.05 | 0.95 | 0.37 |
| 1a+1b | 2 | hsa-miR-182-3p | 528 | nc | -3.1 | 2,593 | 0.34 | 0.004 | 0.002 |
| 1a | 3 | hsa-miR-1228-5p | 520 | -18 | 162 | 191 | 0.002 | 0.08 | 0.97 |
| 1a | 3 | hsa-miR-504-5p | 548 | -1.9 | -2.4 | 4,921 | 0.69 | 3.6E-06 | 3.2E-06 |
| 1a | 3 | hsa-miR-551a | 549 | -9.2 | 1.5 | 13,887 | 0.36 | 0.05 | 0.13 |
| 1a | 3 | hsa-miR-664a-5p | 552 | 2.1 | nc | 15,641 | 0.75 | 0.07 | 0.05 |
| 1a | 3 | hsa-miR-199a-5p | 531 | -2.6 | nc | 19,241 | 0.41 | 0.0001 | 0.0002 |
| 1a | 3 | hsa-miR-1270 | 523 | nc | 2.5 | 114,295 | 0.05 | 3.7E-09 | 1.3E-08 |
| 1a+1b | 3 | hsa-miR-182-3p | 528 | nc | -2.7 | -21,587 | 0.59 | 0.02 | 0.04 |
| 1a+1b | 3 | hsa-miR-18a-5p | 529, 1520 | nc | nc | -51 | 0.77 | 0.04 | 0.05 |
| 1a+1b | 3 | hsa-miR-93-5p | 556 | nc | nc | -32 | 0.95 | 0.05 | 0.05 |
| 1a+1b | 3 | hsa-miR-221-3p | 533 | nc | nc | -27 | 0.95 | 0.03 | 0.03 |
| 1a+1b | 3 | hsa-miR-1270 | 523 | nc | 2.3 | -19 | 0.07 | 0.01 | 0.002 |
| 1a+1b | 3 | hsa-miR-589-5p | 551 | nc | nc | -15 | 0.38 | 0.02 | 0.01 |
| 1a+1b | 3 | hsa-miR-584-5p | 550 | nc | 2.5 | -12 | 0.11 | 0.18 | 0.05 |
| 1a+1b | 3 | hsa-miR-1255b-5p | 522 | nc | 2.2 | -9.3 | 0.03 | 0.03 | 0.003 |
| 2 | 3 | hsa-miR-584-5p | 550 | -1.8 | nc | no data | 0.03 | | |
| 2 | 4 | hsa-miR-551a | 549 | -110 | 4.5 | 114 | 0.07 | 0.047 | 0.48 |

Fig. 4

| SEQ ID | miRNA group | AInorm | AIslow | all AI | HV | p-value |
|---|---|---|---|---|---|---|
| 528 | miR-182-3p samples | | | 22% | 0% | 0.29 |
| | miR-182-3p subjects | | | 51% | 0% | 0.016 |
| 520 | miR-1228-5p samples | 29% | 51% | | | 0.0014 |
| | miR-1228-5p subjects | 50% | 73% | | | 0.049 |
| 518 | let-7f-5p samples | 45% | 32% | | | 0.046 |
| | let-7f-5p subjects | | | 67% | 13% | 0.0076 |

Fig. 5

| | | Time period: month 1 | | month 2 | |
|---|---|---|---|---|---|
| SEQ ID | RNA | fold difference | p-value | fold difference | p-value |
| 371 | ROPN1L | 2.6 | 0.003 | | |
| 344 | S100P | 5.7 | 0.009 | | |
| 4 | NFATC2 | -1.9 | 0.018 | | |
| 126 | LDHB | | | 30.2 | 0.018 |
| 349 | ANXA3 | 387,525 | 0.020 | 4,468,533 | 0.054 |
| 2 | IL2RB | -1.8 | 0.023 | | |
| 1838 | PECAM1 | 1.6 | 0.024 | 2.3 | 0.003 |
| 388 | ARPP19 | 1.5 | 0.036 | | |
| 413 | ARG1 | 2.9 | 0.045 | | |
| 109, 702 | CLEC4D | 2.2 | 0.048 | | |
| 75 | ANKRD22 | 14.7 | 0.052 | | |
| 53 | TLR5 | 2.0 | 0.052 | | |
| 528 | hsa-miR-182-3p* | 4,233 (p 0.012) | | | |

* data pooled for months 1 and 2

Fig. 6

| SEQ ID | Protein | Time period: 1a AIslow | 1a AInu | 3 and 4 AInu | Name |
|---|---|---|---|---|---|
| 1778, 1779 | CXCL3 CXCL2 | 2.8 | | | Gro-beta/gamma |
| 1787 | CXCL6 | 2 | | | C-X-C motif chemokine 6 |
| 1699 | VWF | 2 | | | von Willebrand factor |
| 1715, 1716, 1717, 1826, 1827 | BDNF | 1.8 | 1.5 | | Brain-derived neurotrophic factor |
| 1803 | HSPA8 | 1.7 | | | Heat shock cognate 71 kDa protein |
| 1740, 1741, 1781 | LEPR | 1.7 | | | Leptin receptor |
| 1701 | IFNA2 | 1.6 | | | Interferon alpha-2 |
| 1750, 1821, 1822 | CASP2 | 1.4 | | | Caspase-2 |
| 1789 | TIMP1 | 1.3 | 1.4 | | Metalloproteinase inhibitor 1 |
| 1773, 1757 | CPB2 | 1.3 | | | Carboxypeptidase B2 |
| 1825 | ESAM | 1.2 | | | Endothelial cell-selective adhesion molecule |
| 1783 | NGF | 1.2 | 1.2 | -1.7 | beta-nerve growth factor |
| 1705, 1761, 1762 | FAM107A | -1.1 | | | protein FAM107A |
| 1777 | GAS1 | -1.2 | | | Growth arrest-specific protein 1 |
| 1793 | GZMB | -1.2 | | | Granzyme B |
| 1751, 1784 | PDE7A | -1.2 | | | High affinity cAMP-specific 3',5'-cyclic phosphodiesterase 7A |
| 1804 | LYVE1 | -1.2 | 1.3 | | Lymphatic vessel endothelial hyaluronic acid receptor 1 |
| 1809 | IL20 | -1.2 | | | Interleukin-20 |
| 1713, 1788 | TGFB2 | -1.2 | | | Transforming growht factor beta-2 |
| 1691 | APOA1 | -1.3 | -1.2 | | Apolipoprotein A-I |
| 1796 | GPC5 | -1.6 | 1.5 | | Glypican-5 |
| 1695, 1711, 1730 | CTSA | -1.6 | | | Lysosomal protective protein |
| 1698, 1703, 1753, 1756 | CGA TSHB | -2.2 | -2.4 | | Thyroid stimulating hormone |
| 1794 | PYY | -2.2 | | | Peptide YY |
| 1774 | CST5 | | 2.5 | | Cystatin-D |
| 1812 | FGF23 | | 1.6 | | Fibroblast growth factor 23 |
| 1810, 1736 | RETN | | 1.5 | | Resistin |
| 1780 | ICAM3 | | 1.3 | | Intercellular adhesion molecule 3 |
| 1776 | FGF4 | | -1.2 | | Fibroblast growth factor 4 |
| 1801, 1755 | PTK6 | | -1.2 | | Protein-tyrosine kinase 6 |
| 1724, 1733, 1759, 1692, 1758, 1760 | C2 | | -1.4 | | Complement C2 |
| 1732 | LDHB | | -1.5 | | L-lactate dehydrogenase B chain |
| 1798 | PGLYRP1 | | -1.8 | | Peptidoglycan recognition protein 1 |
| 1705, 1706, 1707, 1714, 1735, 1791, 1816 | FCGR2A FCGR2B | | | 3.3 | Low affinity immunoglobulin gamma Fc region receptor II-a/b |
| 1702, 1742, 1743, 1744 | ACY1 | | | 2.2 | Aminoacylase-1 |
| 1708, 1734, 1763, 1764, 1829 | CAST | | | 2 | Calpastatin |
| 1820 | CCL15 | | | 2 | C-C motif chemokine 15 |
| 1797 | OMD | | | 1.8 | Osteomodulin |

Fig. 7A

| SEQ ID | Protein | Time period: 1a | | 3 and 4 | Name |
|---|---|---|---|---|---|
| | | Alslow | Alnu | Alnu | |
| 1696 | TGFBI | | | 1.6 | Transforming growth factor-beta-induced protein ig-h3 |
| 1697 | AMH | | | 1.5 | Muellerian-inhibiting factor |
| 1700 | TNF | | | 1.4 | Tumor necrosis factor |
| 1807, 1754, 1710 | GP6 | | | 1.4 | Platelet glycoprotein VI |
| 1799 | EPHA1 | | | 1.4 | Ephrin type-A receptor 1 |
| 1792 | FCN2 | | | 1.3 | Ficolin-2 |
| 1824 | TNFRSF13C | | | 1.3 | Tumor necrosis factor receptor superfamily member 13C |
| 1818, 1693, 1726 | FGFR3 | | | 1.3 | Fibroblast growth factor receptor 3 |
| 1785 | DMP1 | | | 1.3 | Dentin matrix acidic phosphoprotein 1 |
| 1745, 1746, 1749, 1747, 1748, 1704 | PRLR | | | 1.2 | Prolactin receptor |
| 1813, 1729 | SPINT2 | | | 1.2 | Kunitz-type protease inhibitor 2 |
| 1738, 1805, 1786, 1739 | PRSS3 | | | 1.2 | Trypsin-3 |
| 1800, 1826, 1765, 1766 | IL12RB1 | | | 1.2 | Interleukin-12 receptor subunit beta-1 |
| 1772 | C1S | | | 1.1 | Complement C1s subcomponent |
| 1819 | SLC25A18 | | | 1.1 | Mitochondrial glutamate carrier 2 |
| 1767, 1790 | TNFRSF14 | | | 1.1 | Tumor necrosis factor receptor superfamily member 14 |
| 1802 | FGF8 | | | 1.1 | Fibroblast growth factor 8 |
| 1808 | IL1RAPL2 | | | 1.1 | X-linked interleukin-1 receptor accessory protein-like 2 |
| 1817, 1770 | LIN7B | | | -1.1 | Protein lin-7 homolog B |
| 1685, 1686, 1687, 1688, 1689, 1690 | IGHG1 IGHG2 IGHG3 IGHG4 IGK IGL | | | -1.3 | Immunoglobulin G |
| 1815 | NTN4 | | | -1.3 | Netrin-4 |
| 1731, 1694 | PLG | | | -1.3 | Angiostatin |
| 1811, 1728, 1727 | AMHR2 | | | -1.4 | Anti-Muellerian hormone type-2 receptor |
| 1712, 1806, 1752 | SPOCK2 | | | -1.5 | Testican-2 |
| 1775 | DSG2 | | | -1.5 | Desmoglein-2 |
| 1718, 1719, 1720, 1721, 1722, 1723, 1814 | CD209 | | | -1.5 | CD209 antigen |
| 1823 | FCRL3 | | | -1.5 | Fc receptor-like protein 3 |
| 1785, 1768, 1769 | PGD | | | -2.4 | 6-phosphogluconate dehydrogenase, decarboxylating |
| | | Time 1a to 2, 3 or 4 | | | |
| | | Alnorm | Alslow | Alnu | |
| 1732 | LDHB | -0.56 | 0.31 | 0.53 | L-lactate dehydrogenase B chain |
| 1783 | NGF | 0.14 | -0.1 | -0.21 | beta-nerve growth factor |
| 1796 | GPC5 | 0.07 | 0.13 | -0.18 | Glypican-5 |
| 1804 | LYVE1 | -0.12 | -0.08 | 0.52 | Lymphatic vessel endothelial hyaluronic acid receptor 1 |

Fig. 7B

| Outcome | Subjects | Paxgene blood RNA samples | | | | | |
|---|---|---|---|---|---|---|---|
| | | Time A | B | C | D | E | Total |
| AInorm | 62 | 58 | 24 | 34 | 27 | 36 | 179 |
| AInu | 8 | 6 | 3 | 3 | 4 | 21 | 37 |
| AIslow | 19 | 19 | 4 | 14 | 11 | 24 | 72 |
| AI Total | 89 | 83 | 31 | 51 | 42 | 81 | 288 |
| NUhealed | 5 | 6 | 1 | 5 | 3 | 6 | 21 |
| NUslow | 5 | 6 | 0 | 4 | 5 | 16 | 31 |
| NU Total | 10 | 12 | 1 | 9 | 8 | 22 | 52 |

Fig. 8

| Fig. 9 row | RNA | SEQ ID | log2 A/nu/A/norm | | | | log2 A/slow/A/norm | | | | log2 A/notnorm/A/norm | | | |
|---|---|---|---|---|---|---|---|---|---|---|---|---|---|---|
| | | | A | B | C | D | A | B | C | D | A | B | C | D |
| 1 | A2M | 722 | | | | | | | | | | -1.43 | | |
| 2 | A2M-AS1 | 703 | | | | | | | 1.58 | | | | | |
| 3 | A2MP1 | 724 | | | | | | | | | | | | |
| 4 | ADGRE1 | 966 | | | -1.74 | -66.02 | | | | | | | -1.51 | -28.7 |
| 5 | AIF1 | 1,498, 513, 515 | | | | | -1.51 | | | | | | | |
| 6 | ANKRD22 | 75 | | | -2.21 | | | 3.44 | -4.81 | | | 2.22 | -1.68 | |
| 7 | ANKRD36B | 1074 | | | | -278.42 | 1.57 | | 1.21 | 2.25 | 1.46 | | | -140 |
| 8 | ANPEP | 862 | | | | | 1.47 | | 2.08 | | 1.51 | | | 1.7 |
| 9 | ANXA3 | 349 | | | | | -1.7 | | -2.17 | | | | | |
| 10 | ARG1 | 413 | | | | | -2.38 | | | | | | | |
| 11 | ARPP19 | 388 | | | | | | | 1.54 | | | | | |
| 12 | ATG9A | 1080 | | | | | -1.44 | -1.62 | | | -1.51 | | | |
| 13 | C4BPA | 598 | | | -3.58 | -15800 | | | | | | | | -7970 |
| 14 | CASP5 | 193, 698 | | | -1.92 | | | | -1.87 | | | | -1.83 | |
| 15 | CCDC144A | 910, 911 | | | | | | | | | | | | |
| 16 | CCR7 | 934 | | | | | | | 2.06 | | | | | |
| 17 | CD27 | 700 | | | | | | | | | | | | |
| 18 | CES1 | 885 | 3.53 | | | | 2.25 | | 3.18 | | 2.47 | | | |
| 19 | CHRM3-AS2 | 634 | | | | -1.49E+10 | | | 1.87 | | | | | -7.44E+09 |
| 20 | CLEC1B | 124, 725 | | | -2.06 | -2.13E+08 | | | 2 | | | | | -1.07E+08 |
| 21 | CLEC4D | 109, 702 | | | | | -2.04 | 3.05 | | | | | | |
| 22 | CLEC4E | 721 | | | | | | | | | | | | |
| 23 | CLIC2 | 512 | | | | | -2.04 | | | | -2.23 | | | |
| 24 | CLU | 1382 | | -1.95 | -2.34 | | | | | 1.85 | 1.38 | | -1.78 | 1.7 |
| 25 | CMTM2 | 889 | | | | -6060 | -2.25 | | -3.18 | | -2.05 | -2.06 | -2.87 | -3030 |
| 26 | COX7B | 1431 | | | | | | | | | | | | |
| 27 | CR1 | 24, 599 | | | | | | | | 1.74 | 1.62 | | | 1.55 |
| 28 | CSNK1A1L | 753 | | | | -1046 | | | | | | | | -521 |
| 29 | CST7 | 280 | | | | | | 2.79 | 1.52 | | 1.53 | 1.85 | | |
| 30 | DSC2 | 952 | | | | -716 | 1.7 | | 4.82 | | 1.61 | | | -358 |
| 31 | DYSF | 1024 | | | | | -1.47 | -1.66 | | | | | | |
| 32 | EGF | 351, 1180 | | | -2.52 | 2.41 | | | 2.02 | | | | -1.97 | |
| 33 | EIF4B | 132 | | | | | -1.4 | -1.25 | | | | | | |
| 34 | F5 | 45, 624 | 2.38 | | | | | | 2.05 | 1.67 | | | | 1.43 |
| 35 | F8A1 | 1437 | 2.37 | | | | 1.91 | 1.44 | 2.43 | 2 | | | | 1.97 |
| 36 | FAM83A | 459 | | | | | -3.52 | -9.29 | | | -2.93 | | | |
| 37 | FLJ45858 | 106 | | | | | | | | | | | | |
| 38 | GCNT4 | 1228 | | | | | 1.58 | | 1.36 | 2.36 | 1.5 | | | |
| 39 | GPR162 | 701 | | | | -3.13E+10 | | | | 1.99 | 1.52 | | | -1.57E+10 |
| 40 | GRIK1-AS2 | 1086 | | | | | | | | | | | | |
| 41 | GYG1 | 314, 1141 | 2.28 | | | | 1.78 | 1.67 | | 1.93 | 1.88 | | | |
| 42 | GZMH | 814 | | -3.33 | -4.22 | -1.86E+13 | -2.64 | -4.27 | -4.7 | | -2.53 | -3.87 | -4.51 | -9.28E+12 |
| 43 | H1F0 | 289 | -3.02 | -2 | -1.98 | | | | | | -2.23 | | | |
| 44 | HBQ1 | 867 | | | | | -1.59 | | -1.72 | -2 | | | | |
| 45 | HIST1H2BG | 1281 | | -1.88 | | -5.61E+11 | | | | | | | | -2.81E+11 |
| 46 | HIST1H3J | 1283 | | | | -7.2 | | | | | | | | -4.34 |
| 47 | HLA-DRB1 | 1286 | 2.65 | | 2.35 | 2.58 | 2.12 | | 1.6 | 2.35 | 2.23 | | 1.74 | 1.64 |
| 48 | HMBS | 89, 677 | | | | | -1.99 | | -1.83 | | | | | |

Fig. 10A

| Fig. 9 row | RNA | SEQ ID | log2 Anu/Anorm A | B | C | D | log2 Aslow/Anorm A | B | C | D | log2 Anotnorm/Anorm A | B | C | D |
|---|---|---|---|---|---|---|---|---|---|---|---|---|---|---|
| 49 | let-7a-5p | 516 | | | | | 1.7 | | | | | | | |
| 50 | let-7d-3p | 1489 | | | | | | -2.29 | | | | | -2 | |
| 51 | let-7e-5p | 517 | | | | | | | | | | | | |
| 52 | let-7f-5p | 518 | | | | | | | | | | | | |
| 53 | miR-100-5p | 1830 | | | | | | | | | | | | |
| 54 | miR-106a-5p | 519 | | | | | | | | | | | | |
| 55 | miR-122-5p | 1831 | | | | | | -7.23 | | | | | -6.27 | |
| 56 | miR-1228-5p | 520 | | | | | | -14.71 | | | | | | |
| 57 | miR-1247-3p | 1499 | | | | | -7.4 | | | | | | | |
| 58 | miR-125b-5p | 522 | | | | | | | | | | | | |
| 59 | miR-126b-5p | 1500 | | | | | | | | | | | | |
| 60 | miR-126-3p | 1501 | | | | | | | | | | | | |
| 61 | miR-1270 | 523 | | -1.88 | | | | | | | | | | |
| 62 | miR-1303 | 1508 | | | | | | | | | | | | |
| 63 | miR-134-5p | 1512 | -8.18 | -12.75 | | | -2.36 | | | | -2.4 | -4.22 | -4.88 | |
| 64 | miR-143-3p | 1513 | | | | | | | | | | | | |
| 65 | miR-144-5p | 1514 | | | | | | | | | | | | |
| 66 | miR-146a-5p | 1832 | -2.28 | -2.05 | | | | -1.61 | | | | -1.93 | -1.6 | |
| 67 | miR-146b-5p | 1515 | -2.67 | | | | -2.12 | -1.4 | | | | -2.36 | -1.34 | |
| 68 | miR-148a-3p | 1833 | | | | | -1.98 | -2.87 | -2.53 | | -1.83 | -1.9 | -2.55 | |
| 69 | miR-151a-3p | 525 | -1.92 | | | | -1.81 | | | -2.2 | -1.68 | -1.58 | | |
| 70 | miR-154-5p | 1517 | -20.31 | | | | | -12.77 | | | | -9.71 | | |
| 71 | miR-155-5p | 526 | | | | | | | | | | | | |
| 72 | miR-17-5p | 527 | | | | | | | | | | | | |
| 73 | miR-182-3p | 528 | | -12.55 | | | | | | | | | -6.76 | |
| 74 | miR-18a-5p | 529, 1530 | | | | | | | | | | | | |
| 75 | miR-196a-5p | 1522 | | | | | | | | | | | | |
| 76 | miR-196b-5p | 1523 | | | | | | | | | | | | |
| 77 | miR-1973 | 1524 | | | | | -3.59 | -2.62 | | | -3.11 | | | |
| 78 | miR-1976 | 1526 | | | | | 1.42 | 1.39 | | | | | | 1.59 |
| 79 | miR-195a-5p | 531 | -2.52 | | | | | | | | | -1.88 | | |
| 80 | miR-19b-3p | 1527 | | | | | | | | | | -1.39 | | |
| 81 | miR-202-3p | 1528 | | | | | | 1.78 | | | | | 1.89 | |
| 82 | miR-20a-5p | 1529 | | | | | | | | | | | | |
| 83 | miR-21-5p | 1834 | | | | | | | | | | | | |
| 84 | miR-221-3p | 533 | | -2.68 | | | | | | | | | -1.69 | |
| 85 | miR-223-3p | 534 | | | | | | -1.34 | | | | | -1.52 | |
| 86 | miR-23a-3p | 535 | -8.4 | | | | | -2.82 | -4.89 | | | -2.74 | -4.19 | |
| 87 | miR-24-3p | 1835 | -2.25 | | | | | | | | | -1.52 | | |
| 88 | miR-25-3p | 1836 | | | | | | | | | | | | |
| 89 | miR-25-5p | 1531 | | | | | | -16.59 | | | | | | |
| 90 | miR-27a-3p | 539, 540 | | -1.71 | | | | | | | | | -1.77 | |
| 91 | miR-27b-3p | 541 | | -3.07 | -1.91 | | | | | | | | -1.68 | |
| 92 | miR-29a-3p | 542, 1532 | -2.61 | | | | | | | | | -1.85 | | |
| 93 | miR-29b-3p | 1534 | | | | | | | | | | | | |
| 94 | miR-29c-3p | 1535 | | | | | | | | | | | | |
| 95 | miR-29c-5p | 1536 | | | | | | -2.27 | -2.22 | | | -2.05 | -1.94 | |
| 96 | miR-3117-3p | 1539 | | | -41.18 | | | | | | | | | |
| 97 | miR-31-3p | 1837 | | | | | -4.63 | | -2.7 | | | | | |

Fig. 10B

| Fig. 9 row | RNA | SEQ ID | log2 Alnu/Alnorm | | | | log2 Alslow/Alnorm | | | | log2 Alnotnorm/Alnorm | | | |
|---|---|---|---|---|---|---|---|---|---|---|---|---|---|---|
| | | | A | B | C | D | A | B | C | D | A | B | C | D |
| 99 | miR-3156-5p | 1542 | | | | | | | 5.27 | | | | | |
| 97 | miR-31-5p | 1543 | | | | | | | | | | | | |
| 100 | miR-3176 | 1544 | | | | | | | | -2.03 | | | | |
| 101 | miR-323a-3p | 1546 | | -2.66 | -2.24 | | | | | | | | -2.44 | |
| 102 | miR-323b-3p | 1547 | | | | | 28.26 | | 8.69 | | 21.63 | | 4.13 | |
| 103 | miR-329-3p | 1548 | | -4.69 | | | | | | | | | -4.19 | |
| 104 | miR-335-5p | 543, 1549 | | | | | -1.41 | | | | -1.36 | | | |
| 105 | miR-3613-3p | 1551 | | | | | | -3.21 | -6.12 | -3.76 | | | -5.19 | |
| 106 | miR-3613-5p | 1552 | | | | | | | | | | | | |
| 107 | miR-3667-5p | 1555 | | | | | | | | -2.75 | | | | -2.25 |
| 108 | miR-374b-5p | 1561 | | | | | | | -1.89 | -1.96 | | | -1.82 | -1.69 |
| 109 | miR-376a-3p | 1562 | | -4.58 | | | | | | | | | -2.34 | |
| 110 | miR-378-5p | 1565 | | -3.81 | | | | | | | | | -2.05 | |
| 111 | miR-4284 | 1575 | | | | | | | | | | | | |
| 112 | miR-431-5p | 1576 | -3.86 | -36.17 | -10.2 | | | | | | -4.53 | -15.52 | -6.32 | |
| 113 | miR-4435 | 1579 | -3.21 | | | | | | -3.21 | -3.54 | -2.09 | | -2.72 | |
| 114 | miR-4485 | 1582 | | | | | -28.79 | -3.67 | | | | | | |
| 115 | miR-4525 | 1584 | | | | | | | | -4.01 | | | | |
| 116 | miR-4668-5p | 1585 | | | | | | | | | | | | |
| 117 | miR-4797-5p | 1588 | | | | | -3.31 | | -13.67 | | | | -11.26 | -20.88 |
| 118 | miR-485-3p | 1599 | | -9.45 | | | | | | | | | -5.11 | |
| 119 | miR-487a-5p | 1600 | | | -8.63 | | | | -5.19 | | | | -5.19 | |
| 120 | miR-487b-3p | 1601 | -1.98 | -3.23 | -2.84 | | | | | | | | -1.85 | |
| 121 | miR-495-3p | 1605 | | -2.93 | -3.49 | | | | -1.84 | | | -1.96 | -1.8 | |
| 122 | miR-504-5p | 548 | | | | | | | | 3.11 | | | | |
| 123 | miR-505-3p | 1607 | | | | | | | -2.46 | | | | -2.22 | |
| 124 | miR-5195-3p | 1608 | | -4.45 | | | | | | | | | | |
| 125 | miR-543 | 1609 | | -2.93 | -2.47 | | | | | | | | | |
| 126 | miR-548aa | 1610 | | -2.18 | | | | | -1.55 | -1.69 | | -1.78 | -1.51 | |
| 127 | miR-551a | 549 | | | | -5.74 | | | | | | | | |
| 128 | miR-584-5p | 550 | | | | | | | | | | | | |
| 129 | miR-589-5p | 551 | | | | | | | | | | | | |
| 130 | miR-654-3p | 1627 | | -4.03 | | | | | | | | | -2.47 | |
| 131 | miR-664a-5p | 552 | | | | | | | 2.26 | | | | | |
| 132 | miR-6726-3p | 1628 | -2.16 | | | | | | | | | | | |
| 133 | miR-6770-5p | 1637 | | | | | | | -2.13 | | | | -1.96 | |
| 134 | miR-6777-3p | 1640 | | | | | | | -2.47 | | -1.61 | | -2.23 | |
| 135 | miR-6818-5p | 1643 | | | -3.49 | | -1.79 | -3.42 | | -2.89 | -1.85 | -2.51 | -2.6 | |
| 136 | miR-6820-3p | 1645 | | | | | | | | | | | | |
| 137 | miR-6840-3p | 1648 | | -2.44 | | | 2.17 | | 2.4 | | | | 2.05 | |
| 138 | miR-6855-3p | 1649 | | | | | | | | | | | | |
| 139 | miR-6879-3p | 1652 | -1.99 | | | | | | -1.88 | | | | -1.7 | 1.88 |
| 140 | miR-7-5p | 553, 1656 | | | | | 1.65 | | 1.59 | | | | | 1.85 |
| 141 | miR-7641 | 1657 | | | | | | | | | | | | |
| 142 | miR-7975 | 1662 | -1.92 | -2.84 | | | | | | | | | -1.97 | |
| 143 | miR-93-5p | 555 | | | | | | | | | | | | |
| 144 | miR-98-5p | 1665 | | | | | | | | | | 3.03 | | |
| 145 | HSPA9 | 400 | | | | | | | 1.86 | | | | 1.64 | |

Fig. 10C

| Fig. 9 row | RNA | SEQ ID | log2 A(nu)/A(norm) | | | | log2 A(low)/A(norm) | | | | log2 A(notnorm)/A(norm) | | | |
|---|---|---|---|---|---|---|---|---|---|---|---|---|---|---|
| | | | A | B | C | D | A | B | C | D | A | B | C | D |
| 146 | HSPD1 | 283 | | | | | | | 1.48 | | | | 1.39 | |
| 147 | IFI44 | 573 | | | -3.71 | -4.85E+15 | | | | | | | -2.37 | -2.43E+15 |
| 148 | IFI44L | 572 | | | -4.11 | | | | | | | | -2.41 | |
| 149 | IFI6 | 609 | | | -2.46 | -7.74 | | | | | | | -1.84 | -4.52 |
| 150 | IFIT1 | 655 | | | -2.93 | | | | | | | | -1.93 | |
| 151 | IFIT1B | 64, 654 | | | | | -2.36 | -2.82 | -3.09 | | -2.42 | | | |
| 152 | IFIT2 | 652 | | | -2.18 | | | | | 2.08 | 2.35 | | -1.53 | 1.86 |
| 153 | IFIT3 | 653 | | | -2.67 | | | | | | | | -2.14 | |
| 154 | IFIT5 | 656 | | | -2.04 | -78.98 | | | | | | | -1.55 | -40 |
| 155 | IFITM3 | 682 | | | | | | | | | | -1.94 | | |
| 156 | IFNA16 | 1406 | | | | | | | 3.47E+06 | | | | 49.52 | |
| 157 | IGHA1 | 824 | | | | -2.27 | -1.8 | | | | -1.53 | | | -1.82 |
| 158 | IGKC | 1072, 1071, 1070, 1069, 1068, 1063, 1035, 1032, 1027, 1066, 1030 | -21.02 | | | -8.58 | -12.38 | -4.37E+15 | -5.31 | | -14.54 | -8.81E+10 | -5.69 | -4.31 |
| 159 | IGLC1 | 1109, 1110, 1111, 1114 | | | | -16500 | 2.37 | | | | 2.15 | | | -8260 |
| 160 | IL2RB | 2 | | | | | | | 1.63 | | | | 1.55 | |
| 161 | IL5RA | 1153 | | | -1.55 | | 1.69 | | 1.44 | | | | | |
| 162 | IRF9 | 194 | | | | | | | | | | | | |
| 163 | ITGA2B | 239, 938 | | -2.28 | -2.83 | | | | | 2.1 | | | -2.19 | |
| 164 | ITGB3 | 918 | | | -2.72 | -200 | | | | 3.05 | | | -1.99 | -101 |
| 165 | KCNJ15 | 1100 | 2.42 | | | | 2.16 | | 2.53 | 2.22 | | | | 2.21 |
| 166 | KIF13A | 1279 | | | | -431 | 1.56 | | 2.11 | 1.58 | | | | -216 |
| 167 | KIF1B | 562 | | | | | | | 2.03 | 1.51 | | | | 1.73 |
| 168 | KLK12 | 1084 | 9.59 | | | 4.77E+10 | 5.18E+14 | | 7.04E+14 | 4.77E+10 | 38.34 | | 26.47 | 4.77E+10 |
| 169 | LDH6 | 126 | | | | | | | -1.76 | | | | | |
| 170 | LEF1 | 1201 | | | | -2.08E+10 | 1.77 | | | 2.47 | 1.55 | | | -1.04E+10 |
| 171 | LGALS2 | 1126 | | | | -5.22E+09 | 1.56 | | | 2.26 | 1.48 | | | -2.61E+09 |
| 172 | LOC440300 | 850 | | | | | | | | | | | | |
| 173 | LOC646214 | 855 | | | | | | | | | | -1.99 | | |
| 174 | MANSC1 | 729 | | | | -9.07E+14 | -1.33 | | | | | | | -4.54E+14 |
| 175 | MFSD9 | 1075 | | | | | | | | | | | | |
| 176 | pre-miR29a | 449 | | | | | | | -2.01 | | | | | |
| 177 | MMP9 | 1087 | | | | | | | | | | | | |
| 178 | MT1E | 189 | | | | | | | | | | | | |
| 179 | MT1X | 191 | | | | | | | -1.27 | | | | | |
| 180 | MXD3 | 270 | | | | | | | 2.22 | 1.39 | | | 1.65 | 1.29 |
| 181 | MYL4 | 917 | | | | | | | -1.58 | | | | | |
| 182 | NDUFA2 | 401 | | | | | -1.76 | | | | -3.65 | | | |
| 183 | NFATC1 | 981 | 1.22 | | | 1.37 | 1.55 | | | 1.97 | 1.52 | | | 1.53 |
| 184 | NFATC3 | 4 | | | | | | | 1.72 | | | | 1.49 | |
| 185 | NLRC4 | 1054 | | | | -486000 | | | | 1.79 | 1.59 | | | -243000 |
| 186 | NOTCH3 | 996 | 3.15 | | | 3.14 | 1.68 | | | 2.4 | 1.91 | | | 3.75 |

Fig. 10D

| Fig. 9 row | RNA | SEQ ID | log2 Anu/Anorm | | | | log2 Alxlow/Anorm | | | | log2 Anxnorm/Anorm | | | |
|---|---|---|---|---|---|---|---|---|---|---|---|---|---|---|
| | | | A | B | C | D | A | B | C | D | A | B | C | D |
| 187 | OMG | 991 | | | | | | | | | | | | |
| 188 | RAD14 | 9,563 | | | | | | | | 2.28 | | | | |
| 189 | PDIA3P | 582 | | | | -2.6 | -2.09 | -3.81 | -3.87 | -2.35 | -2.03 | -3.36 | -3.69 | -3.05 |
| 190 | PECAM1 | 1838 | | | | | | | | | | | | |
| 191 | PET100 | 968 | | | | | | | | | | | | |
| 192 | PI3 | 1086 | | | | | | | | -1.44 | | | | |
| 193 | PPDPF | 291 | | | | | -1.87 | | -3.17 | -2.34 | -1.85 | | | |
| 194 | PRKXP1 | 864 | | | | -315000 | | | | 2.06 | | | | -158000 |
| 195 | PROS1 | 1154 | | | | | | | | 2.25 | | | | |
| 196 | PYGL | 164, 816 | | | | | 1.58 | | | 1.94 | 1.64 | | | 1.77 |
| 197 | RAB39A | 676 | 1.42 | | | 1.63 | 1.72 | | | 2.17 | 1.7 | | | 1.85 |
| 198 | RAD23A | 239 | -2.31 | | | | | | -1.89 | | -1.94 | | | |
| 199 | RBBP8 | 954 | | | | | 2.96 | | | 2.57 | 2.48 | | | 2.37 |
| 200 | ROPN1L | 371 | | | | | | 2.95 | 1.6 | | | | 1.7 | |
| 201 | RPS15 | 279 | | | | | -1.34 | -1.57 | -1.53 | -1.48 | | | | -1.31 |
| 202 | RPS27 | 347 | | | | -2.57 | -1.89 | | | | | | | |
| 203 | RUNDC3A | 915 | | | | | | | | -1.94 | | | | |
| 204 | S100A12 | 5,818 | | -2.99 | | | -1.72 | | -2.35 | | -2.07 | | | |
| 205 | S100P | 344 | | | | | -1.8 | | | | | | | |
| 206 | SELP | 625 | | -2.47 | -2.48 | -3200 | | | | 2.77 | | | -1.92 | -3200 |
| 207 | SMAD4 | 958 | | | | -6.99 | 1.52 | | | 2.08 | 1.49 | | | -3.97 |
| 208 | SMN1 | 1216 | | | | 1.73 | | | | | | | | 1.28 |
| 209 | SNORA14A | 1318 | | | | | -1.47 | | | | | | | |
| 210 | SNORD13 | 228 | | | | | | | | 1.48 | | | 1.44 | |
| 211 | SNORD14E | 184 | | | | | | | | 1.58 | | | 1.53 | |
| 212 | SNORD25 | 6,99 | | | | | -1.48 | | | | | | | |
| 213 | SNORD48 | 914 | 9.05 | | | 67.76 | 71.36 | | 90.76 | 87.16 | 26.21 | | 32.83 | 54.77 |
| 214 | SNORD59B | 134 | | | | | -5.87 | -1.73 | | | | | | |
| 215 | SPTA1 | 620 | | | | -3200 | -1.97 | | -2.38 | | -2.05 | | -1.96 | -3200 |
| 216 | THBS1 | 844 | | | | | | | | 2.26 | | | | |
| 217 | TLR5 | 53 | | | | | | 2.22 | | | | | | |
| 218 | TMEM158 | 1153 | -3.9 | | | | -4.48 | -5.86 | -6.88 | -2.78 | -4.32 | -5.05 | -5.98 | |
| 219 | TMEM176A | 1537 | | | | 4.89 | | | 3.09 | 4.21 | 2.38 | | 3.53 | 4.03 |
| 220 | TMEM176B | 1363 | | | | | | | | 3.03 | | | | 2.48 |
| 221 | TNFRSF9 | 682 | | | | | | | | 1.75 | | | | |
| 222 | TREML1 | 1288 | | -2.27 | | | | | | | | | | |
| 223 | TRNN | 7, 30, 497 | | | | | | | | | | | 1.3 | |
| 224 | TSTA3 | 471 | | -1.81 | | | -2.16 | | | | -2.14 | | | |
| 225 | TUBB2A | 1244, 1245, 1277 | | | | | | | -1.92 | | | | | |
| 226 | U388 | 1677 | | | | | -1.42 | | | | | | | |
| 227 | USP32P1 | 912 | | | | | | | | | | | | 2.33 |
| 228 | YME1L1 | 765, 771, 768, 769, 764, 760, 762, 766, 770, 777, 781, 785, 794, 788, 791 | | | | | 1.35 | | | 1.89 | 1.35 | | | |

Fig. 10E

| Fig. 9 row | RNA | SEQ ID | log2 B/A | | | | log2 C/A | | | | log2 D/A | | | |
|---|---|---|---|---|---|---|---|---|---|---|---|---|---|---|
| | | | Anorm | Anu | Aslow | Anotnorm | Anorm | Anu | Aslow | Anotnorm | Anorm | Anu | Aslow | Anotnorm |
| 1 | A2M | 722 | | | | | 9.46E+07 | -5.03E+06 | -3.51E+08 | -2.95E+08 | 0.99 | -4.65 | -1.23 | -2.37 |
| 2 | A2M-AS1 | 703 | -0.02 | -0.45 | 0.95 | 0.25 | | | | | | | | |
| 3 | A2MP1 | 724 | | | | | -1.2 | 14.19 | 5.36 | 7.77 | | | | |
| 4 | ADGRE1 | 966 | | | | | -0.66 | 0.38 | -0.33 | -0.14 | 0.1 | -6.72 | -0.37 | -2.49 |
| 5 | AIF1 | 1,408, 513, 515 | -2.59E+11 | -5.26E+11 | -2.74E+12 | -1.85E+12 | | | | | | | | |
| 6 | ANKRD22 | 75 | | | | | | | | | | | | |
| 7 | ANKRD36B | 1074 | | | | | 0.36 | -0.11 | 0.17 | 0.09 | 1.04 | -6.34 | 0.49 | -1.79 |
| 8 | ANPEP | 862 | -0.81 | 0.95 | 0.06 | 0.51 | -0.42 | 0.43 | -0.3 | -0.1 | 0.2 | -6.93 | -0.78 | -2.83 |
| 9 | ANXA3 | 349 | -1.03E+07 | -3.87E+06 | -4.41E+07 | -2.80E+07 | | | | | | | | |
| 10 | ARG1 | 413 | | | | | -1.39 | -0.23 | -3.57 | -2.74 | | | | |
| 11 | ARPP19 | 388 | | | | | | | | | | | | |
| 12 | ATG9A | 1080 | | | | | -0.31 | -0.29 | -1.17 | -0.93 | -0.09 | -7.31 | -0.94 | -3.06 |
| 13 | C4BPA | 598 | | | | | -9.14E+09 | 3.53E+10 | 1.18E+10 | 1.76E+10 | -1.08E+11 | 3.63E+14 | -2.10E+09 | 1.21E+14 |
| 14 | CASP5 | 103, 598 | | | | | -0.46 | 1.13 | 1.35 | 1.29 | 0.24 | -5.69 | -0.06 | -1.93 |
| 15 | CCDC144A | 910, 911 | | | | | -4.68 | 0 | 3.39 | 2.47 | | | | |
| 16 | CCR7 | 934 | | | | | 0.5 | -0.13 | 0.04 | -0.01 | 1.13 | -6.8 | 0.52 | -1.82 |
| 17 | CD27 | 700 | | | | | | | | | 0.59 | -5.51 | 0.26 | -2 |
| 18 | CES1 | 885 | -1.57 | 0.23 | -0.92 | -0.34 | -1.11 | 0.36 | -0.22 | -0.06 | -0.19 | -5.85 | -0.9 | -2.55 |
| 19 | CHRM3-AS2 | 634 | | | | | | | | | 0.93 | -6.18 | 0.7 | -1.59 |
| 20 | CLEC1B | 124, 725 | | | | | -0.57 | 0.28 | -1.35 | -0.9 | -0.6 | -6.36 | -1.39 | -3.05 |
| 21 | CLEC4D | 109, 702 | -0.76 | -0.66 | -2.75 | -1.94 | -1.80E+11 | -2.32E+10 | -5.26E+11 | -4.00E+11 | | | | |
| 22 | CLEC4E | 721 | | | | | | | | | -0.03 | -7.31 | -0.99 | -3.1 |
| 23 | CLIC2 | 512 | | | | | -0.5 | -0.3 | -2.26 | -1.77 | | | | |
| 24 | CLU | 1382 | | | | | | | | | -0.42 | -7.8 | -1.09 | -3.33 |
| 25 | CMTM2 | 889 | | | | | -2.15E+07 | -7.20E+06 | 3.37E+07 | 2.39E+07 | -1.30E+11 | 1.57E+15 | -3.65E+11 | 5.23E+14 |
| 26 | COX7B | 1431 | | | | | | | | | -0.16 | -6.26 | -1.75 | -3.25 |
| 27 | CR1 | 24, 599 | | | | | -0.8 | 0.55 | -0.37 | -0.12 | -0.11 | -6.81 | -0.81 | -2.81 |
| 28 | CSNK1A1L | 753 | -0.98 | 1.29 | -0.79 | 0.25 | | | | | 0.1 | -6.19 | -0.63 | -2.48 |
| 29 | CST7 | 290 | -1.12E+12 | -6.81E+11 | -4.26E+12 | -2.83E+12 | -0.29 | 1.42 | -0.12 | 0.26 | -0.62 | 0.23 | -0.52 | -0.27 |
| 30 | DSC2 | 962 | -1.17 | 0.84 | -0.43 | 0.2 | -0.6 | 0.36 | 0.2 | 0.24 | 0.14 | -6.62 | -0.43 | -2.49 |
| 31 | DYSF | 1024 | | | | | | | | | 0.76 | -6.85 | -0.89 | -2.89 |
| 32 | EGF | 351 | | | | | | | | | 0.21 | -9.28 | -1.27 | -3.94 |
| 33 | EIF4B | 132 | | | | | -0.18 | 0.27 | -0.2 | -0.08 | | | | |
| 34 | F5 | 45, 624 | -1.25 | 0.6 | -0.58 | 0.01 | -0.88 | 0.1 | -0.53 | -0.36 | -0.2 | -6.44 | -0.97 | -2.79 |
| 35 | F8A1 | 1437 | -0.75 | 1.04 | -0.2 | 0.42 | | | | | 0.65 | -6.12 | 0.08 | -1.99 |
| 36 | FAM83A | 459 | | | | | -1.57E+10 | -1.15E+10 | -7.10E+10 | -5.51E+10 | | | | |
| 37 | FLJ45950 | 106 | | | | | | | | | | | | |
| 38 | GCNT4 | 1228 | | | | | | | | | 1.24 | -6.13 | 0.73 | -1.56 |
| 39 | GPR162 | 701 | | | | | | | | | 0.81 | -5.94 | -0.06 | -2.02 |
| 40 | GRIK1-AS2 | 1096 | | | | | | | | | | | | |
| 41 | GYG1 | 314 | | | | | -0.8 | 0.15 | -0.8 | -0.54 | -0.23 | -6.94 | -0.91 | -2.92 |

Fig. 10F

| Fig. 9 row | RNA | SEQ ID | log2 B/A | | | | log2 C/A | | | | log2 D/A | | | |
|---|---|---|---|---|---|---|---|---|---|---|---|---|---|---|
| | | | Anorm | Anu | Aslow | Anotnorm | Anorm | Anu | Aslow | Anotnorm | Anorm | Anu | Aslow | Anotnorm |
| 42 | GZMH | 814 | | | | | | | | | 1.3 | -5.36 | 0.93 | -1.18 |
| 43 | H1F0 | 299 | | | | | | | | | | | | |
| 44 | HBQ1 | 867 | | | | | | | | | -0.77 | -8.02 | -0.97 | -3.32 |
| 45 | HIST1H2BG | 1281 | -0.7 | 0.67 | -0.36 | 0.15 | | | | | 0.78 | -6.25 | -0.6 | -2.48 |
| 46 | HIST1H3J | 1283 | | | | | | | | | 0.36 | -6.47 | 0.04 | -2.13 |
| 47 | HLA-DRB1 | 1286 | -3.30E+11 | 1.87E+11 | 1.11E+12 | 7.41E+11 | | | | | 0.99 | -7.18 | 0.36 | -2.15 |
| 48 | HMBS | 89, 577 | | | | | -0.13 | -0.17 | -1.56 | -1.22 | | | | |
| 49 | let-7a-5p | 516 | | | | | | | | | 0.96 | -7.46 | 0.79 | -1.96 |
| 50 | let-7d-3p | 1489 | | | | | | | | | 2.25 | -7.43 | 0.48 | -2.16 |
| 51 | let-7e-5p | 517 | -1.83E+12 | 8.14E+12 | 2.50E+12 | 4.76E+12 | | | | | 1.23 | -7.68 | 0.74 | -2.06 |
| 52 | let-7f-5p | 518 | | | | | | | | | | | | |
| 53 | miR-100-5p | 1830 | | | | | | | | | 1.01 | -5.9 | 0.96 | -1.33 |
| 54 | miR-106a-5p | 519 | | | | | | | | | | | | |
| 55 | miR-122-5p | 1831 | 1510 | 43.7 | -29100 | -17400 | | | | | | | | |
| 56 | miR-1228-5p | 520 | | | | | | | | | | | | |
| 57 | miR-1247-3p | 1499 | | | | | -35.8 | 261 | 0 | 85.3 | | | | |
| 58 | miR-1255b-5p | 522 | 0.09 | -0.34 | 3.36 | 1.88 | 0.11 | 1.39 | 2.05 | 1.83 | | | | |
| 59 | miR-125b-5p | 1500 | | | | | | | | | 1.45 | -6.27 | 0.71 | -1.51 |
| 60 | miR-126-3p | 1501 | | | | | | | | | 0.53 | -8.06 | 0.21 | -2.55 |
| 61 | miR-1270 | 523 | 2.29 | 17.9 | 10.18 | 13.3 | | | | | -0.72 | 5.65 | 4.13 | 4.54 |
| 62 | miR-1303 | 1508 | | | | | | | | | | | | |
| 63 | miR-134-5p | 1512 | | | | | 6.61E+07 | 6.01E+08 | 4.32E+07 | 1.83E+08 | 2.85 | -7.84 | 0.91 | -2.01 |
| 64 | miR-143-3p | 1513 | | | | | | | | | | | | |
| 65 | miR-144-5p | 1514 | | | | | | | | | 2.25 | -6.57 | 1.03 | -1.51 |
| 66 | miR-146a-5p | 1832 | -3.12E+10 | 5.92E+12 | 1.26E+12 | 3.12E+12 | | | | | 0.96 | -2.72 | 0.06 | -0.86 |
| 67 | miR-146b-5p | 1515 | -6.15E+11 | 2.55E+12 | 7.56E+11 | 1.48E+12 | | | | | 0.55 | -7.98 | -0.51 | -3 |
| 68 | miR-148a-3p | 1833 | -1.54E+11 | 8.57E+11 | 3.30E+11 | 5.41E+11 | | | | | 0.99 | -7.1 | -0.29 | -2.56 |
| 69 | miR-151a-3p | 525 | 0.21 | -0.19 | 2.89 | 1.66 | | | | | | | | |
| 70 | miR-154-5p | 1517 | 5.40E+07 | -1.18E+10 | 1.87E+08 | -4.62E+09 | -340 | -143 | 2810 | 2070 | | | | |
| 71 | miR-155-5p | 526 | | | | | | | | | 2.08 | -6.69 | 0.53 | -1.88 |
| 72 | miR-17-5p | 527 | | | | | | | | | | | | |
| 73 | miR-182-3p | 528 | | | | | -109 | 10300 | -893 | 1910 | | | | |
| 74 | miR-18a-5p | 529 | | | | | | | | | | | | |
| 75 | miR-196a-5p | 1522 | | | | | | | | | 2.02 | -4.74 | 1 | -0.91 |
| 76 | miR-196b-5p | 1523 | | | | | | | | | 1.22 | -5.9 | 0.51 | -1.53 |
| 77 | miR-1973 | 1524 | | | | | | | | | 2.94 | -3.92 | -0.16 | -1.41 |
| 78 | miR-1976 | 1526 | | | | | | | | | 2.41 | -6.66 | 1.01 | -1.55 |
| 79 | miR-199a-5p | 531 | 0.73 | 10.32 | 7.43 | 8.59 | | | | | -3.08 | 4.84 | 2.01 | 2.95 |
| 80 | miR-19b-3p | 1527 | -4.67E+13 | 1.04E+14 | -3.28E+11 | 4.14E+13 | | | | | 0.52 | -8.97 | -0.27 | -3.17 |
| 81 | miR-202-3p | 1528 | | | | | | | | | | | | |
| 82 | miR-20a-5p | 1529 | | | | | | | | | 0.33 | -8.33 | 0.09 | -2.71 |
| 83 | miR-21-5p | 1834 | -4.59E+11 | 2.39E+12 | 7.51E+11 | 1.41E+12 | | | | | 0.98 | -7.18 | 0 | -2.39 |

Fig. 10G

| Fig. 9 row | RNA | SEQ ID | log2 B/A | | | | log2 C/A | | | | log2 D/A | | | |
|---|---|---|---|---|---|---|---|---|---|---|---|---|---|---|
| | | | Anorm | Anu | Aslow | Anotnorm | Anorm | Anu | Aslow | Anotnorm | Anorm | Anu | Aslow | Anotnorm |
| 84 | miR-221-3p | 533 | 0.87 | 2.89 | 8.83 | 6.45 | | | | | | | | |
| 85 | miR-223-3p | 534 | | | | | | | | | 0.77 | -9.42 | -0.1 | -3.21 |
| 86 | miR-23a-3p | 535 | 253000 | -845000 | 2.11E+06 | 925000 | | | | | | | | |
| 87 | miR-24-3p | 1835 | -5.93E+12 | 1.67E+13 | 2.96E+12 | 8.44E+12 | | | | | 0.43 | -8.53 | -0.55 | -3.21 |
| 88 | miR-25-3p | 1836 | -3.89E+12 | 1.49E+13 | 7.97E+12 | 1.07E+13 | | | | | 0.86 | -8.31 | 0.15 | -2.67 |
| 89 | miR-25-5p | 1531 | | | | | 1.70E+06 | 352000 | 1.19E+06 | 8.92E+07 | | | | |
| 90 | miR-27a-3p | 539, 540 | 0.56 | 2.55 | 8.46 | 6.09 | | | | | | | | |
| 91 | miR-27b-3p | 541 | 1.37 | 2.14 | 8.16 | 5.75 | | | | | | | | |
| 92 | miR-29a-3p | 542 | -6.11E+11 | 1.49E+12 | -9.20E+10 | 5.24E+11 | | | | | 0.64 | -7.95 | -0.71 | -3.13 |
| 93 | miR-29b-3p | 1534 | -82100 | 259000 | 162000 | 201000 | | | | | | | | |
| 94 | miR-29c-3p | 1535 | | | | | | | | | 0.32 | -7.77 | -0.55 | -2.96 |
| 95 | miR-29c-5p | 1536 | | | | | | | | | 0.79 | -6.06 | -0.06 | -2.06 |
| 96 | miR-3117-3p | 1539 | 0.28 | -2.54 | -4.88 | -3.71 | | | | | | | | |
| 98 | miR-31-3p | 1837 | | | | | | | | | | | | |
| 99 | miR-3156-5p | 1542 | | | | | | | | | | | | |
| 97 | miR-31-5p | 1543 | | | | | | | | | | | | |
| 100 | miR-3176 | 1544 | | | | | | | | | | | | |
| 101 | miR-323a-3p | 1546 | 6.53E+09 | 1.98E+11 | 1.19E+10 | 8.64E+10 | | | | | 541000 | -2.33E+06 | -310000 | -984000 |
| 102 | miR-323b-3p | 1547 | 1.51 | -8.96 | 4.07 | -2.45 | | | | | 1.24 | -6.22 | 3.53 | 0.28 |
| 103 | miR-329-3p | 1548 | | | | | | | | | 1.48E+09 | -7.34E+09 | 1.26E+08 | -2.36E+09 |
| 104 | miR-335-5p | 543 | | | | | | | | | | | | |
| 105 | miR-3613-3p | 1551 | 1.72E+08 | -1.41E+10 | 2.07E+08 | -5.53E+09 | 7.78E+07 | -1.68E+08 | 9.19E+06 | 6.47E+08 | 5.68 | -5.31 | 5.88 | 2.15 |
| 106 | miR-3613-5p | 1552 | | | | | 0.39 | 12.48 | -0.11 | 3.32 | | | | |
| 107 | miR-3687-5p | 1555 | | | | | | | | | 0.67 | -7.48 | 0.28 | -2.3 |
| 108 | miR-374b-5p | 1561 | | | | | | | | | 0.46 | -6.81 | 0.22 | -2.13 |
| 109 | miR-376a-3p | 1562 | | | | | -253000 | -1.19E+06 | -463000 | -644000 | | | | |
| 110 | miR-379-5p | 1565 | -3.01 | -0.46 | 9.47 | 4.5 | -6.42E+08 | 9.80E+09 | 2.65E+08 | 2.65E+08 | 5.73E+09 | -7.33E+10 | -1.28E+09 | -2.53E+10 |
| 111 | miR-4284 | 1575 | | | | | 1.54 | -1.59 | -0.29 | -0.65 | 1.66 | -1.77 | 0.08 | -0.54 |
| 112 | miR-431-5p | 1576 | | | | | 6.59E+08 | -7.04E+09 | -1.17E+09 | -2.64E+09 | -2.06 | -17.5 | -10.87 | -13.2 |
| 113 | miR-4435 | 1579 | | | | | | | | | 1.82 | -5.57 | 2.29 | -0.33 |
| 114 | miR-4485 | 1582 | | | | | | | | | 4.28 | -0.73 | 1.25 | 0.59 |
| 115 | miR-4525 | 1584 | 0 | 0 | 0.33 | 0.2 | | | | | | | | |
| 116 | miR-4668-5p | 1585 | -688000 | 0 | -6.68E+06 | -4.01E+06 | | | | | | | | |
| 117 | miR-4797-5p | 1598 | | | | | | | | | | | | |
| 118 | miR-485-3p | 1599 | 343000 | 7.82E+06 | 302000 | 3.31E+06 | | | | | 2.52 | -6.33 | 1.43 | -1.16 |
| 119 | miR-487a-3p | 1600 | | | | | | | | | 4.87 | -11.50 | 2.18 | -2.57 |
| 120 | miR-4876-3p | 1601 | | | | | 18800 | -201000 | -94400 | -146000 | | | | |
| 121 | miR-495-3p | 1605 | 4.08E+09 | 4.24E+10 | 6.21E+09 | 2.07E+10 | | | | | 158000 | -1.17E+06 | -587000 | -782000 |
| 122 | miR-504-5p | 548 | | | | | | | | | -3.02 | 4.76 | 1.38 | 2.51 |
| 123 | miR-505-3p | 1507 | | | | | 106000 | -358000 | 496000 | 283000 | 6.4 | -10.78 | -0.07 | -3.64 |
| 124 | miR-5195-3p | 1508 | -0.75 | 2.2 | -0.28 | 0.96 | | | | | | | | |
| 125 | miR-543 | 1609 | | | | | | | | | 1.79 | -7 | 0.72 | -1.86 |

Fig. 10H

| Fig. 9 row | RNA | SEQ ID | log2 B/A | | | | log2 C/A | | | | log2 D/A | | | |
|---|---|---|---|---|---|---|---|---|---|---|---|---|---|---|
| | | | Alnorm | Alnu | Alslow | Alnotnorm | Alnorm | Alnu | Alslow | Alnotnorm | Alnorm | Alnu | Alslow | Alnotnorm |
| 126 | miR-548aa | 1810 | -3.24E+11 | 2.97E+12 | 1.20E+11 | 1.26E+12 | | | | | 0.71 | -7.73 | 0.33 | -2.35 |
| 127 | miR-551a | 549 | -3.72E+08 | 9.10E+08 | -1.84E+08 | 2.53E+08 | | | | | -6.36 | 3.55 | -0.07 | 1.14 |
| 128 | miR-584-5p | 550 | 1.51 | 2.01 | 8.2 | 5.73 | | | | | | | | |
| 129 | miR-589-5p | 551 | 0.84 | 1.84 | 6.72 | 4.77 | | | | | 0.05 | -2.59 | -0.15 | -0.97 |
| 130 | miR-664-3p | 1627 | -3.09E+08 | -2.51E+11 | 6.17E+09 | -9.67E+10 | 8320 | -209000 | -21300 | -68300 | -2650 | -223000 | -135000 | -164000 |
| 131 | miR-664a-5p | 552 | 1.3 | 9.38 | 6.52 | 7.67 | | | | | | | | |
| 132 | miR-6726-3p | 1628 | -1.11E+10 | -4.09E+11 | 1.09E+10 | -1.59E+11 | 200000 | -678000 | 465000 | 172000 | 6.50E+10 | -2.01E+11 | 2.56E+10 | -4.98E+10 |
| 133 | miR-6770-5p | 1637 | | | | | 2390 | 10200 | 35300 | 29000 | | | | |
| 134 | miR-6777-3p | 1640 | | | | | | | | | 2.73 | -2 | 1.87 | 0.58 |
| 135 | miR-6818-5p | 1643 | -6.45E+08 | -3.78E+10 | 2.16E+08 | -1.50E+10 | | | | | 4.00E+08 | -1.97E+10 | 1.68E+09 | -5.45E+09 |
| 136 | miR-6820-3p | 1645 | | | | | | | | | 2.1 | -5.24 | 1.31 | -0.87 |
| 137 | miR-6840-3p | 1648 | -1.13E+13 | 4.31E+13 | 9.05E+12 | 2.27E+13 | | | | | | | | |
| 138 | miR-6855-3p | 1649 | | | | | | | | | 2.44 | -5.04 | 0.94 | -1.06 |
| 139 | miR-6879-3p | 1652 | | | | | | | | | 3.76 | -6.47 | 1.87 | -0.91 |
| 140 | miR-7-5p | 553, 1656 | | | | | | | | | 2.19 | -6.58 | 0.73 | -1.37 |
| 141 | miR-7641 | 1657 | 6.93E+10 | 1.53E+11 | -8.04E+11 | -4.21E+11 | | | | | 0.8 | -7.99 | -1.77 | -3.84 |
| 142 | miR-7975 | 1662 | | | | | -1.10E+12 | -6.88E+12 | -2.57E+12 | -4.15E+12 | -0.58 | -6.93 | -0.91 | -2.92 |
| 143 | miR-93-5p | 556 | -0.15 | 1.06 | 3.51 | 2.53 | | | | | | | | |
| 144 | miR-98-5p | 1665 | -3.1 | -0.84 | 5.65 | 2.4 | | | | | | | | |
| 145 | HSPA9 | 400 | -0.08 | -0.54 | -0.83 | -0.72 | | | | | | | | |
| 146 | HSPD1 | 283 | | | | | | | | | | | | |
| 147 | IFI44 | 573 | | | | | -0.21 | 1.82 | 0.21 | 0.85 | 0.58 | -6.13 | -0.18 | -2.16 |
| 148 | IFI44L | 572 | | | | | -0.19 | 1.64 | 0.53 | 0.83 | 0.61 | -7.11 | 0.18 | -2.25 |
| 149 | IFI6 | 609 | | | | | -0.15 | 1.05 | 0.52 | 0.67 | 0.56 | -8.09 | 0.17 | -2.59 |
| 150 | IFIT1 | 655 | | | | | -0.21 | 1.82 | 0.46 | 0.83 | 0.41 | -7.33 | -0.15 | -2.55 |
| 151 | IFIT1B | 64, 554 | | | | | -0.52 | 0.07 | -2.26 | -1.68 | | | | |
| 152 | IFIT2 | 652 | | | | | -0.27 | 1.56 | 0.39 | 0.71 | 0.36 | -6.46 | -0.24 | -2.31 |
| 153 | IFIT3 | 653 | | | | | -0.26 | 1.81 | 0.59 | 1 | 0.4 | -7.13 | -0.24 | -2.54 |
| 154 | IFIT5 | 655 | | | | | -0.3 | 1 | 0.19 | 0.41 | 0.43 | -6.05 | -0.35 | -2.25 |
| 155 | IFITM3 | 682 | | | | | | | | | | | | |
| 156 | IFNA16 | 1406 | | | | | -0.04 | 0.11 | 5.84 | 4.28 | | | | |
| 157 | IGHA1 | 824 | | | | | 0.3 | -0.23 | -1.03 | -0.81 | 0.15 | -7.13 | -1.1 | -3.11 |
| 158 | IGKC | 1073, 1071, 1070, 1069, 1068, 1063, 1035, 1032, 1027, 1058, 1030 | | | | | | | | | 1.32 | -0.26 | -10.11 | -6.83 |
| 159 | IGLC1 | 1109, 1110, 1111, 1114, 1115 | | | | | | | | | 1.31 | -5.01 | 0.13 | -1.59 |
| 160 | IL2RB | 2 | | | | | | | | | | | | |
| 161 | IL5RA | 1151 | | | | | | | | | 1.48 | -6.11 | 0.41 | -1.76 |
| 162 | IRF8 | 194 | | | | | -3.14 | 17.6 | -0.03 | 4.38 | | | | |
| 163 | ITGA2B | 219, 938 | | | | | | | | | -0.84 | -7.4 | -1.48 | -3.45 |

Fig. 10I

| Fig. 9 row | RNA | SEQ ID | log2 B/A | | | | log2 C/A | | | | log2 D/A | | | |
|---|---|---|---|---|---|---|---|---|---|---|---|---|---|---|
| | | | Anorm | Alnu | Aslow | Alnotnorm | Anorm | Alnu | Aslow | Alnotnorm | Anorm | Alnu | Aslow | Alnotnorm |
| 164 | ITGB3 | 918 | | | | | | | | | -0.39 | -7.51 | -1.19 | -3.3 |
| 165 | KCNJ15 | 1100 | -1.15 | 1.15 | -0.72 | 0.21 | -0.63 | 0.47 | -0.14 | 0.03 | -0.15 | -5.66 | -0.89 | -2.81 |
| 166 | KIF13A | 1279 | -0.5 | 1.32 | -0.27 | 0.52 | -0.49 | 0.37 | -0.28 | -0.1 | 0.19 | -6.01 | -0.67 | -2.45 |
| 167 | KIF1B | 562 | -0.99 | 0.92 | -0.71 | 0.1 | -0.61 | 0.57 | -0.35 | -0.1 | 0.11 | -6.06 | -0.75 | -2.52 |
| 168 | KLK12 | 1004 | | | | | | | | | | | | |
| 169 | LDHB | 126 | | | | | | | | | | | | |
| 170 | LEF1 | 1201 | | | | | | | | | 1.18 | -5.66 | 0.63 | -1.8 |
| 171 | LGALS2 | 1126 | | | | | | | | | 0.28 | -6.54 | -0.41 | -2.45 |
| 172 | LOC440200 | 850 | | | | | 5.54E+09 | 7.68E+09 | 3.57E+07 | 2.87E+07 | | | | |
| 173 | LOC646214 | 859 | | | | | | | | | | | | |
| 174 | MAN8C1 | 729 | -0.85 | 1.1 | -0.94 | 0.08 | | | | | 1.27 | 1.3 | -0.9 | 3.72 |
| 175 | MFSD9 | 1075 | -9.93E+09 | -2.33E+09 | 1.08E+10 | 5.52E+09 | | | | | 0.3 | -6.24 | -0.41 | -2.35 |
| 176 | pre-miR29a | 449 | | | | | | | | | | | | |
| 177 | MMP9 | 1087 | -1.5 | 0.82 | -0.84 | -0.01 | | | | | -0.62 | -6.83 | -2.01 | -3.62 |
| 178 | MT1E | 189 | -0.58 | -2.26 | 8.53 | 4.21 | -0.08 | -0.05 | 3.92 | 2.92 | | | | |
| 179 | MT1X | 191 | | | | | | | | | | | | |
| 180 | MXD3 | 270 | -3.79E+11 | -2.51E+11 | -1.54E+12 | -1.02E+12 | -0.43 | 0.29 | -0.36 | -0.2 | | | | |
| 181 | MYL4 | 917 | | | | | -0.3 | -0.51 | -1.42 | -1.17 | -0.7 | -7.67 | -1.22 | -3.37 |
| 182 | NDUFA2 | 401 | -1.59E+11 | -2.13E+11 | -1.43E+12 | -9.45E+11 | -1.37E+11 | -2.01E+11 | -8.88E+11 | -7.16E+11 | -2.63E+11 | -1.94E+11 | -8.19E+11 | -6.10E+11 |
| 183 | NFATC1 | 961 | -0.14 | 0.11 | 0.21 | 0.16 | | | | | 0.99 | -6.04 | 0.35 | -1.78 |
| 184 | NFATC2 | 4 | | | | | | | | | | | | |
| 185 | NLRC4 | 1054 | | | | | -0.8 | 0.34 | -0.59 | -0.34 | -0.11 | -6.76 | -0.92 | -2.87 |
| 186 | NOTCH3 | 996 | | | | | | | | | | | | |
| 187 | OMG | 931 | -0.77 | 1.05 | -0.46 | 0.3 | | | | | 0.4 | -5.73 | -0.15 | -2.01 |
| 188 | PAQR4 | 5, 563 | -0.8 | 0.92 | -0.45 | 0.24 | | | | | -0.14 | -7.33 | -1.39 | -3.37 |
| 189 | PDIA3P | 582 | | | | | -7.49E+09 | 2.39E+11 | 8.47E+10 | 1.23E+11 | 1.25 | -6.59 | 0.16 | -1.75 |
| 190 | PECAM1 | 1838 | | | | | | | | | | | | |
| 191 | PET100 | 968 | -0.92 | 0.54 | 0.15 | 0.34 | | | | | 0.12 | -6.33 | -0.82 | -2.65 |
| 192 | PI3 | 1085 | | | | | | | | | 0.28 | -6.87 | -0.1 | -2.36 |
| 193 | PPOPF | 291 | | | | | | | | | | | | |
| 194 | PRKXP1 | 864 | | | | | | | | | 1.07 | -5.69 | 0.7 | -1.43 |
| 195 | PROS1 | 1154 | | | | | | | | | -0.04 | -7.12 | -1.57 | -3.42 |
| 196 | PYGL | 164, 819 | | | | | -0.68 | 0.42 | -0.5 | -0.25 | -0.12 | -7.07 | -0.92 | -2.97 |
| 197 | RAB39A | 675 | -2.11E+09 | -3.62E+08 | 3.87E+08 | 3.77E+07 | -1.94E+09 | -3.73E+07 | 5.98E+08 | 4.39E+08 | 0.76 | -5.43 | -0.61 | -2.22 |
| 198 | RAD23A | 239 | | | | | 0.06 | 0.31 | -0.88 | -0.58 | | | | |
| 199 | RBBP8 | 954 | | | | | | | | | 0.11 | -6.85 | -0.67 | -2.73 |
| 200 | ROPN1L | 371 | | | | | -1.31E+11 | 6.34E+10 | -1.78E+11 | -1.17E+11 | | | | |
| 201 | RPS15 | 279 | | | | | | | | | | | | |
| 202 | RPS27 | 347 | 1.01E+10 | -7.10E+12 | -2.31E+13 | -1.57E+13 | -1.40E+12 | -4.69E+12 | -1.28E+13 | -1.08E+13 | | | | |
| 203 | RUNDC3A | 915 | | | | | | | | | -0.49 | -7.73 | -0.61 | -2.98 |
| 204 | S100A12 | 5, 618 | -1.39 | -0.69 | -3.52 | -2.38 | -1.13E+12 | -7.36E+11 | -4.55E+12 | -3.60E+12 | | | | |
| 205 | S100P | 344 | | | | | | | | | | | | |

Fig. 10J

| Fig. 9 row | RNA | SEQ ID | log2 B/A | | | | log2 C/A | | | | log2 D/A | | | |
|---|---|---|---|---|---|---|---|---|---|---|---|---|---|---|
| | | | Alnorm | Alnu | Alslow | Alnotnorm | Alnorm | Alnu | Alslow | Alnotnorm | Alnorm | Alnu | Alslow | Alnotnorm |
| 206 | SELP | 625 | | | | | | | | | -0.74 | -19.57 | -0.97 | -7.17 |
| 207 | SMAD4 | 958 | | | | | | | | | 0.54 | -6.73 | -0.27 | -2.43 |
| 208 | SMN1 | 1215 | -5.95E+09 | -6.32E+09 | 4.26E+10 | 2.30E+10 | 0.04 | -0.4 | 0 | -0.11 | 0.79 | -6.56 | 0.16 | -2.08 |
| 209 | SNORA14A | 1318 | -2.86E+08 | -9.02E+09 | 9.57E+10 | 5.38E+10 | | | | | 0.61 | -6.39 | 0.08 | -2.08 |
| 210 | SNORD13 | 228 | | | | | | | | | | | | |
| 211 | SNORD14E | 104 | | | | | | | | | | | | |
| 212 | SNORD25 | 6, 99 | | | | | | | | | | | | |
| 213 | SNORD4B | 914 | | | | | | | | | -0.4 | -7.83 | 0.25 | -2.45 |
| 214 | SNORD59B | 134 | 7.97E+10 | -4.49E+11 | -5.49E+13 | -2.31E+13 | 0.56 | -0.01 | -0.87 | -0.65 | | | | |
| 215 | SPTA1 | 620 | | | | | -2.13E+10 | -4.78E+10 | -1.06E+11 | -3.12E+10 | -6.14E+10 | 2.29E+14 | -1.06E+11 | 7.64E+12 |
| 216 | THBS1 | 844 | -0.78 | 1.25 | 0.83 | 1.04 | | | | | 0.9 | -6.84 | -0.79 | -2.8 |
| 217 | TLR5 | 53 | | | | | -0.79 | 1.29 | -0.36 | 0.06 | | | | |
| 218 | TMEM158 | 1153 | -3.99E+09 | -8.30E+07 | -1.67E+11 | -1.01E+11 | -1.76E+10 | 9.74E+09 | -1.35E+11 | -9.90E+10 | 1.2 | -5.74 | -1.49 | -2.91 |
| 219 | TMEM175A | 1337 | | | | | -9.29E+10 | 3.08E+09 | -1.08E+10 | -7.33E+09 | 1.18 | -8.72 | -0.4 | -3.17 |
| 220 | TMEM175B | 1363 | | | | | | | | | | | | |
| 221 | TNFRSF9 | 602 | | | | | | | | | 0.47 | -5.93 | -0.25 | -2.14 |
| 222 | TREML1 | 1288 | | | | | -6.27E+10 | 8.15E+09 | -2.24E+11 | -1.66E+11 | | | | |
| 223 | TRNN | 7, 20, 497 | -5.16E+12 | -2.01E+12 | -7.75E+13 | -4.73E+13 | | | | | | | | |
| 224 | TSTA3 | 471 | -7.01E+11 | -1.98E+12 | -8.75E+12 | -6.03E+12 | -3.35E+08 | -9.05E+07 | -9.43E+08 | -7.30E+08 | -3.47E+12 | -2.16E+12 | -1.06E+13 | -7.76E+12 |
| 225 | TUBB2A | 1244, 1245, 1277 | -0.7 | 1.05 | -0.51 | 0.27 | | | | | | | | |
| 226 | U38B | 1677 | | | | | | | | | 1.87 | -5.93 | -0.28 | -2.15 |
| 227 | USP32P1 | 912 | | | | | | | | | 0.76 | -6.32 | -0.43 | -2.4 |
| 228 | YME1L1 | 765, 771, 768, 769, 764, 760, 762, 766, 770, 777, 781, 785, 794, 789, 791 | -6.99E+10 | -1.70E+10 | 1.19E+11 | 6.44E+10 | | | | | 0.46 | -6.9 | -0.25 | -2.47 |

Fig. 10K

| Fig. 9 row | RNA | SEQ ID | log2 C/B ||||log2 D/B ||||log2 D/C ||||
|---|---|---|---|---|---|---|---|---|---|---|---|---|---|---|
| | | | Alnorm | Alnu | Alslow | Alnotnorm | Alnorm | Alnu | Alslow | Alnotnorm | Alnorm | Alnu | Alslow | Alnotnorm |
| 1 | A2M | 722 | | | | | -0.26 | -10.58 | -0.37 | -7.17 | 0.76 | -5.82 | -1.1 | -2.87 |
| 2 | A2M-AS1 | 703 | | | | | 0.19 | -9.82 | 0.71 | -6.31 | 0.62 | -5.08 | 0.16 | -1.81 |
| 3 | A2MP1 | 724 | | | | | | | | | | | | |
| 4 | ADGRE1 | 966 | | | | | 0.06 | -14.5 | 0.49 | -9.5 | 0.57 | -9.03 | -0.75 | -3.85 |
| 5 | AIF1 | 1, 408, 513, 515 | | | | | | | | | | | | |
| 6 | ANKRD22 | 75 | | | | | | | | | 0.56 | -0.88 | -2.06 | -1.62 |
| 7 | ANKRD36B | 1074 | | | | | 0.57 | -14.17 | 0.85 | -9.16 | 0.7 | -8.16 | 0.24 | -2.91 |
| 8 | ANPEP | 862 | | | | | 0.3 | -15.82 | 0.12 | -10.5 | 0.64 | -9.66 | -1.01 | -4.28 |
| 9 | ANXA3 | 348 | | | | | | | | | | | | |
| 10 | ARG1 | 413 | | | | | | | | | | | | |
| 11 | ARPP19 | 388 | | | | | 0.33 | 1.06 | -2.86 | -0.25 | | | | |
| 12 | ATG9A | 1080 | | | | | 0.01 | -15.54 | 0.35 | -10.25 | 0.46 | -8.97 | -0.46 | -3.65 |
| 13 | C4BPA | 598 | | | | | -0.12 | -11.59 | 0.44 | -7.58 | 0.51 | -6.72 | -1.23 | -3.29 |
| 14 | CASP5 | 103, 698 | | | | | 0.47 | -12.33 | 0.38 | -8.09 | 0.56 | -8.62 | -0.77 | -3.71 |
| 15 | CCDC144A | 910, 911 | | | | | | | | | 1.63 | 0 | -9.09 | -5.68 |
| 16 | CCR7 | 934 | | | | | 0.37 | -14.61 | 0.56 | -9.55 | 0.67 | -8.91 | -0.02 | -3.36 |
| 17 | CD27 | 700 | | | | | 0.08 | -14.07 | 0.32 | -9.27 | 0.08 | -8 | -0.05 | -3.03 |
| 18 | CE81 | 885 | | | | | 0.11 | -12.59 | 0.33 | -8.28 | 0.99 | -8.25 | -1.37 | -3.95 |
| 19 | CHRM3-AS2 | 634 | | | | | 0.57 | -13.86 | 0.52 | -9.07 | 0.56 | -7.79 | 0.26 | -2.76 |
| 20 | CLEC1B | 124, 725 | | | | | -0.08 | -13.54 | -0.16 | -9.14 | 0.07 | -8.51 | -0.87 | -3.74 |
| 21 | CLEC4D | 109, 702 | | | | | | | | | | | | |
| 22 | CLEC4E | 721 | | | | | -0.08 | -15.1 | 0.38 | -9.94 | 0.45 | -9.49 | -0.91 | -4.13 |
| 23 | CLIC2 | 512 | | | | | | | | | | | | |
| 24 | CLU | 1382 | | | | | 0.14 | -15.91 | -0.03 | -11.29 | 0.23 | -10.57 | -0.98 | -4.58 |
| 25 | CMTM2 | 868 | -7.15E+06 | -6.48E+06 | 3.32E+07 | 2.33E+07 | -1.97E+11 | 3.14E+15 | -2.27E+11 | 2.06E+15 | -6.82E+10 | 2.06E+15 | -9.02E+10 | 7.85E+14 |
| 26 | COX7B | 1431 | | | | | -0.52 | -11.05 | 0.19 | -7.3 | 0.63 | -7.39 | -1.06 | -3.44 |
| 27 | CR1 | 24, 599 | | | | | 0.16 | -15.16 | 0.33 | -9.99 | 0.53 | -9.54 | -1.23 | -4.35 |
| 28 | CSNK1A1L | 753 | | | | | 0.57 | -14.24 | 0.78 | -9.23 | 0.38 | -8.43 | -0.39 | -3.41 |
| 29 | CST7 | 298 | | | | | -0.12 | 1.42 | -1.37 | 0.48 | | | | |
| 30 | DSC2 | 962 | | | | | 0.3 | -14.52 | 0.61 | -9.48 | 0.56 | -9.08 | -1.16 | -4.13 |
| 31 | DYSF | 1024 | | | | | 0.1 | -15.09 | 0.41 | -9.92 | 0.7 | -9.24 | -1.09 | -4.15 |
| 32 | EGF | 351 | -0.7 | -0.99 | 0.81 | 0.44 | -0.07 | -14.2 | -0.16 | -9.52 | 0.34 | -8.62 | -1.16 | -2.97 |
| 33 | EIF4B | 132 | | | | | | | | | | | | |
| 34 | F5 | 46, 624 | | | | | 0.33 | -13.94 | 0.25 | -9.21 | 0.47 | -8.53 | -1.14 | -3.91 |
| 35 | F8A1 | 1427 | | | | | 0.77 | -14.36 | -0.09 | -9.6 | 0.74 | -8.78 | -0.42 | -3.56 |
| 36 | FAM83A | 459 | 0 | -1.51 | -8.25 | -6.57 | | | | | -1.70E+09 | -8.47E+08 | 5.29E+09 | 2.99E+09 |
| 37 | FLJ45950 | 106 | | | | | 0.88 | 1.91 | -5.92 | -0.7 | | | | |
| 38 | GCNT4 | 1228 | | | | | 0.47 | -13.49 | 0.37 | -8.87 | 0.61 | -8.05 | -0.15 | -3.11 |
| 39 | GPR162 | 701 | | | | | 0.4 | -13.16 | 0.71 | -8.53 | 0.65 | -7.92 | -0.36 | -3.19 |
| 40 | GRIK1-AS2 | 1098 | -177 | 0 | 1520 | 1140 | | | | | 2.50E+06 | 3.37E+06 | -4.98E+06 | -1.85E+06 |
| 41 | GYG1 | 314 | | | | | 0.07 | -14.91 | 0.28 | -9.85 | 0.59 | -9.13 | -0.68 | -3.85 |

Fig. 10L

| Fig. 9 row | RNA | SEQ ID | log2 C/B Anorm | log2 C/B Alnu | log2 C/B Alslow | log2 C/B Alnotnorm | log2 D/B Anorm | log2 D/B Alnu | log2 D/B Alslow | log2 D/B Alnotnorm | log2 D/C Anorm | log2 D/C Alnu | log2 D/C Alslow | log2 D/C Alnotnorm |
|---|---|---|---|---|---|---|---|---|---|---|---|---|---|---|
| 42 | GZMH | 814 | | | | | -0.44 | -11.66 | 0.03 | -7.77 | 1.23 | -6.96 | -0.13 | -2.72 |
| 43 | H1F0 | 299 | -2.04E+07 | -2.54E+08 | -1.11E+08 | -1.47E+08 | | | | | | | | |
| 44 | H6Q1 | 867 | | | | | -0.78 | -16.56 | -0.04 | -11.06 | -0.15 | -9.2 | -0.51 | -3.77 |
| 45 | HIST1H2BG | 1281 | -0.53 | -0.83 | 0.95 | 0.51 | 0.01 | -13.9 | -0.22 | -9.34 | 0.42 | -6.15 | -0.76 | -3.53 |
| 46 | HIST1H3I | 1283 | -0.18 | -1.27 | 1.55 | 0.92 | -0.08 | -12.49 | 0.04 | -8.21 | 0.36 | -7.76 | -0.13 | -2.99 |
| 47 | HLA-DRB1 | 1286 | | | | | 0.13 | -15.91 | 0.45 | -10.48 | 0.53 | -9.67 | -0.24 | -3.77 |
| 48 | HMBS | 89, 677 | | | | | | | | | | | | |
| 49 | let-7a-5p | 516 | | | | | -0.03 | -15.39 | 0.23 | -10.18 | -1.05 | -9.72 | -0.52 | -3.97 |
| 50 | let-7d-3p | 1499 | | | | | -1.15 | -13.37 | 1.1 | -6.55 | -0.01 | -14 | 0.28 | -5.08 |
| 51 | let-7e-5p | 517 | 2.16E+12 | -1.33E+13 | 3.76E+12 | -5.11E+11 | 0.1 | -18.46 | 0.62 | -10.77 | -0.9 | -10.31 | -0.5 | -4.18 |
| 52 | let-7f-5p | 518 | | | | | 1.07E+10 | -3.55E+10 | -2.24E+10 | -3.12E+10 | | | | |
| 53 | miR-100-5p | 1830 | | | | | 0.26 | -11.22 | 0.92 | -7.17 | -0.68 | -6.91 | 0.58 | -2.23 |
| 54 | miR-106a-5p | 519 | | | | | 0.94 | -6.14 | 2.09 | -3.39 | 0.65 | -2.93 | -0.22 | -1.24 |
| 55 | miR-122-5p | 1831 | | | | | | | | | | | | |
| 56 | miR-1228-5p | 520 | 8.02E+07 | 0 | -7.12E+08 | -5.34E+08 | -6.12E+08 | 8.52E+06 | 1.75E+09 | 5.89E+08 | | | | |
| 57 | miR-1247-3p | 1499 | | | | | | | | | -4.66 | -261.23 | 0 | -97.96 |
| 58 | miR-1255b-5p | 522 | | | | | 0.55 | -3.84 | 2.15 | -1.85 | | | | |
| 59 | miR-125b-5p | 1500 | | | | | -0.42 | -12.62 | 0.7 | -8.18 | -0.42 | -12.01 | 0.08 | -4.45 |
| 60 | miR-126-3p | 1501 | | | | | 0.53 | -16.99 | 0.87 | -11.04 | -0.2 | -10.76 | -0.3 | -4.22 |
| 61 | miR-1270 | 523 | | | | | 0.22 | -4.84 | 2.41 | -2.42 | -2.03E+09 | -8.41E+09 | 2.31E+10 | 1.13E+10 |
| 62 | miR-1303 | 1508 | 0.61 | 5.77 | 1.36 | 2.47 | | | | | -0.59 | -7.15 | 1.19 | -1.94 |
| 63 | miR-134-5p | 1512 | -4.21E+07 | 1.29E+09 | -1.14E+07 | 3.13E+08 | -1.23 | -12.41 | 2.2 | -7.54 | 0.02 | -10.6 | 2.29 | -2.53 |
| 64 | miR-143-3p | 1513 | | | | | 2.63 | -13.18 | -0.02 | -8.79 | 0.44 | -12.6 | -0.61 | -5.11 |
| 65 | miR-144-5p | 1514 | | | | | 1.56 | -14.95 | 0.9 | -9.67 | 0.13 | -10.41 | 0.02 | -3.89 |
| 66 | miR-146a-5p | 1832 | -4.00E+10 | -7.00E+12 | 6.57E+11 | -1.26E+12 | 0.27 | -5.61 | 1.05 | -3.39 | 0.14 | -3.77 | 0.29 | -1.23 |
| 67 | miR-146b-5p | 1515 | 2.15E+11 | -5.25E+12 | 4.08E+11 | -1.01E+12 | 0.05 | -15.72 | 0.41 | -10.34 | -0.66 | -9.45 | -0.13 | -3.66 |
| 68 | miR-148a-3p | 1833 | 5.51E+10 | -1.32E+12 | -1.35E+11 | -4.30E+11 | 0.05 | -14.99 | 0.49 | -9.83 | -0.61 | -12.13 | -0.43 | -5.19 |
| 69 | miR-151a-3p | 525 | | | | | 0.13 | -3.53 | 0.72 | -2.11 | | | | |
| 70 | miR-154-5p | 1517 | -0.39 | -29.36 | 8.17 | -1.21 | | | | | | | | |
| 71 | miR-155-5p | 526 | | | | | 1.54 | -12.91 | 1.03 | -8.27 | 1.03 | -8.27 | 1.13 | -2.39 |
| 72 | miR-17-5p | 527 | | | | | 0.88 | -6.04 | 1.92 | -3.38 | 0.64 | -2.95 | -0.31 | -1.3 |
| 73 | miR-182-3p | 528 | 2.00E+06 | 1.63E+08 | 6.14E+07 | 8.68E+07 | | | | | | | | |
| 74 | miR-18a-5p | 529 | | | | | 1.56 | -3.25 | -1.29 | -2.6 | | | | |
| 75 | miR-196a-5p | 1522 | -0.19 | 4.78 | -0.35 | 0.93 | 0.22 | -8.37 | 0.55 | -5.39 | 0.55 | -7.51 | 0.44 | -2.54 |
| 76 | miR-196b-5p | 1523 | | | | | 0.53 | -12.6 | 0.46 | -8.25 | -0.7 | -8.15 | -0.24 | -3.21 |
| 77 | miR-1973 | 1524 | | | | | | | | | | | | |
| 78 | miR-1976 | 1526 | | | | | -0.03 | -13.75 | 0.99 | -8.84 | 0.08 | -14.63 | 0.37 | -5.26 |
| 79 | miR-199a-5p | 531 | | | | | 0.71 | -5.5 | 0.93 | -3.34 | | | | |
| 80 | miR-19b-3p | 1527 | 8.75E+12 | -1.62E+14 | 2.67E+13 | -2.06E+13 | 0.53 | -18.1 | 0.95 | -11.89 | -0.61 | -11.55 | 0.76 | -3.86 |
| 81 | miR-202-3p | 1528 | | | | | | | | | -24800 | 15900 | 40200 | 31100 |
| 82 | miR-20a-5p | 1529 | | | | | 0.55 | -17.44 | 1.04 | -11.28 | -0.78 | -10.79 | -0.63 | -4.44 |
| 83 | miR-21-5p | 1834 | | | | | 1 | -15.65 | 0.01 | -10.43 | -0.49 | -9.54 | 0.09 | -3.52 |

Fig. 10M

| Fig. 9 row | RNA | SEQ ID | log2 C/B | | | | log2 D/B | | | | log2 D/C | | | |
|---|---|---|---|---|---|---|---|---|---|---|---|---|---|---|
| | | | Alnorm | Alnu | Alslow | Alnotnorm | Alnorm | Alnu | Alslow | Alnotnorm | Alnorm | Alnu | Alslow | Alnotnorm |
| 84 | miR-221-3p | 533 | | | | | 0.84 | -1.63 | -2.07 | -1.91 | 0.49 | -2.91 | 0.03 | -1.07 |
| 85 | miR-223-3p | 534 | | | | | -0.1 | -17.88 | 0.65 | -11.71 | -0.45 | -12.08 | 0.21 | -4.4 |
| 86 | miR-23a-3p | 535 | | | | | -1.44E+10 | -1.79E+11 | 0 | -1.19E+11 | | | | |
| 87 | miR-24-3p | 1835 | 9.99E+11 | -2.79E+13 | 9.80E+12 | -2.55E+12 | 0.19 | -17.04 | 0.73 | -11.12 | -0.81 | -10.58 | 0.04 | -3.94 |
| 88 | miR-25-3p | 1836 | 4.30E+12 | -2.62E+13 | 1.16E+13 | 2.18E+12 | -0.73 | -16.47 | 1 | -10.65 | -1.48 | -10.25 | 0.32 | -3.65 |
| 89 | miR-25-5p | 1531 | 746 | -22.9 | 7040 | 5280 | | | | | | | | |
| 90 | miR-27a-3p | 539, 540 | | | | | 0.53 | -1.39 | -1.78 | -1.52 | 0.34 | -2.79 | 0.29 | -0.87 |
| 91 | miR-27b-3p | 541 | | | | | 0.43 | -4.83 | 1.11 | -2.59 | 1.06E+10 | -6.50E+10 | 1.21E+10 | -1.69E+10 |
| 92 | miR-28a-3p | 542 | -4.73E+10 | -2.71E+12 | 4.28E+11 | -3.55E+11 | 0.3 | -15.86 | 0.75 | -10.32 | -0.81 | -8.94 | 0.62 | -2.96 |
| 93 | miR-29b-3p | 1534 | | | | | 144000 | -514000 | -391000 | -473000 | | | | |
| 94 | miR-29c-3p | 1535 | -6.50E+10 | -2.97E+12 | -2.36E+11 | -9.20E+11 | -0.36 | -15.16 | 0.23 | -10.03 | -0.69 | -13.5 | -0.27 | -5.22 |
| 95 | miR-29c-5p | 1536 | | | | | -0.55 | -11.03 | 1.43 | -6.86 | -0.21 | -11.3 | 0.87 | -3.68 |
| 98 | miR-3117-3p | 1539 | | | | | | | | | | | | |
| 96 | miR-31-3p | 1837 | | | | | 4250 | -5750 | 56700 | 15100 | -0.42 | -0.31 | 1.08 | 0.56 |
| 99 | miR-3156-5p | 1542 | | | | | 5.15 | -17.5 | -0.78 | -11.9 | -119000 | -109000 | 132000 | 41500 |
| 97 | miR-31-5p | 1543 | | | | | 3.34 | -12.24 | 1.01 | -7.82 | | | | |
| 100 | miR-317b | 1544 | | | | | | | | | -6.29 | -5.05 | 4.35 | 0.83 |
| 101 | miR-323a-3p | 1546 | -1.93E+09 | -3.22E+11 | 1.52E+10 | -6.91E+10 | -0.03 | -6.83 | 0.24 | -4.48 | -0.14 | -3.52 | 0.51 | -1 |
| 102 | miR-323b-3p | 1547 | -2.04 | -0.53 | 6.12 | 4.46 | | | | | -0.97 | -6.9 | 5.34 | 0.75 |
| 103 | miR-329-3p | 1548 | 1.97E+08 | -8.34E+09 | 2.72E+08 | -1.88E+09 | 1.07E+07 | -5.94E+09 | 6.37E+08 | -3.75E+09 | -2.08 | -3.1 | 6.66 | 3 |
| 104 | miR-335-5p | 543 | | | | | 0.44 | 0.63 | -2.74 | -0.49 | | | | |
| 105 | miR-3613-3p | 1551 | | | | | -1.70E+08 | -6.54E+07 | 1.04E+09 | 3.08E+08 | | | | |
| 106 | miR-3613-5p | 1552 | | | | | 1.19E+08 | -1.70E+09 | 7.07E+09 | 1.22E+09 | | | | |
| 107 | miR-3667-5p | 1555 | | | | | -1.83 | -13.76 | 0.95 | -8.86 | 0.44 | -13.5 | 0.54 | -4.72 |
| 108 | miR-374b-5p | 1561 | | | | | -0.26 | -12.42 | 0.38 | -8.15 | -0.39 | -9.52 | -0.72 | -4.02 |
| 109 | miR-376a-3p | 1562 | 139000 | -2.66E+06 | -69300 | -716000 | -164000 | -2.51E+06 | 385000 | -1.54E+06 | | | | |
| 110 | miR-379-5p | 1565 | | | | | 1.78E+09 | -1.33E+10 | 7.43E+09 | -6.36E+09 | | | | |
| 111 | miR-4284 | 1575 | | | | | 0.7 | -4.4 | 1.03 | -2.59 | | | | |
| 112 | miR-431-5p | 1576 | 6.46E+08 | -1.84E+11 | -1.18E+08 | -4.62E+10 | 3.52 | -22.29 | 0 | -14.86 | -1.47E+09 | -1.50E+10 | -1.59E+08 | -6.72E+09 |
| 113 | miR-4435 | 1579 | | | | | | | | | | | | |
| 114 | miR-4485 | 1582 | | | | | -1.12E+09 | 2.34E+08 | 8.28E+09 | 2.92E+09 | | | | |
| 115 | miR-4525 | 1584 | | | | | | | | | -1.76 | 5.61 | 6.51 | 6.17 |
| 116 | miR-4668-5p | 1585 | 1.79 | 11.84 | 0 | 2.96 | | | | | | | | |
| 117 | miR-4797-5p | 1598 | -5.89E+06 | -9.32E+07 | -4.12E+07 | -5.42E+07 | -1.48 | -6.93 | -15.53 | -9.8 | | | | |
| 118 | miR-485-3p | 1599 | 3760 | -1.10E+07 | 541000 | -2.35E+06 | 728000 | -8.65E+06 | 1540 | -5.77E+06 | -0.93 | -7.63 | 2.08 | -1.57 |
| 119 | miR-487a-3p | 1600 | -271 | 1840 | 183 | 596 | | | | | | | | |
| 120 | miR-487b-3p | 1601 | -1.93E+09 | -5.66E+10 | 3.08E+09 | -1.18E+10 | -9.00E+07 | -6.50E+10 | 3.98E+09 | -4.20E+10 | -1.63E+09 | -2.08E+10 | 1.29E+09 | -7.01E+09 |
| 121 | miR-495-3p | 1605 | 3.33E+09 | -4.06E+10 | 2.56E+08 | -9.96E+09 | -0.09 | -7.71 | -0.41 | -5.28 | 2.05E+08 | -2.45E+10 | 1.55E+09 | -7.96E+09 |
| 122 | miR-504-5p | 548 | 0.17 | -1.42 | 1.94 | 1.1 | -0.58 | 1.16 | 3.27 | 1.86 | | | | |
| 123 | miR-505-3p | 1607 | | | | | 0.43 | -22.7 | 0.19 | -15.1 | | | | |
| 124 | miR-5195-3p | 1608 | 0.11 | -4.59 | -0.12 | -1.24 | 0.63 | -7.34 | -0.78 | -5.15 | | | | |
| 125 | miR-543 | 1609 | | | | | -1 | -12.61 | -0.31 | -8.51 | -0.78 | -12.1 | 0.3 | -4.04 |

Fig. 10N

| Fig. 9 row | RNA | SEQ ID | log2 C/B | | | | log2 D/B | | | | log2 D/C | | | |
|---|---|---|---|---|---|---|---|---|---|---|---|---|---|---|
| | | | Alnorm | Alnu | Alslow | Alnotnorm | Alnorm | Alnu | Alslow | Alnotnorm | Alnorm | Alnu | Alslow | Alnotnorm |
| 126 | miR-548aa | 1610 | 1.11E+11 | -4.02E+12 | 8.13E+11 | -3.96E+11 | 0.16 | -15.88 | 1.42 | -10.12 | -0.82 | -9.78 | 0.89 | -3.11 |
| 127 | miR-551a | 549 | -2.33E+08 | -2.23E+09 | 2.23E+08 | -3.91E+08 | 8.73E+07 | -1.23E+09 | 1.54E+09 | -3.06E+09 | | | | |
| 128 | miR-584-5p | 550 | | | | | -0.05 | -3.78 | 1.95 | -1.87 | -2.39E+10 | -7.16E+09 | 1.12E+11 | 6.75E+10 |
| 129 | miR-589-5p | 551 | | | | | 0.68 | -6.12 | 2.42 | -3.27 | | | | |
| 130 | miR-654-3p | 1627 | | | | | 9.88E+08 | -2.53E+10 | 3.96E+09 | -1.57E+10 | | | | |
| 131 | miR-664a-5p | 552 | 0.21 | -0.59 | -7.6 | -5.95 | 1.27 | -8.57 | -3.65 | -6.92 | | | | |
| 132 | miR-6726-3p | 1628 | | | | | | | | | | | | |
| 133 | miR-6770-5p | 1637 | | | | | | | | | | | | |
| 134 | miR-6777-3p | 1640 | -0.72 | 3.29 | 0.73 | 1.37 | | | | | 0.91 | -2.07 | 1.74 | 0.31 |
| 135 | miR-6818-5p | 1643 | | | | | 91 | -13100 | 30300 | 1390 | | | | |
| 136 | miR-6820-3p | 1645 | -1.84E+09 | 6.99E+09 | 1.32E+10 | 1.16E+10 | 0.04 | -9.95 | 2.8 | -5.71 | | | | |
| 137 | miR-6840-3p | 1648 | 3.99E+12 | -8.92E+13 | 1.05E+12 | -2.15E+13 | -0.13 | -3.48 | -1.56 | -2.87 | | | | |
| 138 | miR-6855-3p | 1649 | | | | | | | | | 1.21 | -5.36 | 2.41 | -0.51 |
| 139 | miR-6879-3p | 1652 | | | | | -0.21 | -11.55 | 1.59 | -7.04 | -0.54 | -7.65 | 1.33 | -2.03 |
| 140 | miR-7-5p | 553, 1656 | | | | | 1.22 | -13.21 | 0.1 | -8.77 | -0.64 | -7.9 | 0.51 | -2.54 |
| 141 | miR-7641 | 1657 | | | | | -1 | -14.29 | 0.67 | -9.2 | -0.6 | -12.2 | 0.51 | -4.26 |
| 142 | miR-7975 | 1662 | | | | | -0.59 | -11.87 | 1.18 | -7.52 | -1.05 | -7.33 | 0.39 | -2.5 |
| 143 | miR-93-5p | 556 | | | | | 0.75 | -2.25 | -0.03 | -1.51 | 0.52 | -3.34 | 0.22 | -1.11 |
| 144 | miR-98-5p | 1665 | | | | | 6.19 | -9.48 | -4 | -7.65 | | | | |
| 145 | HSPA9 | 400 | | | | | | | | | 0.24 | -0.04 | -0.31 | -0.21 |
| 146 | HSPD1 | 283 | | | | | | | | | | | | |
| 147 | IFI44 | 573 | | | | | 0.07 | -12.36 | -0.49 | -8.4 | 0.83 | -8.97 | -1.54 | -4.7 |
| 148 | IFI44L | 572 | | | | | -0.08 | -13.41 | -0.07 | -8.86 | 0.75 | -10.69 | -1.21 | -4.76 |
| 149 | IFI6 | 609 | | | | | -0.05 | -15.61 | 0.4 | -10.27 | 0.56 | -11.11 | -0.82 | -4.58 |
| 150 | IFIT1 | 655 | | | | | 0.21 | -14.73 | -0.19 | -9.88 | 0.59 | -11.89 | -1.77 | -5.41 |
| 151 | IFIT1B | 64, 654 | | | | | | | | | | | | |
| 152 | IFIT2 | 652 | | | | | 0.43 | -14.75 | -0.51 | -10.01 | 0.6 | -10.49 | -1.75 | -5.08 |
| 153 | IFIT3 | 653 | | | | | 0.09 | -15.32 | -0.2 | -10.28 | 0.54 | -11.07 | -1.59 | -5.14 |
| 154 | IFIT5 | 656 | | | | | -0.06 | -12.42 | -0.2 | -8.34 | 0.59 | -8.69 | -1.42 | -4.15 |
| 155 | IFITM3 | 682 | 3.29 | -26.59 | 1.07 | -5.87 | | | | | | | | |
| 156 | IFNA16 | 1406 | | | | | | | | | | | | |
| 157 | IGHA1 | 824 | | | | | 0.36 | -16.23 | -0.38 | -10.94 | 0.25 | -8.98 | -1.22 | -4.13 |
| 158 | IGKC | 1073, 1071, 1070, 1069, 1068, 1063 | 0 | 0 | 8.89 | 6.66 | 2.57 | -13.83 | -25.07 | -17.58 | 9.77E+09 | 9.64E+10 | 1.01E+08 | 3.68E+10 |

Fig. 10O

| Fig. 9 row | RNA | SEQ ID | log2 C/B | | | | log2 D/B | | | | log2 D/C | | | |
|---|---|---|---|---|---|---|---|---|---|---|---|---|---|---|
| | | | Anorm | Au | Aslow | Anotnorm | Anorm | Au | Aslow | Anotnorm | Anorm | Au | Aslow | Anotnorm |
| 159 | IGLC1 | 1109, 1110, 1111, 1114, 1115 | | | | | 0.67 | -11.06 | 0.35 | -7.28 | 0.47 | -5.79 | 0.52 | -1.85 |
| 160 | IL2RB | 2 | | | | | | | | | | | | |
| 161 | IL5RA | 1151 | | | | | 0.23 | -13.74 | 1.26 | -8.74 | 0.45 | -8.41 | -0.59 | -3.52 |
| 162 | IRF8 | 194 | | | | | 7.89 | -12.24 | -23.44 | -15.98 | 5.36 | -10.5 | -7.27 | -6.61 |
| 163 | ITGA2B | 215, 938 | | | | | 0.19 | -16.17 | 0.21 | -10.71 | 0.23 | -10.26 | -1.62 | -4.86 |
| 164 | ITGB3 | 918 | | | | | 0.42 | -16.88 | 0.23 | -11.18 | 0.27 | -10.77 | -1.52 | -4.98 |
| 165 | KCNJ15 | 1100 | | | | | 0.52 | -15.58 | 0.79 | -10.12 | 0.29 | -9.4 | -1.23 | -4.29 |
| 166 | KIF13A | 1279 | | | | | 0.38 | -14.09 | 0.31 | -9.29 | 0.71 | -8.29 | -1.08 | -3.77 |
| 167 | KIF1B | 562 | | | | | 0.38 | -14.23 | 0.61 | -9.28 | 0.69 | -8.52 | -1.04 | -3.85 |
| 168 | KLK12 | 1004 | | | | | -7.64E+08 | -8.19E+10 | 0 | -5.44E+10 | | | | |
| 169 | LDHB | 126 | | | | | | | | | 0.55 | 0.73 | -1.37 | -0.58 |
| 170 | LEF1 | 1201 | | | | | 0.66 | -15.26 | 0.73 | -9.93 | 0.68 | -9.21 | -0.31 | -3.65 |
| 171 | LGALS2 | 1126 | | | | | 0.1 | -13.39 | 0.14 | -8.88 | 0.49 | -8.16 | -0.67 | -3.48 |
| 172 | LOC440300 | 850 | | | | | | | | | | | | |
| 173 | LOC646214 | 855 | | | | | 0.49 | -3.32 | 0.45 | -2.06 | 0.81 | -1.63 | 0.24 | -0.46 |
| 174 | MANSC1 | 729 | | | | | 0.21 | -13.94 | 0.61 | -9.09 | 0.53 | -8.13 | -0.99 | -3.67 |
| 175 | MFSD9 | 1075 | | | | | -0.06 | -13.85 | 0 | -9.23 | 0.56 | -8.18 | -0.59 | -3.44 |
| 176 | pre-miR29a | 449 | | | | | | | | | | | | |
| 177 | MMP9 | 1087 | | | | | 0.17 | -15.24 | -0.59 | -10.36 | 0.53 | -9.02 | -1.79 | -4.5 |
| 178 | MT1E | 189 | | | | | 0 | 1.9 | -3.62 | 0.06 | | | | |
| 179 | MT1X | 191 | | | | | 0.32 | 0.92 | -2.06 | -0.08 | | | | |
| 180 | MXD3 | 270 | | | | | 0.19 | 0.67 | -1.64 | -0.1 | | | | |
| 181 | MYL4 | 917 | | | | | -0.46 | -15.93 | 0.23 | -10.54 | -0.06 | -8.85 | -0.73 | -3.78 |
| 182 | NDUFA2 | 401 | | | | | | | | | | | | |
| 183 | NFATC1 | 961 | | | | | 0.52 | -13.93 | 0.32 | -9.18 | 0.8 | -8.24 | -0.21 | -3.22 |
| 184 | NFATC2 | 4 | | | | | | | | | | | | |
| 185 | NLRC4 | 1054 | | | | | 0.17 | -14.57 | 0.1 | -8.68 | 0.73 | -9.04 | -0.89 | -3.96 |
| 186 | NOTCH3 | 996 | | | | | 0.25 | -10.47 | -0.14 | -7.02 | 0.84 | -6.23 | -0.97 | -2.94 |
| 187 | OMG | 931 | | | | | 0.19 | -13.03 | 0.55 | -8.5 | 0.65 | -7.65 | -0.29 | -3.05 |
| 188 | PAQR4 | 9, 563 | | | | | 0.1 | -15.83 | 0.28 | -10.47 | 0.56 | -9.28 | -1.01 | -4.11 |
| 189 | PDIA3P | 582 | | | | | -0.36 | -12.72 | 0.33 | -8.37 | 1.52 | -7.85 | -0.58 | -3.23 |
| 190 | PECAM1 | 1838 | | | | | | | | | -0.08 | 0.16 | -0.51 | -0.26 |
| 191 | PET100 | 968 | | | | | 0.28 | -13.27 | -0.21 | -8.91 | 0.53 | -8.06 | -0.86 | -3.57 |
| 192 | PI3 | 1086 | 0.01 | -0.28 | 1.7 | 1.21 | 0.4 | -15.35 | 1.48 | -9.74 | 0.51 | -9.08 | 0.25 | -3.25 |
| 193 | PPDPF | 291 | | | | | -1.10E+08 | -2.12E+08 | -6.13E+08 | -3.46E+08 | | | | |
| 194 | PRKXP1 | 864 | | | | | 0.98 | -12.82 | 0.19 | -8.48 | 0.95 | -7.9 | -0.29 | -3.14 |
| 195 | PROS1 | 1154 | | | | | -0.33 | -14.29 | 0.19 | -9.47 | 0.12 | -8.85 | -1.04 | -3.97 |

Fig. 10P

| Fig. 9 row | RNA | SEQ ID | log2 C/B Anorm | log2 C/B Alnu | log2 C/B Alslow | log2 C/B Anotnorm | log2 D/B Anorm | log2 D/B Alnu | log2 D/B Alslow | log2 D/B Anotnorm | log2 D/C Anorm | log2 D/C Alnu | log2 D/C Alslow | log2 D/C Anotnorm |
|---|---|---|---|---|---|---|---|---|---|---|---|---|---|---|
| 196 | PYGL | 164, 815 | | | | | 0.36 | -15.82 | 0.29 | -10.45 | 0.44 | -9.59 | -1.06 | -4.3 |
| 197 | RAB39A | 579 | | | | | -0.01 | -11.45 | -0.08 | -7.65 | 0.74 | -6.6 | -0.8 | -2.98 |
| 198 | RAD23A | 239 | | | | | | | | | | | | |
| 199 | RBBP8 | 954 | | | | | -0.47 | -13.73 | 0.21 | -9.08 | 0.07 | -8.18 | -0.72 | -3.52 |
| 200 | ROPN1L | 371 | | | | | | | | | | | | |
| 201 | RPS15 | 279 | | | | | 0.03 | 1.48 | -1.72 | 0.41 | | | | |
| 202 | RPS27 | 347 | | | | | -0.13 | 3.05 | -1.51 | 1.53 | | | | |
| 203 | RUNDC3A | 915 | | | | | -0.68 | -15.64 | 0.43 | -10.95 | -0.14 | -9.09 | -0.41 | -3.67 |
| 204 | S100A12 | 5, 618 | -3.22E+10 | -3.19E+12 | 3.50E+10 | -7.70E+11 | | | | | 0.07 | -0.06 | -1.18 | -0.76 |
| 205 | S100P | 344 | | | | | | | | | | | | |
| 206 | SELP | 825 | | | | | -2.5 | -27.87 | -0.18 | -18.64 | -3.27E+09 | 3.50E+14 | -2.04E+10 | 1.91E+14 |
| 207 | SMAD4 | 958 | | | | | 0.28 | -14.88 | 0.37 | -9.8 | 0.64 | -8.88 | -0.51 | -3.65 |
| 208 | SMN1 | 1216 | 0.04 | -0.35 | 0.1 | -0.01 | 0.37 | -13.85 | 0.59 | -9.04 | 0.68 | -7.98 | 0 | -2.99 |
| 209 | SNORA14A | 1318 | | | | | -0.51 | -13.61 | 0.21 | -9.01 | 0.4 | -8.03 | 0.4 | -2.77 |
| 210 | SNORD13 | 228 | | | | | | | | | | | | |
| 211 | SNORD14E | 104 | | | | | | | | | | | | |
| 212 | SNORD25 | 6, 99 | | | | | 2.25E+09 | 3.16E+10 | 4.51E+08 | 2.12E+10 | | | | |
| 213 | SNORD49 | 914 | | | | | 0.4 | -15.52 | 0.4 | -10.88 | -0.25 | -8.92 | 0.07 | -3.67 |
| 214 | SNORD59B | 134 | | | | | | | | | | | | |
| 215 | SPTA1 | 620 | | | | | -0.66 | -14.8 | 0.58 | -9.67 | -0.05 | -7.67 | -1.42 | -3.76 |
| 216 | THBS1 | 844 | | | | | 0.39 | -15.7 | -0.16 | -10.52 | 0.47 | -9.01 | -1.54 | -4.68 |
| 217 | TLR5 | 53 | | | | | | | | | 0.43 | -0.27 | -0.9 | -0.66 |
| 218 | TMEM158 | 1153 | | | | | -0.49 | -12.35 | -0.33 | -8.34 | 1.03 | -7.05 | -1.29 | -3.45 |
| 219 | TMEM176A | 1337 | | | | | 0.7 | -13.16 | 0.89 | -8.48 | 0.74 | -7.72 | -0.39 | -3.13 |
| 220 | TMEM176B | 1363 | | | | | 0.26 | -15.51 | 0.69 | -10.11 | 0.18 | -8.42 | -0.33 | -2.74 |
| 221 | TNFRSF9 | 602 | | | | | 0.51 | -13.04 | 0.42 | -8.56 | 0.64 | -7.81 | -0.61 | -3.31 |
| 222 | TREML1 | 1288 | | | | | -0.35 | -14.84 | 0.64 | -9.42 | 0.15 | -8.71 | -0.61 | -2.64 |
| 223 | TRNN | 7, 30, 497 | | | | | -0.05 | 1.68 | -1.61 | 0.58 | | | | |
| 224 | TSTA3 | 471 | | | | | | | | | | | | |
| 225 | TUB2A | 1244, 1245, 1277 | | | | | 0.02 | -12.39 | -0.5 | -8.42 | 0.32 | -7.06 | -0.86 | -3.18 |
| 226 | U3BB | 1577 | | | | | 0.13 | -11.86 | 1.31 | -7.47 | | | | |
| 227 | USP32P1 | 912 | | | | | 0.49 | -13.22 | 0.01 | -8.81 | 0.61 | -7.7 | -0.4 | -3.14 |
| 228 | YME1L1 | 765, 771, 768, 769, 764, 760, 762, 766, 770, 777 | | | | | 0.17 | -14.94 | 0.19 | -9.9 | 0.61 | -9.12 | -0.49 | -3.72 |

Fig. 10Q

| Fig. 11 row | Gene symbol | SEQ ID | log2 NUhealed/NUslow | | | log2 C/A | | AI biomarker |
| --- | --- | --- | --- | --- | --- | --- | --- | --- |
| | | | A | C | D | NUhealed | NUslow | |
| 1 | ANKRD36B | 1074 | 1.60 | | | | | x |
| 2 | A2M-AS1 | 703 | | 1.42 | | | | x |
| 3 | ADGRE1 (EMR1) | 966 | | | | 0.15 | -0.56 | x |
| 4 | ANXA3 | 349 | -5.23 | | | | | x |
| 5 | ARPP19 | 388 | -2.26 | -1.43 | | | | |
| 6 | CLEC4D | 109, 702 | -3.49 | | | | | x |
| 7 | CMTM2 | 889 | -2.58 | | | | | x |
| 8 | EC8P | 759 | | | 1.90 | | | |
| 9 | EIF4B | 132 | | | -1.35 | | | x |
| 10 | F8A1 | 1437 | | | -1.88 | | | x |
| 11 | G2MH | 814 | 5.71 | 2.59 | 4.95 | | | x |
| 12 | H1F0 | 289 | | -1.92 | -2.57 | | | x |
| 13 | HIST1H2BG | 1281 | | -2.17 | | | | x |
| 14 | hsa-let-7a-5p | 518 | | | -3.66 | -0.31 | 0.63 | x |
| 15 | hsa-miR-106a-5p | 519 | | | -3.53 | | | x |
| 16 | hsa-miR-125b-5p | 522 | 1.74 | | | -0.35 | 0.79 | x |
| 17 | hsa-miR-126-3p | 1501 | | | -8.88 | | | x |
| 18 | hsa-miR-143-3p | 1513 | | | -4.49 | | | |
| 19 | hsa-miR-146a-5p | 1832 | | | -4.36 | | | |
| 20 | hsa-miR-146b-5p | 1515 | | | -4.33 | | | x |
| 21 | hsa-miR-148a-3p | 1833 | | | -5.10 | | | x |
| 22 | hsa-miR-17-5p | 527 | | | -3.72 | | | x |
| 23 | hsa-miR-197-3 | 1524 | -3.46 | | | | | x |
| 24 | hsa-miR-197-6 | 1526 | | | -2.18 | | | |
| 25 | hsa-miR-19b-3p | 1527 | | | -3.86 | | | |
| 26 | hsa-miR-202-3p | 1528 | | | -2.72 | | | |
| 27 | hsa-miR-20a-5p | 1529 | | | -6.18 | | | |
| 28 | hsa-miR-21-5p | 1834 | | | -6.98 | | | x |
| 29 | hsa-miR-223-3p | 534 | | 1.62 | -2.79 | | | x |
| 30 | hsa-miR-24-3p | 1835 | | -1.92 | -4.36 | | | x |
| 31 | hsa-miR-25-3p | 1836 | | | -2.70 | | | x |
| 32 | hsa-miR-27b-3p | 541 | | | -3.32 | | | x |
| 33 | hsa-miR-29a-3p | 542 | | | -3.10 | | | x |
| 34 | hsa-miR-31-3p | 1837 | | -8.85 | -5.35 | | | |
| 35 | hsa-miR-323b-3p | 1547 | -4.61 | | | | | x |
| 36 | hsa-miR-329-3p | 1548 | | 5.41 | | 4.45E+04 | -1.04E+04 | x |
| 37 | hsa-miR-3667-5p | 1555 | 7.56 | 8.45 | | 3.36E+06 | -8.40E+04 | x |
| 38 | hsa-miR-374b-5p | 1561 | | -3.95 | -3.76 | -4.30E+06 | 9.52E+06 | x |
| 39 | hsa-miR-3934-5p | 1568 | | | -13.55 | | | |
| 40 | hsa-miR-4284 | 1575 | | | 11.33 | | | x |
| 41 | hsa-miR-4485 | 1582 | -3.85 | | | | | x |
| 42 | hsa-miR-4781-3p | 1597 | | -2.12 | -4.69 | | | |
| 43 | hsa-miR-505-3p | 1607 | | | -2.94 | | | x |
| 44 | hsa-miR-551a | 549 | | -3.80 | | | | x |
| 45 | hsa-miR-589-5p | 551 | | | -3.23 | | | x |
| 46 | hsa-miR-6770-5p | 1637 | | | -6.52 | | | |
| 47 | hsa-miR-6820-3p | 1645 | | | -4.33 | | | x |

Fig. 12A

| Fig. 11 row | Gene symbol | SEQ ID | log2 NUhealed/NUslow A | log2 NUhealed/NUslow C | log2 NUhealed/NUslow D | log2 C/A NUhealed | log2 C/A NUslow | AI biomarker |
|---|---|---|---|---|---|---|---|---|
| 48 | hsa-miR-6855-3p | 1649 | | | -3.10 | | | x |
| 49 | hsa-miR-6879-3p | 1652 | | | -3.52 | | | x |
| 50 | hsa-miR-93-5p | 556 | | | -2.85 | | | x |
| 51 | hsa-miR-98-5p | 1665 | | | -6.74 | | | x |
| 52 | HSPD1 | 283 | | -1.60 | | -0.68 | 0.08 | x |
| 53 | IL5RA | 1151 | | | 1.73 | | | x |
| 54 | KIF13A | 1279 | -1.65 | | | | | x |
| 55 | KIR2DL3 | 985 | 4.90 | 2.49 | 2.51 | | | |
| 56 | LGALS2 | 1126 | | | 2.49 | | | x |
| 57 | LOC440300 | 850 | | | 20.49 | | | x |
| 58 | LOC646214 | 855 | | | -3.23 | | | x |
| 59 | MANSC1 | 729 | | | -2.14 | | | x |
| 60 | MXD3 | 270 | -1.79 | -1.51 | | | | x |
| 61 | NDUFA2 | 401 | -1.72 | | | | | x |
| 62 | NOTCH3 | 996 | | | -5.05 | | | x |
| 63 | PECAM1 | 1838 | -2.36 | | -1.99 | | | x |
| 64 | PPDPF | 281 | | | -2.00 | | | x |
| 65 | PRKXP1 | 864 | | -1.81 | | -0.27 | 0.46 | x |
| 66 | ROPN1L | 371 | -4.43 | | | | | x |
| 67 | RPRD1B | 293 | | | -1.52 | | | |
| 68 | S100A12 | 5, 618 | -4.47 | | | | | x |
| 69 | S100P | 344 | -6.70 | | | | | x |
| 70 | SCARNA5 | 1051 | | | 3.70 | | | |
| 71 | SNORA14A | 1318 | | | 2.67 | | | x |
| 72 | SNORD14E | 104 | 1.46 | | 1.70 | | | x |
| 73 | SNORD59B | 134 | | | 3.51 | | | |
| 74 | THBS1 | 844 | | -2.13 | | | | x |
| 75 | TRNN | 7, 30, | -1.48 | | | | | x |
| 76 | U38B | 1677 | | | 6.37 | | | x |

Fig. 12B

METHODS FOR EARLY IDENTIFICATION OF BONE HEALING ABILITY IN INJURED PATIENTS

CROSS-REFERENCE TO RELATED APPLICATIONS

The present application is a 35 U.S.C. § 371 national phase application from, and claims priority to, International Application No. PCT/US2016/016404, filed Feb. 3, 2016, which claims priority under 35 U.S.C. § 119(e) to U.S. Provisional Patent Application No. 62/231,935 filed Feb. 3, 2015 and U.S. Provisional Patent Application No. 62/283,443, filed Sep. 1, 2015, all of which applications are incorporated herein by reference in their entireties.

STATEMENT REGARDING FEDERALLY SPONSORED RESEARCH OR DEVELOPMENT

This invention was made with government support under grant P30AR050950 awarded by National Institute of Health and National Institute of Arthritis and Musculoskeletal and Skin Diseases (NIH-NIAMS). The government has certain rights in the invention.

STATEMENT REGARDING SEQUENCE LISTING SUBMITTED ELECTRONICALLY VIA EFS-WEB

The content of the electronically submitted sequence listing in ASCII text file (Name: 046483-7061US1_SequenceListingTXT; Size: 5,169,590 bytes; Date of Creation: Aug. 3, 2017) is herein incorporated by reference in its entirety.

BACKGROUND OF THE INVENTION

In some patients, fractures of the bone heal very slowly or fail to heal at all (known as "nonunion," and patients who experience this are known as "nonunions"), requiring revision surgeries to perform repairs and transplants, provide mechanical support, and apply therapeutic orthobiologics. In the United States, about 700,000 patients (5-10% of the 8 million annual fracture cases) experience nonunion, with cases of femur or tibia fracture having the highest rates of nonunion at 10 to 46%. The signs and symptoms of nonunion include pain at the fracture site, inability to bear weight, impaired mobility, depression, hardware failure, soft tissue wounds, and pseudoarthrosis in extreme cases. Ongoing clinical care of nonunions adds $1.2 billion to the annual $44 billion cost of new fracture injuries. As the length of time spent with a nonunion increases, the negative impacts of these comorbidities and associated economic costs also increase, including societal impact.

In the normal healing process, a bone fracture initiates a sequence of inflammation, repair, and remodeling that can restore the injured bone to its original state. In humans, the inflammatory phase lasts about 5 to 7 days; it begins with the development of a hematoma and is followed by the invasion of inflammatory cells. These cells, in association with local cells, secrete cytokines, chemokines and growth factors to promote the recruitment of osteogenic progenitor cells and endothelial progenitor cells, essential to initiate the repair process. The recruitment of progenitor cells is divided in four phases: mobilization, migration, invasion and engraftment of the cells to the fracture site. Impairment of one or more of the above processes can result in impaired bone fracture healing. Average normal healing times vary depending on the location of the fracture and range between 3 weeks (phalanges) to 12 weeks (femoral neck or shaft or tibia). A slow healing fracture can take twice as much time as the normal healing and a nonunion does not show signs of healing 6-9 months after injury or if three successive months go by without an interval of healing.

The standard of care to assess fracture healing versus nonunion is "watchful waiting" that includes physical exams and serial radiographs over six to nine months allowing ample time for conservative care. FDA guidelines suggest a diagnosis of nonunion at nine months if union has not occurred or if three successive months go by without signs of progression of bone of formation. After nonunion diagnosis, the patient may undergo nonsurgical interventions such as ultrasound or electrical stimulators, with intervals of watchful waiting. If these conservative treatments fail, revision surgery is performed for debridement, hardware replacement, and/or application of orthobiologics. Watchful waiting resumes after the revision procedures are complete.

Current investigations to identify early molecular markers of fracture healing are mainly restricted to the study of individual proteins with known musculoskeletal association, such as bone turnover markers. These are highly important for the development of future therapeutics that will enhance the healing process, but are not reliable and easily accessible molecular biomarkers of fracture healing. Most recently, genomics techniques such as RNA profiling by microarrays and deep sequencing have been used to identify panels of clinical biomarkers from messenger RNA (mRNA) and microRNA (miRNA) samples. Circulating miRNA profiles were shown to be useful for detecting various pathologies such as traumatic brain injury or poor fracture healing in patients with osteoporosis, however RNA biomarkers that consistently identify and differentiate slow healing and nonunion patients remain unknown.

There is a need in the art of fracture management for a prognostic test that discriminates cases of slow healing and nonunion from those with productive healing. This test should indicate the need for more aggressive therapy or revision surgery within weeks of the injury, reducing the average monitoring period. The present invention addresses this need.

BRIEF SUMMARY OF THE INVENTION

The invention provides a method of identifying a subject with a fractured bone as a candidate for nonunion-mitigating intervention, or an additional intervention following a nonunion-mitigating intervention. The invention further provides a method of promoting bone healing to a subject with a fractured bone. The invention further provides a kit for diagnosing the ability of normal healing, slow healing or no healing of a fractured bone in a subject. The invention further provides a kit for diagnosing the ability of normal healing or slow healing of a fractured bone in a subject. The invention further provides a kit for diagnosing the ability of normal healing or slow healing of a nonunion fractured bone in a subject after a nonunion-mitigating treatment.

In certain embodiments, the method comprises at least one of the following steps: comparing the level of at least one RNA in a sample from the subject to a baseline level of the at least one RNA in a reference sample, wherein a difference in level of the at least one RNA in the subject's sample as compared to the reference sample is indicative of a nonunion or slow healing of the fractured bone in the subject; and, comparing the change of the level of at least one RNA between samples collected from the subject at two or more different times to a baseline change of the level of the at least one RNA in reference samples collected at different times, wherein a difference in the amount of change of the at least one RNA in the subject's samples as compared to the reference samples is indicative of a nonunion or slow healing of the fractured bone in the subject. In other embodiments, the method comprises recommending a nonunion-mitigating intervention for the subject. In yet other embodiments, the method further comprises determining the level of the at least one RNA molecule in a sample from the subject before performing the comparing step(s).

In certain embodiments, the method comprises providing a nonunion-mitigating intervention to the subject if a difference in level, or a difference in change of level, of the at least one RNA in a subject's sample as compared to a reference sample is indicative of a nonunion or slow healing of the fractured bone in the subject.

In certain embodiments, the level, or change in level, of the at least one RNA is at least 1.1-fold higher or lower than the level, or change in level, of the at least one RNA in the reference.

In certain embodiments, the method comprises at least one of the following steps: comparing the level of at least one protein in a sample from the subject to a baseline level of the at least one protein in a reference sample, wherein a difference in level of the at least one protein in the subject's sample as compared to the reference sample is indicative of a nonunion or slow healing of the fractured bone in the subject; and, comparing the change of the level of at least one protein between samples collected from the subject at two or more different times to a baseline change of the level of the at least one protein in reference samples collected at different times, wherein a difference in the amount of change of the at least one protein in the subject's samples as compared to the reference samples is indicative of a nonunion or slow healing of the fractured bone in the subject. In other embodiments, the method further comprises recommending a nonunion-mitigating intervention for the subject. In yet other embodiments, the method further comprises determining the level of the at least one protein in a sample from the subject before performing the comparing step(s).

In certain embodiments, the method comprises providing a nonunion-mitigating intervention to the subject if a difference in level, or a difference in change of level, of the at least one protein in a subject's sample as compared to a reference sample is indicative of a nonunion or slow healing of the fractured bone in the subject.

In certain embodiments, the bone healing does not occur or initiate about 9 months or less after injury or after a nonunion-mitigating intervention. In other embodiments, the bone healing does not occur or initiate about 4 months or less after injury or after a nonunion-mitigating intervention. In yet other embodiments, the bone healing does not occur or initiate about 2 weeks after injury or after a nonunion-mitigating intervention.

In certain embodiments, the bone healing ability is assessed at one or more time periods. In other embodiments, the assessment is done during or before the fourth month of healing.

In certain embodiments, the nonunion-mitigating intervention or the additional intervention comprises an invasive surgical treatment comprising bone graft, removal of scar tissue, application of therapeutic drugs or biologics, and/or immobilization of the fracture with metal plates, rods and/or pins. In other embodiments, the nonunion-mitigating intervention or the additional intervention is a non-invasive treatment comprising electrical stimulation, ultrasound, treatment with therapeutic drugs or biologics, and/or immobilization of the fracture with specialized braces.

In certain embodiments, the at least one RNA is at least one selected from the group consisting of a messenger RNA, a non-coding RNA, and a microRNA.

In certain embodiments, the at least one RNA is selected from the group consisting of SEQ ID NOs: 1-1684 and 1830-1838. In other embodiments, the at least one RNA selected from the group consisting of SEQ ID NOs: 1, 2, 3, 4, 5, 6, 7, 30, 31, 53, 64, 75, 78, 89, 104, 106, 109, 126, 132, 134, 189, 191, 194, 228, 233, 239, 270, 279, 283, 290, 291, 293, 299, 344, 347, 349, 371, 388, 400, 401, 408, 413, 442, 449, 453, 459, 471, 497, 512, 513, 515, 518, 519, 520, 521, 522, 523, 525, 527, 528, 529, 531, 533, 539, 540, 541, 543, 548, 549, 550, 551, 552, 554, 556, 618, 654, 677, 702, 1520, 1549 and 1838 indicates nonunion, slow healing or normal healing after acute injury, and/or indicates successful, no or slow healing after a nonunion-mitigating intervention.

In certain embodiments, the level of the at least one RNA being at least 1.1-fold higher or lower than the level of the RNA in the reference indicates nonunion, slow healing or normal healing after acute injury, and/or indicates successful, no or slow healing after a nonunion-mitigating intervention.

In certain embodiments, the at least one RNA selected from the group consisting of SEQ ID NOs: 9, 24, 45, 103, 124, 164, 219, 314, 351, 516, 517, 526, 534, 535, 542, 553, 562, 563, 572, 573, 582, 598, 599, 602, 609, 619, 620, 624, 625, 634, 652, 653, 655, 656, 676, 682, 698, 700, 701, 703, 721, 722, 723, 724, 725, 729, 753, 759, 760, 762, 764, 765, 766, 768, 769, 770, 771, 777, 781, 785, 789, 791, 794, 806, 814, 816, 824, 844, 850, 855, 862, 864, 867, 885, 889, 910, 911, 912, 914, 915, 917, 918, 931, 934, 938, 954, 958, 961, 962, 966, 968, 985, 996, 1004, 1024, 1027, 1030, 1032, 1035, 1051, 1054, 1063, 1066, 1068, 1069, 1070, 1071, 1073, 1074, 1075, 1080, 1086, 1087, 1096, 1100. 1109, 1110, 1111, 1114, 1115, 1126, 1141, 1151, 1153, 1154, 1180, 1201, 1216, 1228, 1244, 1245, 1277, 1279, 1281, 1283, 1286, 1288, 1293, 1318, 1337, 1363, 1382, 1405, 1406, 1431, 1437, 1489, 1493, 1499, 1500, 1501, 1502, 1506, 1508, 1512, 1513, 1514, 1515, 1516, 1517, 1522, 1523, 1524, 1526, 1527, 1528, 1529, 1531, 1532, 1533, 1534, 1535, 1536, 1539, 1541, 1542, 1543, 1544, 1546, 1547, 1548, 1551, 1552, 1554, 1555, 1561, 1562, 1565, 1568, 1575, 1576, 1579, 1582, 1584, 1585, 1597, 1598, 1599, 1600, 1601, 1605, 1607, 1608, 1609, 1610, 1626, 1627, 1628, 1637, 1640, 1643, 1645, 1648, 1649, 1652, 1654, 1656, 1657, 1662, 1665, 1677, 1830, 1831, 1832, 1833, 1834, 1835, 1836, and 1837 indicates nonunion, slow healing or normal healing after acute injury, and/or indicates successful, no or slow healing after a nonunion-mitigating intervention.

In certain embodiments, the level of the at least one RNA being at least 1.1-fold higher or lower than the level of the RNA in the reference indicates nonunion, slow healing or normal healing after acute injury, and/or indicates successful, no or slow healing after a nonunion-mitigating intervention.

In certain embodiments, the differential expression of at least one RNA selected from the group consisting of SEQ ID NOs: 1, 2, 4, 5, 6, 7, 9, 24, 30, 45, 53, 64, 75, 78, 89, 99, 103, 104, 109, 124, 126, 132, 134, 164, 191, 194, 219, 228, 239, 270, 279, 283, 290, 291, 293, 299, 314, 344, 347, 349, 351, 371, 388, 400, 401, 408, 413, 442, 449, 459, 471, 497, 512, 513, 515, 516, 518, 519, 520, 522, 523, 525, 527, 528, 529, 531, 533, 534, 535, 539, 540, 541, 542, 543, 548, 549, 551, 552, 553, 556, 562, 563, 572, 573, 582, 598, 599, 602, 609, 618, 620, 624, 625, 634, 652, 653, 654, 655, 656, 676, 677, 682, 698, 701, 702, 703, 722, 725, 729, 753, 759, 760, 762, 764, 765, 766, 768, 769, 770, 771, 777, 781, 785, 789, 791, 794, 814, 816, 824, 844, 850, 855, 862, 864, 867, 885, 889, 912, 914, 915, 917, 918, 934, 938, 954, 958, 961, 962, 966, 985, 996, 1004, 1024, 1027, 1030, 1032, 1035, 1051, 1054, 1063, 1066, 1068, 1069, 1070, 1071, 1073, 1074, 1080, 1086, 1100, 1109, 1110, 1111, 1114, 1115, 1126, 1141, 1151, 1153, 1154, 1180, 1201, 1216, 1228, 1244, 1245, 1277, 1279, 1281, 1283, 1286, 1288, 1318, 1337, 1363, 1382, 1406, 1437, 1489, 1499, 1501, 1512, 1513, 1515, 1517, 1520, 1524, 1526, 1527, 1528, 1529, 1531, 1532, 1536, 1539, 1542, 1544, 1546, 1547, 1548, 1549, 1551, 1555, 1561, 1562, 1565, 1568, 1575, 1576, 1579, 1582, 1584, 1597, 1598, 1599, 1600, 1601, 1605, 1607, 1608, 1609, 1610, 1627, 1628, 1637, 1640, 1643, 1645, 1648, 1649, 1652, 1656, 1662, 1665, 1677, 1831, 1832, 1833, 1834, 1835, 1836, 1837 and 1838 indicates nonunion, slow healing or normal healing after acute injury, and/or indicates successful, no or slow healing after a nonunion-mitigating intervention.

In certain embodiments, the differential expression of at least one RNA selected from the group consisting of SEQ ID NOs: 1, 2, 4, 5, 6, 7, 9, 24, 30, 45, 53, 64, 75, 78, 89, 99, 103, 104, 109, 124, 126, 132, 134, 164, 191, 194, 219, 228, 239, 270, 279, 283, 290, 291, 293, 299, 314, 344, 347, 349, 351, 371, 388, 400, 401, 408, 413, 442, 449, 459, 471, 497, 512, 513, 515, 516, 518, 519, 520, 522, 523, 525, 527, 528, 529, 531, 533, 534, 535, 539, 540, 541, 542, 543, 548, 549, 551, 552, 553, 556, 562, 563, 572, 573, 582, 598, 599, 602, 609, 618, 620, 624, 625, 634, 652, 653, 654, 655, 656, 676, 677, 682, 698, 701, 702, 703, 722, 725, 729, 753, 759, 760, 762, 764, 765, 766, 768, 769, 770, 771, 777, 781, 785, 789, 791, 794, 814, 816, 824, 844, 850, 855, 862, 864, 867, 885, 889, 912, 914, 915, 917, 918, 934, 938, 954, 958, 961, 962, 966, 985, 996, 1004, 1024, 1027, 1030, 1032, 1035, 1051, 1054, 1063, 1066, 1068, 1069, 1070, 1071, 1073, 1074, 1080, 1086, 1100, 1109, 1110, 1111, 1114, 1115, 1126, 1141, 1151, 1153, 1154, 1180, 1201, 1216, 1228, 1244, 1245, 1277, 1279, 1281, 1283, 1286, 1288, 1318, 1337, 1363, 1382, 1406, 1437, 1489, 1499, 1501, 1512, 1513, 1515, 1517, 1520, 1524, 1526, 1527, 1528, 1529, 1531, 1532, 1536, 1539, 1542, 1544, 1546, 1547, 1548, 1549, 1551, 1555, 1561, 1562, 1565, 1568, 1575, 1576, 1579, 1582, 1584, 1597, 1598, 1599, 1600, 1601, 1605, 1607, 1608, 1609, 1610, 1627, 1628, 1637, 1640, 1643, 1645, 1648, 1649, 1652, 1656, 1662, 1665, 1677, 1831, 1832, 1833, 1834, 1835, 1836, 1837 and 1838 indicates nonunion, slow healing or normal healing after acute injury.

In certain embodiments, the level of the at least one RNA being at least 1.1-fold higher or lower than the level of the RNA in the reference indicates nonunion, slow healing or normal healing after acute injury.

In certain embodiments, the differential expression of at least one RNA selected from the group consisting of SEQ ID NOs: 2, 4, 5, 7, 30, 53, 75, 104, 109, 126, 132, 134, 270, 283, 291, 293, 299, 344, 349, 371, 388, 401, 413, 497, 516, 519, 522, 527, 528, 534, 541, 542, 549, 551, 556, 618, 702, 703, 729, 759, 814, 844, 850, 855, 864, 889, 985, 996, 1051, 1074, 1126, 1151, 1279, 1281, 1318, 1437, 1501, 1513, 1515, 1524, 1526, 1527, 1528, 1529, 1532, 1547, 1548, 1555, 1561, 1568, 1575, 1582, 1597, 1607, 1637, 1645, 1649, 1652, 1665, 1677, 1832, 1833, 1834, 1835, 1836, 1837 and 1838 indicates successful, no or slow healing after a nonunion-mitigating intervention.

In certain embodiments, the level of the at least one RNA being at least 1.1-fold higher or lower than the level of the RNA in the reference indicates successful, no or slow healing after a nonunion-mitigating intervention.

In certain embodiments, the change of expression over time of at least one
RNA selected from the group consisting of SEQ ID NOs: 1, 2, 4, 7, 24, 30, 53, 75, 78, 89, 103, 109, 126, 132, 134, 189, 191, 194, 219, 239, 270, 279, 283, 290, 291, 347, 349, 388, 401, 408, 442, 449, 471, 497, 512, 513, 515, 516, 518, 520, 522, 523, 528, 529, 531, 533, 548, 549, 550, 551, 552, 556, 562, 572, 582, 599, 652, 653, 655, 656, 677, 698, 702, 722, 844, 864, 885, 938, 966, 996, 1054, 1074, 1154, 1520, 1528, 1542, 1546, 1548, 1561, 1584, 1605 and 1838 indicates nonunion, slow healing or normal healing after acute injury, and/or indicates successful, no or slow healing after a nonunion-mitigating intervention.

In certain embodiments, the change of expression over time of at least one RNA selected from the group consisting of SEQ ID NOs: 1, 2, 4, 7, 24, 30, 53, 75, 78, 89, 103, 109, 126, 132, 134, 189, 191, 194, 219, 239, 270, 279, 290, 291, 347, 349, 388, 401, 408, 442, 449, 471, 497, 512, 513, 515, 518, 520, 522, 523, 528, 529, 531, 533, 548, 549, 550, 551, 552, 556, 562, 572, 582, 599, 652, 653, 655, 656, 677, 698, 702, 722, 844, 885, 938, 966, 996, 1054, 1074, 1154, 1520, 1528, 1542, 1546, 1584, 1605 and 1838 indicates nonunion, slow healing or normal healing after acute injury.

In certain embodiments, the change of expression over time of the at least one RNA being at least 1.1-fold higher or lower than the change of expression over time of the RNA in the reference indicates nonunion, slow healing or normal healing after acute injury.

In certain embodiments, the change of expression over time of at least one RNA selected from the group consisting of SEQ ID NOs: 283, 516, 864, 966, 1548 and 1561 indicates successful, no or slow healing after a nonunion-mitigating intervention.

In certain embodiments, the change of expression over time of the at least one RNA being at least 1.1-fold higher or lower than the change of expression over time of the RNA in the reference indicates successful, no or slow healing after a nonunion-mitigating intervention.

In certain embodiments, the at least one RNA is selected from the group consisting of SEQ ID NOs: 8-556.

In certain embodiments, the differential expression of at least one RNA from the group of SEQ ID NOs: 8-556 indicates either acute injury or no injury.

In certain embodiments, the level of the at least one RNA being at least 1.1-fold higher or lower than the level of the RNA in the reference indicates either acute injury or no injury.

In certain embodiments, the differential expression of at least one RNA from the group of SEQ ID NOs: 8, 10, 12, 13, 15, 16, 18, 19-23, 26, 9, 30-33, 35-37, 41, 43, 44, 46, 48-52, 54-56, 61, 63-65, 67-69, 73, 74, 77-79, 81, 82, 86, 88-92, 95-102, 104, 106, 107, 108, 110, 119-122, 126-128, 130-132, 134, 135, 137, 139, 140, 144 147-150, 152, 156-158, 161, 162, 167-170, 172, 175, 179-183, 187-201, 203-207, 209-212, 215, 216, 217, 218, 220, 222-228, 231-237, 239, 240, 242, 247, 249, 251-253, 256, 258-266, 268-273, 275-277, 279, 280, 283, 285, 286, 288, 291, 293, 295-306, 308, 310, 311, 321, 322, 324, 327, 331, 333, 335, 338-341, 343, 347, 348, 352, 354, 357, 358, 364, 365, 367, 371, 372, 375, 378, 383, 386, 388, 390, 396-401, 403, 404, 407, 408, 415, 417, 420, 421, 423, 425, 428, 431, 433-435, 438, 441, 442, 444, 446-449, 451, 453, 454, 459, 461, 462, 467, 472, 474-478, 480, 486, 487, 495, 496, 497, 500, 502, 503, 505, 506, 508, 510, 511, 513-515, 519, 520, 525, 527-530, 533 and 556 indicates either nonunion or no injury.

In certain embodiments, the level of the at least one RNA being at least 1.1-fold higher or lower than the level of the RNA in the reference indicates either nonunion or no injury.

In certain embodiments, the differential expression of at least one RNA from the group of SEQ ID NOs: 25, 53, 58 105, 124, 143, 229, 289, 290, 292, 309, 328, 332, 334, 336, 344, 349, 385, 405, 406, 422, 471, 489 and 512 allows differentiating between acute injury and no injury or between nonunion and no injury.

In certain embodiments, the level of the at least one RNA being at least 1.1-fold higher or lower than the level of the RNA in the reference indicates acute injury or nonunion differentiated from no injury.

In certain embodiments, the level or change in level of the at least one protein is higher or lower by at least 1.1-fold than the level or change in level of the at least one protein in the reference.

In certain embodiments, the bone healing does not occur or initiate about 9 months or less after injury or after a nonunion-mitigating intervention. In other embodiments, the bone healing does not occur or initiate about 4 months or less after injury or after a nonunion-mitigating intervention. In yet other embodiments, the bone healing does not occur or initiate about 2 weeks after injury or after a nonunion-mitigating intervention.

In certain embodiments, the bone healing ability is assessed at one or more time periods. In other embodiments, the assessment is done during or before the fourth month of healing.

In certain embodiments, the nonunion-mitigating intervention or the additional intervention comprises an invasive surgical treatment comprising bone graft, removal of scar tissue, application of therapeutic drugs or biologics, and/or immobilization of the fracture with metal plates, rods or pins.

In certain embodiments, the nonunion-mitigating intervention or the additional intervention is a non-invasive treatment comprising electrical stimulation, ultrasound, treatment with therapeutic drugs or biologics, or immobilization of the fracture with specialized braces.

In certain embodiments, the at least one protein is selected from the group consisting of SEQ ID NOs: 1685-1829.

In certain embodiments, the differential expression of at least one protein selected from the group consisting of SEQ ID NOs: 1695, 1696, 1697, 1698, 1699, 1701, 1702, 1703, 1705, 1706, 1707, 1708, 1711, 1712, 1714, 1715, 1716, 1717, 1718, 1719, 1720, 1721, 1722, 1723, 1730, 1732, 1734, 1735, 1736, 1740, 1741, 1742, 1743, 1744, 1752, 1753, 1756, 1763, 1764, 1768, 1769, 1774, 1775, 1778, 1779, 1781, 1783, 1785, 1787, 1791, 1794, 1796, 1797, 1798, 1803, 1806, 1810, 1812, 1814, 1816, 1820, 1823, 1827, 1828 and 1829 indicates nonunion, slow healing or normal healing after acute injury.

In certain embodiments, the level of the at least one protein being at least 1.1-fold higher or lower than the level of the protein in the reference indicates nonunion, slow healing or normal healing after acute injury.

In certain embodiments, the change of expression over time of at least one protein selected from the group consisting of SEQ ID NOs: 1732, 1783, 1796 and 1804 indicates nonunion, slow healing or normal healing after acute injury.

In certain embodiments, the change of expression over time of the at least one protein being at least 1.1-fold higher or lower than the change of expression over time of the protein in the reference indicates nonunion, slow healing or normal healing after acute injury.

In certain embodiments, the at least one RNA is selected from the group consisting of SEQ ID NOs: 1-1684 and 1830-1838.

In certain embodiments, the at least one RNA is a mRNA or ncRNA selected from the group consisting of SEQ ID NOs: 1-515, 557-1471, and 1838.

In certain embodiments, the at least one RNA is a miRNA selected from the group consisting of SEQ ID NOs: 516-556, 1472-1684, and 1830-1837.

In certain embodiments, the at least one protein is selected from the group consisting of SEQ ID NOs: 1685-1829.

In certain embodiments, determining the level of the at least one RNA comprises at least one technique selected from the group consisting of reverse transcription, PCR, microarray, next generation sequencing, nuclease protection, probe hybridization to one or more molecular copies of the at least one RNA, pyrosequencing, and primer extension.

In certain embodiments, determining the level of the at least one protein comprises at least one technique selected from the group consisting of western blot, immunoprecipitation, immunoassay, immunohistochemistry, immunofluorescence and radioimmunoassay, chemical assay, enzyme assay, mass spectrometry, chromatography, electrophoresis, biosensor, antibody microarray, multiplex aptamer-based assay, agglutination assay, turbidity assay and nephelometric assay.

In certain embodiments, the sample is at least one selected from the group consisting of blood, peripheral blood, serum, plasma, urine, stool samples, saliva, biological fluid gathered from an anatomic area in proximity to the fractured bone, biological fluid from fractured hone, primary cells, and cultured cells.

In certain embodiments, the comparison of level of RNA and/or protein expression is computed using at least one statistical method selected from the group consisting of pairwise and multi-class ANOVA tests, t-tests, chi-square tests, Bayesian tests, machine learning algorithms, and Extraction of Differential Gene Expression (EDGE) tool analysis.

In certain embodiments, the ratios, sums, products or other mathematical combinations of expression level of at least two RNAs as compared to the corresponding expression levels in reference samples are used to calculate a score or composite score that characterizes the bone healing ability in the subject.

In certain embodiments, the ratios, sums, products or other mathematical combinations of expression level of at least two proteins as compared to the corresponding expression levels in reference samples are used to calculate a score or composite score that characterizes the bone healing ability in the subject.

In certain embodiments, the subject is a mammal. In other embodiments, the mammal is a human.

In certain embodiments, the kit comprises one or more probes that detect at least one isolated RNA selected from the group consisting of SEQ ID NOs: 1, 2, 4, 5, 6, 7, 9, 24, 30, 45, 53, 64, 75, 78, 89, 99, 103, 104, 109, 124, 126, 132, 134, 164, 189, 191, 194, 219, 228, 239, 270, 279, 283, 290, 291, 293, 299, 314, 344, 347, 349, 351, 371, 388, 400, 401, 408, 413, 442, 449, 459, 471, 497, 512, 513, 515, 516, 518, 519, 520, 522, 523, 525, 527, 528, 529, 531, 533, 534, 535, 539, 540, 541, 542, 543, 548, 549, 550, 551, 552, 553, 556, 562, 563, 572, 573, 582, 598, 599, 602, 609, 618, 620, 624, 625, 634, 652, 653, 654, 655, 656, 676, 677, 682, 698, 701, 702, 703, 722, 725, 729, 753, 759, 760, 762, 764, 765, 766, 768, 769, 770, 771, 777, 781, 785, 789, 791, 794, 814, 816, 824, 844, 850, 855, 862, 864, 867, 885, 889, 912, 914, 915, 917, 918, 934, 938, 954, 958, 961, 962, 966, 985, 996, 1004, 1024, 1027, 1030, 1032, 1035, 1051, 1054, 1063, 1066, 1068, 1069, 1070, 1071, 1073, 1074, 1080, 1086, 1100, 1109, 1110, 1111, 1114, 1115, 1126, 1141, 1151, 1153, 1154, 1180, 1201, 1216, 1228, 1244, 1245, 1277, 1279, 1281, 1283, 1286, 1288, 1318, 1337, 1363, 1382, 1406, 1437, 1489, 1499, 1501, 1512, 1513, 1515, 1517, 1520, 1524, 1526, 1527, 1528, 1529, 1531, 1532, 1536, 1539, 1542, 1544, 1546, 1547, 1548, 1549, 1551, 1555, 1561, 1562, 1565, 1568, 1575, 1576, 1579, 1582, 1584, 1597, 1598, 1599, 1600, 1601, 1605, 1607, 1608, 1609, 1610, 1627, 1628, 1637, 1640, 1643, 1645, 1648, 1649, 1652, 1656, 1662, 1665, 1677, 1831, 1832, 1833, 1834, 1835, 1836, 1837 and 1838.

In certain embodiments, the kit comprises one or more probes that detect at least one isolated protein selected from the group consisting of SEQ ID NOs: 1695, 1696, 1697, 1698, 1699, 1701, 1702, 1703, 1705, 1706, 1707, 1708, 1711, 1712, 1714, 1715, 1716, 1717, 1718, 1719, 1720, 1721, 1722, 1723, 1730, 1732, 1734, 1735, 1736, 1740, 1741, 1742, 1743, 1744, 1752, 1753, 1756, 1763, 1764, 1768, 1769, 1774, 1775, 1778, 1779, 1781, 1783, 1785, 1787, 1791, 1794, 1796, 1797, 1798, 1803, 1804, 1806, 1810, 1812, 1814, 1816, 1820, 1823, 1827, 1828, 1829.

In certain embodiments, the kit comprises one or more probes that detect at least one isolated RNA selected from the group consisting of SEQ ID NOs: 2, 4, 5, 7, 30, 53, 75, 104, 109, 126, 132, 134, 270, 283, 291, 293, 299, 344, 349, 371, 388, 401, 413, 497, 516, 519, 522, 527, 528, 534, 541, 542, 549, 551, 556, 618, 702, 703, 729, 759, 814, 844, 850, 855, 864, 889, 966, 985, 996, 1051, 1074, 1126, 1151, 1279, 1281, 1318, 1437, 1501, 1513, 1515, 1524, 1526, 1527, 1528, 1529, 1532, 1547, 1548, 1555, 1561, 1568, 1575, 1582, 1597, 1607, 1637, 1645, 1649, 1652, 1665, 1677, 1832, 1833, 1834, 1835, 1836, 1837 and 1838.

In certain embodiments, the kit comprises a plurality of oligonucleotides that detect at least one RNA selected from the group consisting of SEQ ID NOs: 1-1684 and 1830-1838.

In certain embodiments, the kit comprises a plurality of amino acids that detect at least one protein selected from the group consisting of SEQ ID NOs: 1685-1829.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is a table listing the fold-differences for blood mRNAs or ncRNAs significantly different (ANOVA $p<0.05$) between AInorm and AIslow, AInu or AInotnorm. Time periods for FIGS. 1-4 and 7 were 1a: 0-2 weeks after acute injury or nonunion diagnosis, 1b: 3-4 weeks, 2: 5-8 weeks, 3: 9-12 weeks, 4: 13-16 weeks, 5: 17-20 weeks, 6: 21-24 weeks, 7: 25 or more weeks. Fold differences were positive for lower expression in AInorm and negative for higher expression in AInorm.

Figure 2:
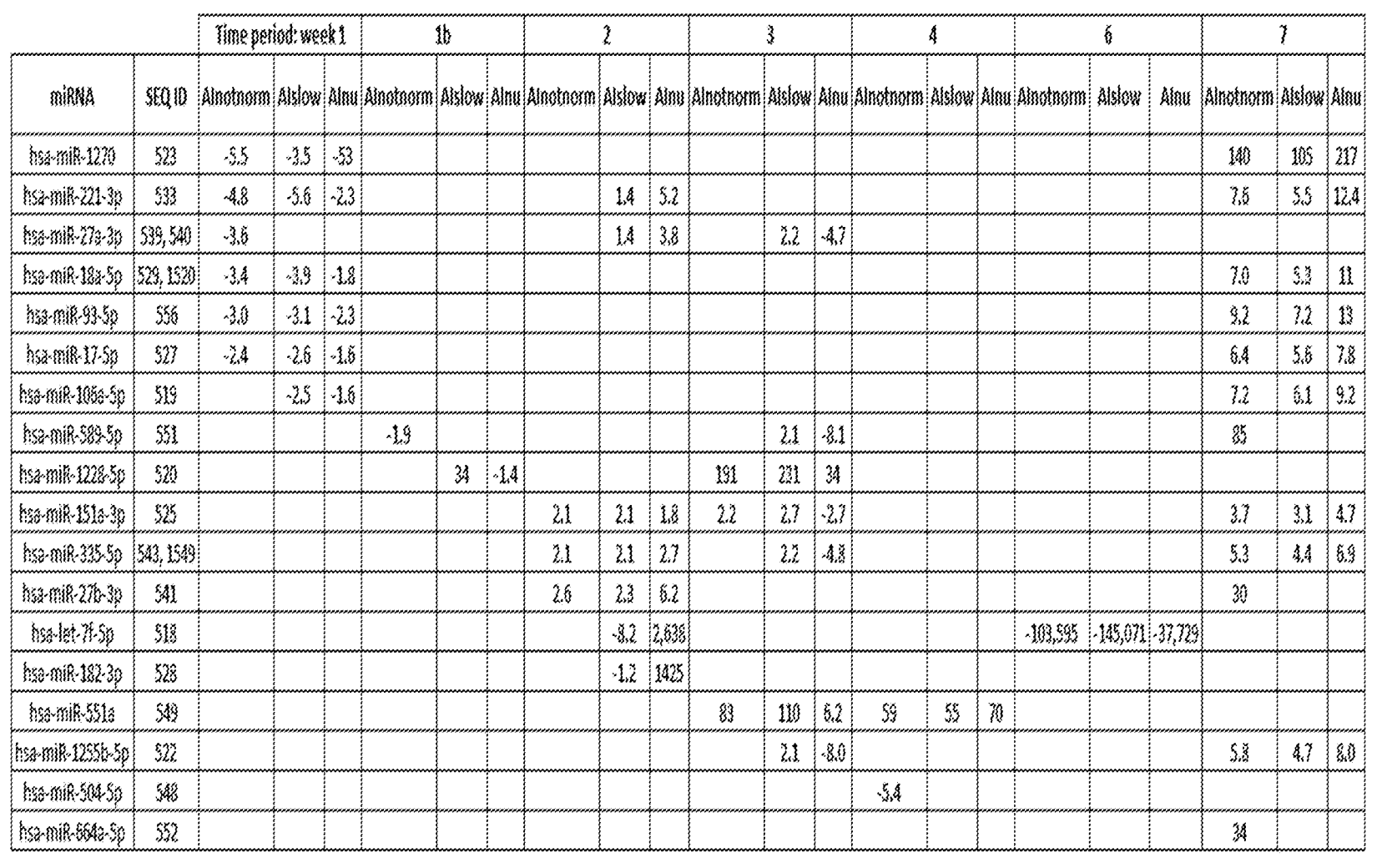

FIG. 2 is a table listing the fold-differences for blood microRNAs that were significantly different (ANOVA $p<0.05$) between AInorm and AIslow, AInu or AInotnorm.

FIG. 3 is a table listing mRNA or ncRNA abundance changes over healing time intervals. The ANOVA p-value indicates significance of difference between AInorm and AIslow for the observed changes between time periods. p 0.04, nonunion average fold-change 2.1 from 1a to 4 (n=3). p: ANOVA p-value, nc: no change with magnitude $>1.5\times$.

FIG. 4 is a table listing microRNA abundance changes over healing time intervals. nc: no change with magnitude $>1.5\times$.

FIG. 5 is a table listing microRNA detection rates across samples or subjects. The p-value is from a chi-square test for independent distributions in the outcome categories.

FIG. 6 is a table listing the fold-differences for blood RNAs in nonunion patients with slow or no healing relative to healed nonunion patients.

FIGS. 7A-7B are a series of tables listing protein biomarkers for healing ability with average abundance fold-differences that are greater than 1.5 in absolute magnitude compared to AInorm, and a significant difference by ANOVA ($p<0.05$). Protein expression levels were measured using the SOMAscan screening assay for serum. Values are the average of AIslow/AInorm or AInu/AInorm within time periods (negative indicates inverse ratio, AInorm higher), or log2 of average time 2, 3 or 4/1a for change over time intervals.

FIG. 8 is a table listing the number of subjects and blood RNA samples used for time course profiling of fracture healing by RT-qPCR. The time periods for FIGS. 8-12B were A: 0-2 weeks after acute injury or nonunion diagnosis, B: 3-4 weeks, C: 5-10 weeks, D: 11-16 weeks.

FIGS. 10A-10Q are a series of tables listing blood RNA biomarker RT-qPCR data for acute injury outcomes over four months of fracture healing. Values are shown if a difference met the ANOVA $p<0.05$ threshold. Values in standard format are from global normalization and are log2 of the ratios indicated in column headers. Values in scientific notation are from alternative analyses using reference gene normalization, subtraction of expression values rather than ratios to calculate difference, or both.

FIGS. 12A-12B are a series of tables listing blood RNA biomarker RT-qPCR data for nonunion outcomes over four months of healing after therapeutic intervention. Values are shown if a difference met the ANOVA p<0.05 threshold. Values in standard format are from global normalization and are log2 of the ratios indicated in column headers. Values in italics are from alternative analyses using reference gene normalization, subtraction of expression values rather than ratios to calculate difference, or both.

DETAILED DESCRIPTION OF THE INVENTION

Figure 9A:
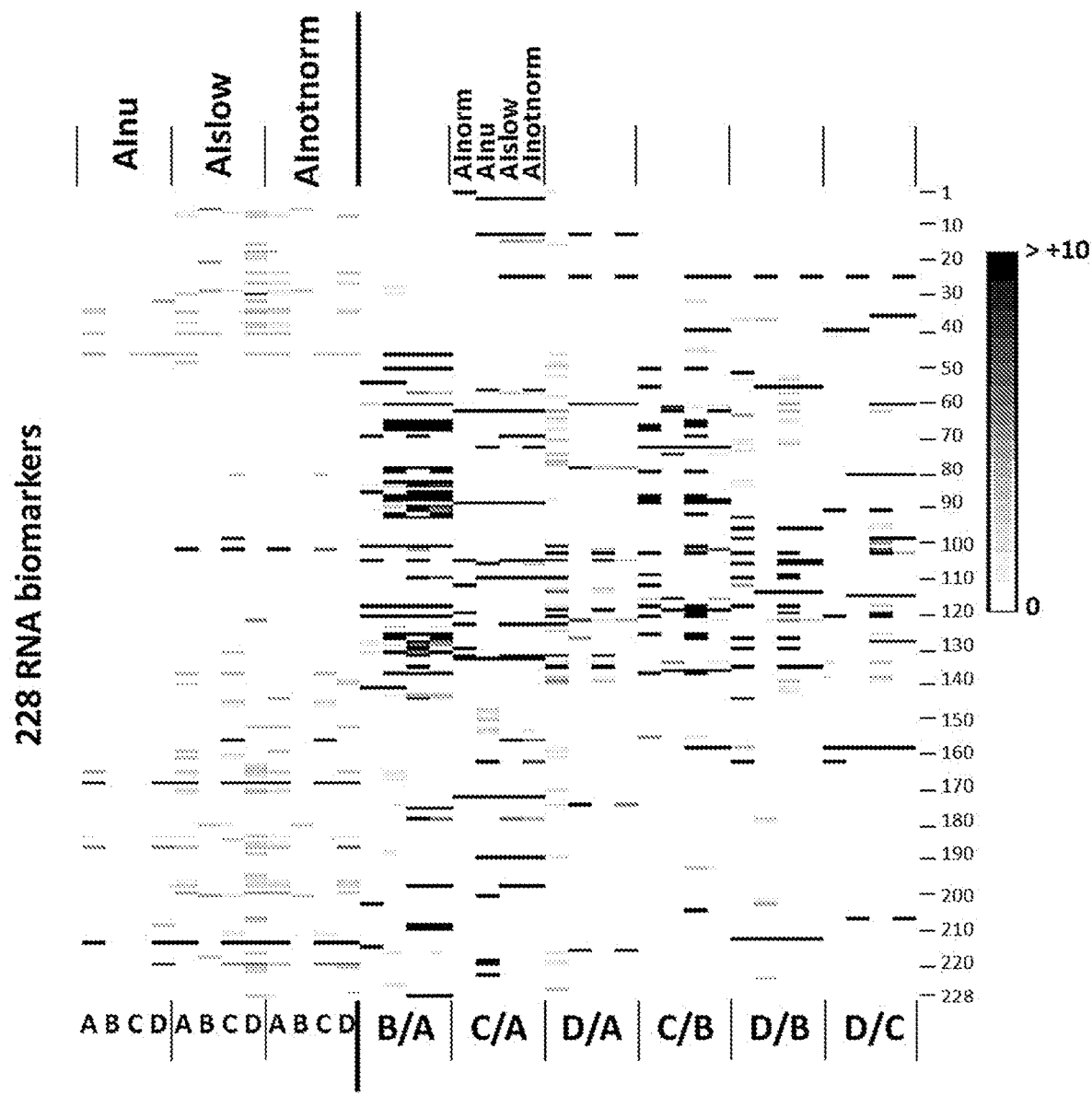
FIGS. 9A-9B are a set of heatmaps depicting blood RNA biomarker expression differences between acute injury outcomes over four months of fracture healing, measured by RT-qPCR. ANOVA was used to test for differences between AInorm patients and AInu, AIslow or AInotnorm patients during the four healing time periods A-D (left set of columns). Each row represents an RNA target (numbered on right, recited in FIGS. 10A-10Q), a shaded block is present if the target showed a statistically significant difference ($p<0.05$) compared to AInorm, and the shading levels (grayscale bars) represent the log2 ratio of the average difference with positive values for higher expression than in AInorm (FIG. 9A) and negative values for lower expression (FIG. 9B). Similar ANOVA testing was performed for expression changes between time periods (right set of columns). For each of the indicated time intervals (from A to B: B/A, and so forth), the average log2 ratio of change over time is shown for patients in each healing outcome category. A shaded block is present if the target's magnitude of change was significantly different ($p<0.05$) compared to AInorm (FIGS. 10A-10Q); positive values (FIG. 9A) are abundance increases from the earlier to later time period and negative values (FIG. 9B) are abundance decreases from earlier to later times.

The present invention relates to the discovery that the expression levels of certain RNA molecules, comprising messenger RNA (mRNA), non-coding RNA (ncRNA) and/or microRNA (miRNA), and protein can be used as a diagnostic signature to predict or monitor the bone healing ability in an acutely injured subject or in a subject undergoing treatment for a diagnosed nonunion. In various embodiments described herein, the invention relates to compositions useful for differentiating between a nonunion, slow healing, or normal healing of a fractured bone, methods using same, and treatment recommendations. The invention further includes a kit comprising candidate biomarkers for assessing the bone healing ability in an acutely injured or nonunion subject, thereby allowing the medical provider the ability to counsel and manage the patient in a more appropriate fashion.

The full disclosures of the priority documents U.S. Provisional Patent Application No. 62/231,935, filed Feb. 3, 2015, and U.S. Provisional Patent Application No. 62/283,443, filed Sep. 1, 2015, are incorporated by reference in their entireties herein.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, specific materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more specifically ±5%, even more specifically ±1%, and still more specifically ±0.1% from the specified value, as such variations are appropriate to perform the disclosed methods.

As used herein, the term "acute injury" refers to the initial or primary bone fracture and the time period from 0-14 days after such fracture occurred.

As used herein, the term "AInorm" refers to biomarkers for acute injury that healed in a normal time (AInorm). As used herein, the term "AIslow" refers to biomarkers for acute injury that healed slowly (i.e., requiring more time than the normal time noted in the art; AIslow). As used herein, the term "AInu" refers to biomarkers for acute injury that did not significantly heal and was later diagnosed as a nonunion (AInu). As used herein, the term "AInotnorm" refers to biomarkers for acute injury which was either AIslow or AInu (AInotnorm).

The term "ameliorating" or "treating" means that the clinical signs and/or the symptoms associated with the disease or disorder are lessened as a result of the actions performed. The signs or symptoms to be monitored will be characteristic of a particular disease or disorder and will be well known to the skilled clinician, as will the methods for monitoring the signs and conditions.

As used herein the term "amount" refers to the abundance or quantity of a constituent in a mixture.

As used herein, the term "amplicon" or "PCR products" or "PCR fragments" or "amplification products" refers to extension products that comprise the primer and the newly synthesized copies of the target sequences.

As used herein, the term "biomarker" includes a polynucleotide or polypeptide molecule that is present or absent or increased or decreased in quantity or activity in subjects having the diseases or conditions contemplated herein as compared to subjects not affected with such diseases or conditions.

As used herein, the term "biomarkers for diagnosis" or "diagnosis signature" includes a group of markers such as mRNA or ncRNA or miRNA or protein, the quantity or activity of each member of which is correlated with subjects having the diseases or conditions contemplated herein as compared to subjects not affected with such diseases or conditions. In certain embodiments, the diagnosis signature may include only those markers. In certain embodiments, the signature includes one, two, three, four, five, six, seven, eight, or nine or more proteins or RNAs that may be mRNAs, ncRNAs, miRNAs or any combination of classes.

The term "biopsy" refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. Biopsies also include a fine needle aspiration biopsy, a minicore needle biopsy, and/or a conventional percutaneous core needle biopsy.

The term "concentration" refers to the abundance of a constituent divided by the total volume of a mixture. The term concentration can be applied to any kind of chemical mixture, but most frequently it refers to solutes and solvents in solutions.

As used herein, the term "control" refers to a nucleic acid or peptide with known or substantially non-varying concentrations throughout a set of samples.

The term "diagnosis" is used herein to refer to the identification or classification of a molecular or pathological state, disease or condition.

The term "expression" as used herein is defined as the transcription and/or translation of a particular nucleotide sequence.

"Level," "abundance" and "expression level" as used herein describe the absolute or relative concentrations of a biomarker in a sample, regardless of whether the synthesis or degradation of the biomarker occur in cells within the sample or occur in non-sampled cells, tissues or organs that subsequently release the biomarker into the sample.

The terms "dysregulated" and "dysregulation" as used herein describes a decreased (down-regulated) or increased (up-regulated) level of expression of an RNA or protein present and detected in a sample obtained from a subject as compared to the level of expression of that RNA or protein present in a reference sample, such as a reference sample obtained from one or more normal, not-at-risk subjects, or from the same subject at a different time point. In certain instances, the level of RNA or protein expression is compared with an average value obtained from more than one not-at-risk individuals. In other instances, the level of RNA or protein expression is compared with a RNA or protein level assessed in a sample obtained from one normal, not-at-risk subject.

"Differentially increased expression" or "upregulation" refers to expression levels which are at least 10% or more, for example, 20%, 30%, 40%, or 50%, 60%, 70%, 80%, 90% higher or more, and/or 1.1 fold. 1.2 fold, 1.4 fold, 1.6 fold, 1.8 fold, 2.0 fold higher or more, and any and all whole or partial increments therebetween, than a reference sample.

"Differentially decreased expression" or "down regulation" refers to expression levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween, than a reference sample.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "measuring" according to the present invention relates to determining the amount or concentration, preferably semi-quantitatively or quantitatively. Measuring can be done directly and/or indirectly.

The terms "messenger RNA" and "message RNA" herein refer to RNA polynucleotides in which two or more consecutive portions of the sequence of bases are consistent with codons of the genetic code, and the polynucleotide is capable of being translated by ribosomes into a polypeptide. "Non-coding RNA" herein refers to all other RNA polynucleotides of any length that are not messenger RNA.

As used herein, "microRNA" or "miRNA" describes RNA molecules, generally about 15 to about 50 nucleotides in length, preferably 17-23 nucleotides, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (pri-miRNA) through sequential cleavage by RNase III enzymes.

The term "next-generation sequencing" (NGS), also known as high-throughput sequencing, is used herein to describe a number of different modem sequencing technologies that allow sequencing of DNA and RNA (as cDNA) templates much more quickly and cheaply than the previously used Sanger sequencing (Metzker, 2010, Nature Reviews Genetics 11.1: 31-46). It is based on micro- and nanotechnologies to reduce the size of sequencing reactions, leverage reagent costs across more templates and samples, and to enable massively parallel sequencing reactions. It can be highly multiplexed, allowing simultaneous sequencing and analysis of 96 or more samples. NGS includes first, second, third as well as subsequent next generation sequencing technologies.

As used herein, the term "nonunion" refers to bone fractures that fail to heal within six to nine months after the acute injury or have clinical signs and symptoms consistent with a nonunion. "Slow healing" is defined as successful healing reached after a prolonged period significantly longer than observed in a normal healing population of patients with the same type of bone fracture.

As used herein, the term "nonunion-mitigating intervention" refers to procedures that help fracture healing in nonunion subjects. Such interventions include for example nonsurgical interventions such as ultrasound and/or electrical stimulators and/or specialized braces, with intervals of watchful waiting. Invasive interventions further include revision surgery, surgical removal of dead tissue, insertion of internal brace (e.g., rod, plate or screw), insertion of bone graft, application of therapeutic drugs or biologics including but not limited to injection of one or more bone morphogenetic proteins (BMPs), amputation to prevent further injury, and/or application of orthobiologics.

As used herein, the term "NUhealed" refers to a nonunion subject who successfully healed after nonunion-mitigating intervention. "NUslow" refers to a nonunion subject who experienced no or slow healing after nonunion-mitigating intervention, By "nucleic acid" is meant any nucleic acid, whether composed of deoxyribonucleosides or ribonucleosides, and whether composed of phosphodiester linkages or modified linkages such as phosphodiester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T".

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "polynucleotide" includes cDNA, RNA, DNA/RNA hybrid, anti-sense RNA, siRNA, miRNA, snoRNA, ncRNA, linc-RNA, snRNA, genomic DNA, synthetic forms, and mixed polymers, both sense and antisense strands, and may be chemically or biochemically modified to contain non-natural or derivatized, synthetic, or semisynthetic nucleotide bases. Also, included within the scope of the invention are alterations of a wild type or synthetic gene, including but not limited to deletion, insertion, substitution of one or more nucleotides, or fusion to other polynucleotide sequences.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

A "primer" is an oligonucleotide, usually of about 15, 20, 25, 30, 35, 40, 45 or 50 nucleotides in length, that is capable of hybridizing in a sequence specific fashion to the target sequence and being extended during the PCR.

As used herein, the term "reference" refers to a sample or set of samples used as a standard for comparison to a patient sample. Both reference samples and patient samples may contain control nucleic acids and peptides.

The term "RNA" as used herein is defined as ribonucleic acid.

The term "sample" or "biological sample" refers to a sample obtained from an organism or from components (e.g., cells) of an organism, A "sample" or "biological sample" as used herein means a biological material from a subject, including but is not limited to organ, tissue, exosome, blood, plasma, saliva, urine and other body fluid. A sample can be any source of material obtained from a subject.

A "subject" or "patient" as used herein may he a human or non-human mammal. Non-human mammals include, for example, livestock and pets, such as ovine, bovine, porcine, canine, feline and murine mammals. In certain embodiments, the subject is human.

The term "therapeutic" as used herein means a treatment and/or prophylaxis. A therapeutic effect is obtained by suppression, remission, or eradication of a disease state.

As used herein, to "treat" means reducing the frequency with which symptoms of a disease, disorder, or adverse condition, and the like, are experienced by a subject.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease, condition or disorder thereby preventing or removing all signs of the disease, condition or disorder. As another example, administration of the agent after clinical manifestation of the disease to combat the symptoms of the disease comprises "treatment" of the disease.

As used herein, "10% greater" refers to expression levels that are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments there between, than a control or a reference sample.

As used herein, "10% lower" refers to expression levels that are at least 10% or more, for example, 20%, 30%, 40%, or 50%, 60%, 70%, 80%, 90% lower or more, and/or 1.1 fold, 1.2 fold, 1.4 fold, 1.6 fold, 1.8 fold, 2.0 fold lower or more, and any and all whole or partial increments there between, than a control or a reference sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

Description

The present invention relates to the discovery that the level of expression of certain RNA molecules, comprising messenger RNA (mRNA), non-coding RNA (ncRNA) and/or microRNA (miRNA), and certain proteins can be used as a diagnostic signature to predict or monitor the bone healing ability in an acutely injured subject. In certain embodiments, the level of expression of certain RNA molecules is used as a diagnostic signature to predict and/or monitor the bone healing ability in a nonunion subject.

In certain embodiments, the invention relates to a method of identifying a subject with a fractured bone as a candidate for nonunion-mitigating intervention, and/or an additional intervention, following a nonunion-mitigating intervention. In other embodiments, the method of the invention comprises: (a) comparing the level of at least one RNA in a sample from the subject to a baseline level of the at least one RNA in a reference sample, wherein a difference in level of the at least one RNA in the subject's sample as compared to the reference sample is indicative of a nonunion or slow healing of the fractured bone in the subject; and/or comparing the change of the level of at least one RNA between samples collected from the subject at two or more different times to a baseline change of the level of the at least one RNA in reference samples collected at different times, wherein a difference in the amount of change of the at least one RNA in the subject's samples as compared to the reference samples is indicative of a nonunion or slow healing of the fractured bone in the subject; and (b) recommending a nonunion-mitigating intervention for the subject.

In certain embodiments, the invention relates to a method of identifying a subject with a fractured bone as a candidate for nonunion-mitigating intervention, or an additional intervention following a nonunion-mitigating intervention. In other embodiments, the method of the invention comprises: (a) comparing the level of at least one protein in a sample from the subject to a baseline level of the at least one protein in a reference sample, wherein a difference in level of the at least one protein in the subject's sample as compared to the reference sample is indicative of a nonunion or slow healing of the fractured bone in the subject; and/or comparing the change of the level of at least one protein between samples collected from the subject at two or more different times to a baseline change of the level of the at least one protein in reference samples collected at different times, wherein a difference in the amount of change of the at least one protein in the subject's samples as compared to the reference samples is indicative of a nonunion or slow healing of the fractured bone in the subject; and (b) recommending a nonunion-mitigating intervention for the subject.

In certain embodiments, the invention relates to a method of detecting, predicting or monitoring the bone healing ability in an acutely injured subject. In other embodiments, the bone fracture healing is at least one selected from the group consisting of nonunion, slow healing, and normal healing. In yet other embodiments, the method of the invention comprises determining the level of expression of at least one RNA or protein in a sample from the subject. In yet other embodiments, the method of the invention comprises comparing the level of the at least one RNA or protein in the sample from the subject relative to a baseline level in a reference wherein a difference in the level of RNA or protein in the sample from the RNA or protein level in the reference is indicative of a nonunion, slow healing, or normal healing of the fractured bone. In yet other embodiments, the method of the invention comprises recommending and/or administering a treatment for the subject in need thereof.

In certain embodiments, the subject with nonunion or slow bone fracture healing is known or expected to be at risk of developing a poor (i.e., less than normal) bone healing ability. Non-limiting examples of risk factors associated with poor bone healing ability include lifestyle and health factors that may interfere with bone healing, such as smoking, excessive alcohol use, poor nutritional status, poor general health, fitness deficits, and diabetes; factors that may contribute to loss of bone strength, such as use of non-steroidal anti-inflammatory drugs (NSAID), use of immunosuppressive drugs, other drugs such as anticonvulsants, and the thyroid hormone replacement, thyroxine; type and site of fracture, such as fracture in a poorly vascularized site, instability at the fracture site, high energy trauma, and poor condition of the soft tissues around the bone; ancestry, such as individuals of European or Asian ancestry who have increased risk for osteoporosis; age, such as elderly individuals who are at increased risk for poor bone healing; women who have experienced early menopause, late menarche, or the loss of their ovaries.

In certain embodiments, the bone healing does not occur or initiate about 1, 2, 3, or 4 week(s) after injury. In other embodiments, the bone healing does not occur or initiate about 1, 2, 3, 4, 5, 6, 7, 8, 9, 10, 11 or 12 month(s) after injury. In yet other embodiments, the bone healing does not occur or initiate about 1 year or more after injury.

In certain aspects of the invention, the bone healing ability is assessed at one or more time periods often during or before the fourth month of healing.

In some embodiments, the treatments of the nonunion or slow healing fracture include, but are not limited to, non-invasive treatments such as electrical stimulation, ultrasound or specialized braces, and invasive measures, such as surgical removal of dead tissue, insertion of internal brace (e.g., rod, plate or screw), insertion of bone graft, application of therapeutic drugs or biologics including but not limited to injection of one or more bone morphogenetic proteins (BMPs), and/or amputation to prevent further injury.

Control and Reference Amounts of Expression of the RNA or Protein Marker(s):

The method of the invention includes comparing the measured amount of expression of a RNA biomarker(s) in a biological sample from a subject to a control amount of expression of another (i.e., a different) RNA marker(s) in the same biological sample from the same subject.

In certain embodiments, the RNA comprises a messenger RNA (mRNA) and/or non-coding RNA (ncRNA). In other embodiments, the RNA comprises a microRNA (miRNA).

In certain embodiments, the control amount of expression of the RNA is a value for expression of the RNA that is accepted in the art (e.g., spiked-in). Non-limiting examples of control RNA include GAPDH, TBP, β-actin, RNU6-6P (hsa-RNU6b) and/or miR-450a-5p.

In one aspect, the method of the invention includes comparing the measured amount of expression of a protein biomarker(s) in a biological sample from a subject to a control amount of expression of a different protein marker(s) in the same biological sample from the same subject.

In certain embodiments, the reference level of expression of the RNA(s) or protein(s) may be obtained by measuring the expression level of a RNA or a protein in a healthy subject. For example, the healthy subject may include a non-injured healthy subject. In certain embodiments, the healthy subject is a subject of similar age, gender, race as the acutely injured subject. In other embodiments, the healthy subject includes a bone injured subject with normal healing ability, as recognized in the art.

In certain embodiments, finding a deviation or no deviation of the biomarker RNA level between the measured RNA in the injured subject and the reference subject(s) allows attributing the deviation or no deviation to a particular diagnosis, prediction and/or prognosis of impaired bone fracture healing in the subject. In other embodiments, finding a deviation or no deviation of the protein biomarker level is similarly used for diagnosis, prediction and/or prognosis of impaired bone fracture healing in the subject. The method may also be performed for a subject at two or more successive time points; the respective outcomes at said successive time points may be compared, whereby the presence or absence of a change between the diagnosis, prediction and/or prognosis of impaired fracture healing at said successive time points is determined. When so applied, the method can monitor a change in the diagnosis, prediction and/or prognosis of the fracture healing in the subject over time.

Figure 9B:
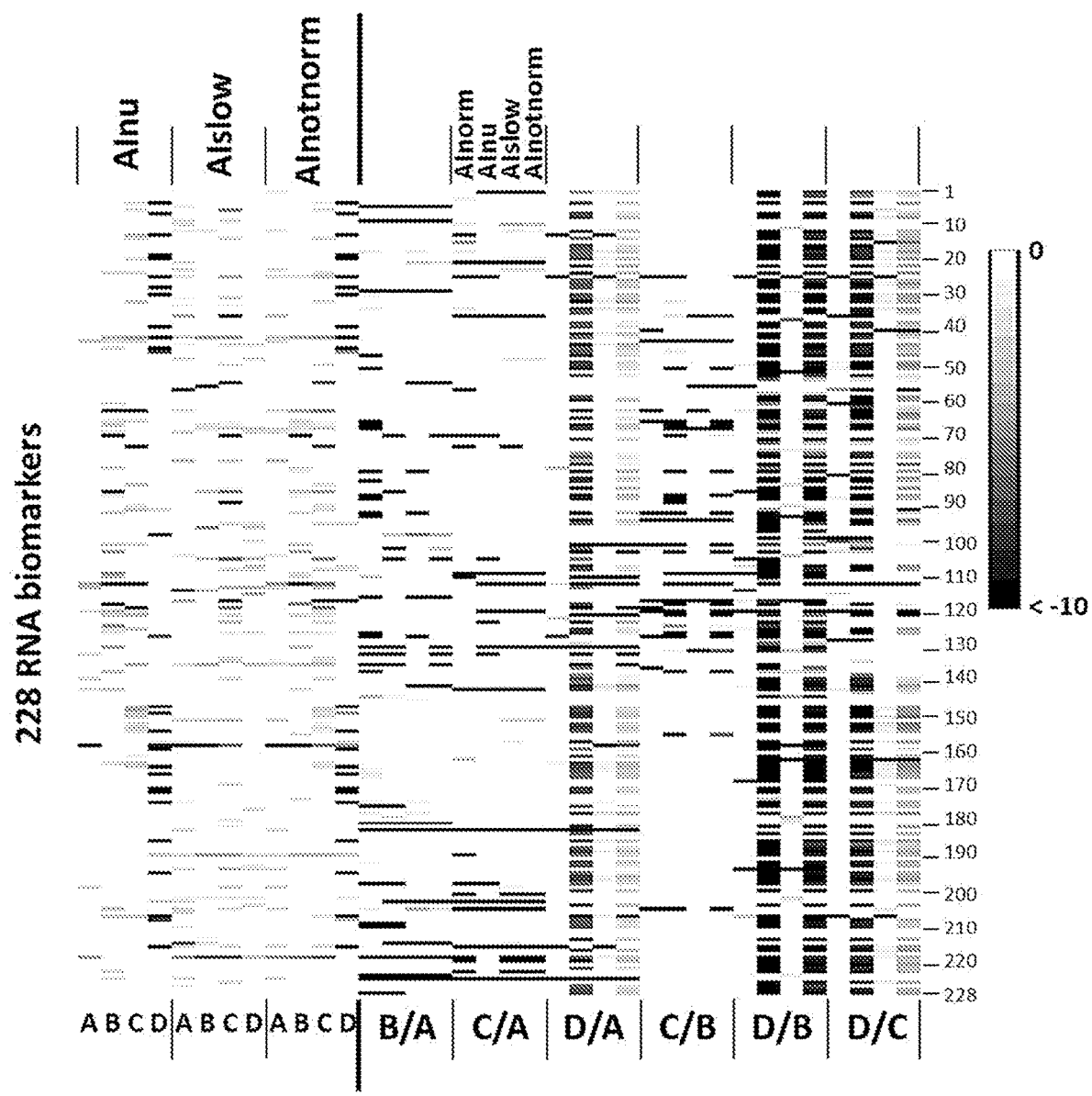
Figures 11A, 11B:
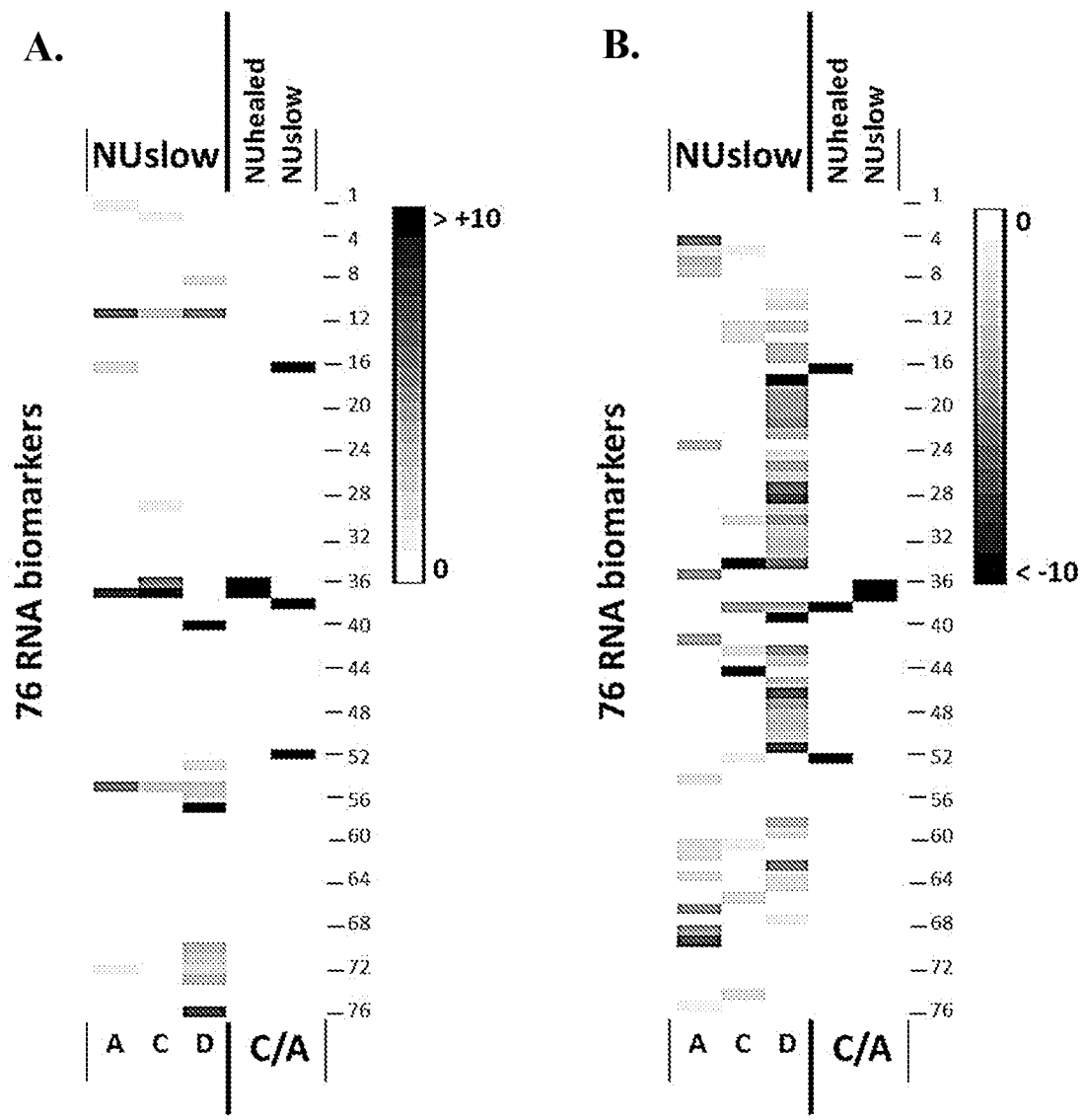
FIGS. 11A-11B are a set of heatmaps illustrating blood RNA biomarker expression differences between nonunion outcomes over four months of healing after therapeutic intervention, measured by RT-qPCR. All methods and the data presentation are as described for FIGS. 9A-9B. Significant differences within time periods (left columns) are shown for NUslow compared to NUhealed. Significant differences in magnitudes of change between time periods A to C are shown in the right columns. Row numbers refer to RNA biomarkers recited in FIGS. 12A-12B.

In certain embodiments, a deviation of the quantity of at least one RNA biomarker, as for example recited in FIGS. 9A-12B, in a sample from a subject, as compared to a reference value representing the prediction or diagnosis of a healthy subject or with normal healing ability, can be indicative of the subject's nonunion or slow healing ability.

In certain embodiments, a deviation of the quantity of at least one RNA biomarker as recited in FIGS. 1-6 (as well as in FIGS. 7-12, 16, and 18-24 of U.S. Provisional Patent Application No. 62/283,443, filed Sep. 1, 2015), in a sample from a subject, as compared to a reference value representing the prediction or diagnosis of a healthy subject or with normal healing ability, can be indicative of the subject's nonunion or slow healing ability.

In certain embodiments, a deviation of the quantity of at least one protein biomarker as recited in FIGS. 7A-7B (as well as in FIGS. 31-48 and 168-170 of U.S. Provisional Patent Application No. 62/283,443), in a sample from a subject, as compared to a reference value representing the prediction or diagnosis of a healthy subject or with normal healing ability, can be indicative of the subject's nonunion or slow healing ability. In other embodiments, the absence of such deviation from the reference value representing the prediction or diagnosis of bone fracture healing can be indicative of a good prognosis for bone fracture healing in the subject. In yet other embodiments, the presence or absence of such deviation allows determining whether a subject is or is not respectively in need of a therapeutic or prophylactic treatment of nonunion or slow fracture healing.

Comparison of the Measured Amount of Expression of the RNA or Protein Marker for Detecting, Predicting or Monitoring the Bone Healing Ability:

The method includes comparing the measured amount of expression of the RNA or protein to the reference amount of expression of the RNA or protein. A measured or reference RNA or protein amount may be an absolute quantitation of RNA molecules or protein, or may be a relative quantitation to one or more control RNA or protein levels.

In certain embodiments, the RNA marker is a mRNA, ncRNA and/or a miRNA selected from FIGS. 10A-10Q and 12A-12B. In other embodiments, the RNA marker is a mRNA, ncRNA and/or a miRNA selected from FIGS. 1-6 (as well as FIGS. 7-12, 16, and 18-24 in U.S. Provisional Patent Application No. 62/283,443). In yet other embodiments, the RNA marker is at least one selected from the group consisting of SEQ ID NOs: 1-556, as recited in FIGS. 26 and 27 of U.S. Provisional Patent Application No. 62/283,443. In yet other embodiments, the RNA marker is at least one selected from the group consisting of SEQ ID NOs: 1-1684 and 1830-1838 (as recited in FIGS. 26, 27, 163 and 164 in U.S. Provisional Patent Application No. 62/283,443). In yet other embodiments, the at least one RNA is a mRNA or a ncRNA selected from the group consisting of SEQ ID NOs: 1-515, 557-1471 (as recited in FIGS. 26 and 163 in U.S. Provisional Patent Application No. 62/283,443), and 1838. In yet other embodiments, the at least one RNA is a miRNA selected from the group consisting of SEQ ID NOs: 516-556, 1472-1684 (as recited in FIGS. 27 and 164 in U.S. Provisional Patent Application No. 62/283,443), and 1830-1837.

In certain embodiments, the RNA marker used to differentiate between a slow healing and normal healing or between a nonunion and normal healing is at least one selected from the group consisting of SEQ ID NOs: 1, 2, 4-7, 24, 53, 64 75, 78, 89, 103, 104, 109, 126, 132, 134, 189, 191, 194, 219, 222, 228, 239, 270, 279, 283, 290, 291, 293, 299, 344, 347, 349, 371, 388, 400, 401, 413, 442, 449, 459, 471, 512, 516, 518, 519, 520, 522, 523, 525, 527-529, 531, 533, 534, 539, 541, 543, 548-552, 556, 562, 572, 582, 599, 618, 652, 653, 655, 656, 698, 702, 703, 722, 814, 844, 864, 885, 889, 914, 938, 954, 966, 985, 996, 1054, 1074, 1126, 1153, 1154, 1286, 1501, 1512, 1515, 1526, 1528, 1529, 1542, 1546-1548, 1555, 1561, 1562, 1568, 1584, 1597, 1605, 1607, 1610, 1627, 1637, 1649, 1652, 1662, 1665, 1677, 1832, 1834-1836, and 1838. In other embodiments, the level of expression of the RNA marker representative of nonunion, slow healing or normal healing after acute injury is a least 1.1-fold higher or lower than the level of the corresponding reference RNA.

In certain embodiments, the differential expression of at least one RNA selected from the group consisting of SEQ NOs: 5, 24, 103, 126, 194, 219, 239, 290, 347, 349, 449, 520, 562, 572, 582, 599, 618, 652, 653, 655, 656, 698, 722, 844, 885, 914, 938, 954, 966, 996, 1054, 1074, 1153, 1154, 1286, 1512, 1528, 1542, 1546, 1561, 1562, 1584, 1605, 1607, 1610, 1627, 1637 and 1662, and the level of the at least one RNA being at least 1.1-fold higher or lower than the level of the RNA in the reference, indicates nonunion, slow healing or normal healing after acute injury.

In certain embodiments, the differential expression of at least one RNA selected from the group consisting of SEQ ID NOs: 1, 2, 4-7, 53, 64, 75, 78, 89, 104, 109, 126, 132, 134, 189, 191, 194, 222, 228, 239, 270, 279, 283, 290, 291, 293, 344, 347, 349, 371, 388, 400, 401, 413, 442, 449, 459, 471 and 512, and the level of the at least one RNA being at least 1.1-fold higher or lower than the level of the RNA in the reference, indicates nonunion, slow healing or normal healing after acute injury.

In certain embodiments, the differential expression of at least one RNA selected from the group consisting of SEQ ID NOs: 518, 519, 520, 522, 523, 525, 527-529, 531, 533, 539, 541, 543, 548-552 and 556, and the level of the at least one RNA being at least 1.1-fold higher or lower than the level of the RNA in the reference, indicates nonunion, slow healing or normal healing after acute injury.

In certain embodiments, the differential expression of at least one RNA selected from the group consisting of SEQ ID NOs: 24, 103, 219, 290, 347, 349, 449, 520, 562, 572, 582, 599, 652, 653, 655, 656, 698, 722, 844, 885, 938, 954, 966, 996, 1054, 1074, 1154, 1512, 1528, 1542, 1546, 1584, 1605 and 1637, and the change of level between two times of the at least one RNA being at least 1.1-fold higher or lower than the change of level between two times of the RNA in the reference, indicates nonunion, slow healing or normal healing after acute injury.

In certain embodiments, the differential expression of at least one RNA selected from the group consisting of SEQ ID NOs: 1, 2, 4, 7, 53, 75, 78, 89, 109, 126, 132, 134, 189, 191, 194, 222, 239, 270, 279, 290, 291, 347, 349, 388, 401, 442, 471 and 512, and the change of level between two times of the at least one RNA being at least 1.1-fold higher or lower than the change of level between two times of the RNA in the reference, indicates nonunion, slow healing or normal healing after acute injury.

In other embodiments, the differential expression of at least one RNA selected from the group consisting of SEQ ID NOs: 518, 520, 522, 523, 528, 529, 531, 533 and 548-552, and the change of level between two times of the at least one RNA being at least 1.1-fold higher or lower than the change of level between two times of the RNA in the reference, indicates nonunion, slow healing or normal healing after acute injury.

In yet further embodiments, the measured presence or absence of at least one RNA selected from the group consisting of SEQ ID NOs: 194, 518, 520 and 528 indicates nonunion, slow healing or normal healing after acute injury.

In certain embodiments, the RNA marker used to differentiate between slow healing or successful healing after a nonunion-mitigating intervention is at least one selected from the group consisting of SEQ ID NOs: 5, 109, 270, 283, 299, 344, 349, 371, 516, 534, 618, 702, 703, 814, 864, 889, 966, 985, 996, 1074, 1126, 1501, 1515, 1526, 1528, 1529, 1547, 1548, 1555, 1561, 1568, 1597, 1607, 1637, 1649, 1652, 1665, 1677, 1832, 1834, 1835, 1836 and 1838, and the level of the at least one RNA being at least 1.1-fold higher or lower than the level of the RNA in the reference indicates slow or no healing or successful healing.

In certain embodiments, the RNA marker used to differentiate between slow healing or successful healing after a nonunion-mitigating intervention is at least one selected from the group consisting of SEQ ID NOs: 2, 4, 53, 75, 109, 126, 222, 344, 349, 371, 388, 413 and 528. In other embodiments, the level of expression of the RNA marker representative of slow healing or successful healing after a nonunion-mitigating intervention is a least 1.1-fold higher or lower than the level of the corresponding reference RNA.

In certain embodiments, the differential expression of at least one RNA selected from the group consisting of SEQ ID NOs: 283, 516, 864, 966, 1548 and 1561, and the change of level between two times of the at least one RNA being at least 1.1-fold higher or lower than the change of level between two times of the RNA in the reference, indicates no or slow healing, or successful healing, after a nonunion-mitigating intervention.

In some embodiments, the RNA marker used to differentiate between acute injury or no injury is at least one selected from the group consisting of SEQ ID NOs: 8-556. In other embodiments, the level of expression of the RNA marker representative of acute injury or no injury is a least 1.1-fold higher or lower than the level of the corresponding reference RNA.

In certain embodiments, the RNA marker used to differentiate between nonunion, and no injury is at least one selected from the group consisting of SEQ ID NOs: 8, 10, 12, 13, 15, 16, 18, 19-23, 26, 29, 30-33, 35-37, 41, 43, 44, 46, 48-52, 54-56, 61, 63-65, 67-69, 73, 74, 77-79, 81, 82, 86, 88-92, 95-102, 104, 106, 107, 108, 110, 119-122, 126-128, 130-132, 134, 135, 137, 139, 140, 144, 147-150, 152, 156-158, 161, 162, 167-170, 172, 175, 179-183, 187-201, 203-207, 209-212, 215, 216, 217, 218, 220, 222-228, 231-237, 239, 240, 242, 247, 249, 251-253, 256, 258-266, 268-273, 275-277, 279, 280, 283, 285, 286, 288, 291, 293, 295-306, 308, 310, 311, 321, 322, 324, 327, 331, 333, 335, 338-341, 343, 347, 348, 352, 354, 357, 358, 364, 365, 367, 371, 372, 375. 378, 383, 386, 388, 390, 396-401, 403, 404. 407, 408, 415, 417, 420, 421, 423, 425, 428, 431, 433-435, 438, 441, 442, 444, 446-449, 451, 453, 454, 459, 461, 462, 467, 472, 474-478, 480, 486, 487, 495, 496, 497, 500, 502, 503, 505, 506, 508, 510, 511, 513-515, 519, 520, 525, 527-530, 533 and 556. In other embodiments, the level of expression of the RNA marker representative of nonunion and no injury is a least 1.1-fold higher or lower than the level of the corresponding reference RNA.

In certain embodiments, the RNA marker used to differentiate between acute injury and no injury or between nonunion and no injury is at least one selected from the group consisting of SEQ ID NOs: 25, 53, 58, 105, 124, 143, 229, 289, 290, 292, 309, 328, 332, 334, 336, 344, 349, 385, 405, 406, 422, 471, 489 and 512. In other embodiments, the level of expression of the RNA marker representative of acute injury or nonunion differentiated from no injury is a least 1.1-fold higher or lower than the level of the corresponding reference RNA.

In certain embodiments, the protein marker is at least one selected from the group consisting of SEQ ID NOs: 1685-1829 (FIGS. 7A-7B, as well as FIG. 165 in U.S. Provisional Patent Application No. 62/283,443), in other embodiments, the protein marker is at least one selected from the group consisting of BDNF, CGA/TSHB, TIMP1, GPC5, LYVE1, NGF, APOA1, IL20, PYY. GAS1, CASP2, TGFB2, LEPR, ESAM, IFNA2, PDE7A, CXCL2/CXCL3, GZMCB2, MMP1, CTSA, HSPA8, VWF, CXCL6, and FAM107A (as recited in FIG. 168 in U.S. Provisional Patent Application No. 62/283,443), wherein the at least one protein is from a sample collected 2 weeks or less after bone fracture and is indicative of a slow healing of the fractured bone in the subject. In yet other embodiments, the protein marker is at least one selected from the group consisting of BDNF, CGA/TSFIB, CST5, TIMP1, LDHB, FGF23, GPC5, LYVE1, FGF4, PGLYRP1, NCF, ICAM3, PTK6, C2, APOA1 and RETN (as recited in FIG. 169 in U.S. Provisional Patent Application No. 62/283,443), wherein the at least one protein is from a sample collected 2 weeks or less after bone fracture and is indicative of a nonunion of the fractured bone in the subject. In yet other embodiments, the protein marker is at least one selected from the group consisting of FGFR3, EPHA1, FCN2, CAST, IGHG1/IGHG2/IGHG3/IGHG4, DSG2, IL12RB1, TNFRSF13C, FCGR2A/FCGR2B, CD209, SPOCK2, PGD, TGFBI, NGF, AMHR2, ACY1, CCL15, FGF8, IL1RAPL2, FCRL3, OMD, TNFRS14, AMR NTN4, GP6, C1S, TNF, SLC25A18, LIN7B, PRLR, SPINT2, DMP1, FGF23, PLG, EREG, TNFRS17 and PRSS3 (as recited in FIG. 170 in U.S. Provisional Patent Application No. 62/283,443), wherein the at least one protein is from a sample collected 3-4 months after bone fracture and is indicative of a nonunion of the fractured bone in the subject. In yet other embodiments, the protein marker is at least one selected from the group consisting of LDHB, NGF, GPC5 and LYVE1 (as recited in FIGS. 34, 38 and 48 in U.S. Provisional Patent Application No. 62/283,443), wherein the at least one protein is from two or more samples collected at different times from the same subject, and the change in protein expression between times is indicative of normal healing, slow healing or nonunion in the subject when compared to the protein expression change in a normal healing reference.

In certain aspects of the present invention, the level of RNA or protein expression is determined for at least one RNA in a sample obtained from a subject. The sample can be a fluid sample such as a blood sample, blood sample containing peripheral blood mononuclear cells (PBMCs), a blood serum sample, a urine sample, a stool sample, a sample from biological fluid gathered from an anatomic area in proximity to the fractured bone, and biological fluid from fractured bone, or any other body fluid in addition to those recited herein. In certain embodiments, the sample can be cultured osteoblastic cells or mesenchymal stem cells obtained from the subject. The RNA or protein biomarkers may be measured in primary and/or further (e.g., secondary, tertiary, and so forth) cultures of the cells. These cells may be obtained from the site of the nonunion or slow healing fractured bone in the subject, or from a site distant from the nonunion or slow healing fractured bone.

Any method known to those in the art can be employed for determining the level of RNA expression. For example, a microarray can be used (e.g. Affymetrix GeneChip microarray). Microarrays are known in the art and consist of a surface to which probes that correspond in sequence to gene products (e.g. mRNAs, polypeptides, fragments thereof and so forth) can be specifically hybridized or bound to a known position. To detect at least one RNA of interest, a hybridization sample is formed by contacting the test sample with at least one nucleic acid probe. One probe for detecting RNA is a labeled nucleic acid probe capable of hybridizing to RNA. The nucleic acid probe can be, for example, a full-length nucleic acid molecule, or a portion thereof, such as an oligonucleotide of at least 10, 15, or 20 nucleotides in length and sufficient to specifically hybridize under stringent conditions to appropriate RNA. The hybridization sample is maintained under conditions which are sufficient to allow specific hybridization of the nucleic acid probe to a RNA target of interest. Specific hybridization can be performed under high stringency conditions or moderate stringency conditions, as appropriate. In certain embodiments, the hybridization conditions for specific hybridization are high stringency. Specific hybridization, if present, is then detected using standard methods. If specific hybridization occurs between the nucleic acid probe and a RNA in the test sample, the sequence that is present in the nucleic acid probe is also present in the RNA of the subject. More than one nucleic acid probe can also be used. Hybridization intensity data detected by the scanner are automatically acquired and processed by microarray softwares (e.g. MAS, RMA). Raw data is normalized to expression levels using a given target intensity. An alternate method to measure RNA expression profiles of a small number of different genes is by e.g. classical TaqMan® Gene Expression Assays, TaqMan® Low Density Array-micro fluidic cards (Applied Biosystems), or any quantitative PCR (qPCR) system known in the art. The transcriptional state of a sample, particularly RNAs, may also be measured by other nucleic acid expression technologies known in the art.

In certain embodiments, the RNAs, such as mRNAs and miRNAs, are detected in a sample from the subject under examination. Any method known to those in the art can be employed for determining the level of RNAs (particularly, the mRNAs, ncRNAs and miRNAs provided herein in FIGS. 1-6 and 9A-12B, as well as FIGS. 7-12, 16, and 18-24 in U.S. Provisional Patent Application No. 62/283,443). RNA can be isolated from the sample using any method known to those in the art. Non-limiting examples include commercial kits, such as the miRNeasy® commercially available from Qiagen (Netherlands) or the Mini Kit TRI Reagent® commercially available from Molecular Research Center, Inc. (Cincinnati, Ohio).

Generally, the isolated RNA may be amplified using methods known in the art. Amplification systems utilizing, for example, PCR or RT-PCR methodologies, are known to those skilled in the art. For a general overview of amplification technology, see, for example, Dieffenbach et al., PCR Primer: A Laboratory Manual, Cold Spring Harbor Laboratory Press, New York (1995).

An alternative method for determining the level of RNAs includes the use of molecular beacons and other labeled probes useful in, for example multiplex PCR. In a multiplex PCR assay, one PCR mixture contains primers and probes to amplify and detect multiple selected mRNAs, ncRNAs or miRNAs. Typically, different fluorochromes are used to discriminate each RNA's PCR product in the assay. The molecular beacon or probe is detected to determine the level of RNA. Molecular beacons are described, for example, by Tyagi and Kramer (Nature Biotechnology 1996; 14, 303-308) and by Andrus and Nichols (U.S. Patent Application Publication No. 20040053284).

Another accurate method for profiling RNA expression can be the use of next generation sequencing (NGS) including first, second, third as well as subsequent NGS technologies. Non-limiting examples could be the nanopore or semiconductor technologies (e.g. Oxford Nanopore Technologies, United Kingdom) or the Illumina RNA-Seq and micmRNA-Seq methodologies for HiSeq or MiSeq instruments (Chu and Corey, Nucleic Acid Ther. 2012; 22(4): 271-274; Luo, Methods Mol Biol. 2012; 822:183-8).

Any method known to those in the art can be employed for determining the level of protein. Methods for assaying for a protein include but are not limited to Western blot, immunoprecipitation, immunoassay, immunohistochemistry, immunofluorescence and radioimmunoassay. The proteins analyzed may be localized intracellularly (most commonly an application of immunohistochemistry) or extracellularly.

The identification of biomarkers of the present invention may be accomplished using various suitable assays. A suitable assay may include one or more of a chemical assay, an enzyme assay, an immunoassay, mass spectrometry, chromatography, electrophoresis, a biosensor, an antibody microarray or any combination thereof. Most commonly if an immunoassay is used it may be an enzyme-linked immunosorbant assay (ELISA), a sandwich assay, a competitive or a non-competitive assay, a radioimmunoassay (RIA), a lateral flow immunoassay, a Western Blot, an electro-chemilumescent assay, a magnetic particle assay, an immunoassay using a biosensor, a bead-based array assay (e.g. Luminex, Milliplex or Bioplex), a multiplex aptamer-based assay (e.g. SOMAscan), an immunoprecipitation assay, an agglutination assay, a turbidity assay or a nephelometric assay.

In certain embodiments, upregulation of RNA or protein level includes an increase above a baseline level of 1-, 2-, 3-, 4-, 5-, 6-, 7-, 8-, 9-, 10-, 11-, 12-, 13-, 14-, 15-, 16-, 17-, 18-, 19-, 20-fold, or more and any and all partial integers therebetween. In other embodiments, downregulation of RNA or protein level includes a decrease below a baseline level of 1-, 2-, 3-, 4-, 5-, 6-, 7-, 8-, 9-, 10-, 11-, 12-, 13-, 14-, 15-, 16-, 17-, 18-, 19-, 20-fold, or more and any and all partial integers therebetween.

In certain embodiments, the presence of at least one of the RNA or protein biom.arkers of the present invention allows a diagnosis or prognosis of bone healing ability with a sensitivity and/or specificity of at least 50%, at least 60%, at least 70%, at least 80%, at least 90%, at least 95% or at least 99%.

In certain embodiments, the level of expression is determined using log-transformed RNA or protein levels. The log transformation of RNA or protein levels substantially reduces the positive skew in the data. In certain embodiments, the level of expression is determined using log-transfortned RNA or protein levels relative to a normalizing RNA or protein level.

In certain embodiments, for interpretation of quantitative nucleic acid or protein expression measurements, a normalizer may be needed to correct expression data for differences in sample input, RNA or protein quality, reverse transcription (RT) efficiency, and other assay efficiencies between samples. In certain embodiments, to accurately assess whether increased or decreased RNA or protein is significantly different, the RNA or protein expression can be normalized to accurately compare levels of expression between samples, e.g., a control level is used to adjust the RNA or protein expression measurement. In quantitative assays, such as for example, reverse transcription quantitative real-time PCR (RT-qPCR), normalization can be performed using spiked-in markers or endogenous markers as controls for the expression level of a RNA under investigation. Normalization includes rendering the measurements of different arrays or PCR or in particular RT-qPCR experiments comparable by reducing or removing the technical variability. Within these experiments there exists a multiplicity of sources capable of falsifying the measurements. Possible technical sources of interference are: different efficiency in reverse transcription, labeling or hybridization reactions, as well as problems with the arrays, batch effects in reagents, or lab-specific conditions. By normalization a more robust detection of RNA expression can occur. Typically, RNA (mRNA, ncRNA or miRNA) normalization involves use of spiked-in markers that have known input abundances that are correlated to the observed fractional cycle number or detection threshold crossing point of an RT-qPCR assay. A spiked-in marker exhibits minimum change of abundance across different RNA samples and thus serves as a control for the technical sources of variation in measurements across different samples. RNA normalization may also involve the use of one or more endogenous RNAs that naturally occur in all subjects' samples. An endogenous control marker exhibits minimum change of abundance across RNA samples from normal, slow and nonunion healing abilities and thus serves as a control for the biological sources of variation in measurements across different samples, such as the subject's overall production of RNA and the efficiency of RNA extraction from the subject's samples. Multiple spiked-in markers, endogenous markers, or markers from both classes may be used separately or combined during the normalization adjustments of an RNA expression measurement.

In certain embodiments, to characterize the bone healing ability in an acutely injured subject, the level of RNA or protein expression in a sample taken from the subject is compared to a reference sample or set of samples by computational methods known to those skilled in the art. Non-limiting examples of computational and statistical methods comprise pairwise and multi-class ANOVA tests, Partek ANOVA t-tests and Extraction of Differential Gene Expression (EDGE) to test for statistically significant differences between the acutely injured subject and previously measured populations of subjects with normal, slow or nonunion healing ability.

In yet another aspect, the invention provides a score or composite score that can be used to characterize the bone healing ability in an acutely injured subject. In another aspect, the invention provides a score or composite score that can be used to characterize the bone healing ability in a nonunion subject before or after a nonunion-mitigating intervention, For example, the expression levels of at least 2 biomarkers in a sample taken from the subject are compared to the expression levels of the at least 2 biomarkers in one or more reference samples. The ratio of expression level of each biomarker in the subject's sample in relation to the reference sample(s) is then multiplied by an independently selected multiplying factor. The resulting values are combined as to arrive at the score or composite score useful to characterize the bone healing ability in the subject. The score or composite score may be derived from the same or different RNA or protein biomarkers measured at one or more times, from biomarker(s) change(s) between two or more times, or any combination thereof. The score or composite score may be indicative of AInorm, AIslow, AInu or AInotnorm healing ability after acute injury, or no or slow healing or successful healing before or after a nonunion-mitigating intervention.

Compositions:

In certain embodiments, the invention includes a set of preferred probes or primers, either labeled (e.g., fluorescer, quencher, and so forth) or unlabeled, that are useful for detecting or predicting or monitoring the ability of normal healing, slow healing or no healing of a fractured bone in a subject.

In certain embodiments, a plurality of RNAs is selected from the group consisting of SEQ ID NOs: 1, 2, 4-7, 24, 53, 64, 75, 78, 89, 103, 104, 109, 126, 132, 134, 189, 191, 194, 219, 222, 228, 239, 270, 279, 283, 290, 291, 293, 299, 344, 347, 349, 371, 388, 400, 401, 413, 442, 449, 459, 471, 512, 516, 518, 519, 520, 522, 523, 525, 527-529, 531, 533, 534, 539, 541, 543, 548-552, 556, 562, 572, 582, 599, 618, 652, 653, 655, 656, 698, 702, 703, 722, 814, 844, 864, 885, 889, 914, 938, 954, 966, 985, 996, 1054, 1074, 1126, 1153, 1154, 1286, 1501, 1512, 1515, 1526, 1528, 1529, 1542, 1546-1548, 1555, 1561, 1562, 1568, 1584, 1597, 1605, 1607, 1610, 1627, 1637, 1649, 1652, 1662, 1665, 1677, 1832, 1834-1836 and 1838. In other embodiments, a plurality of RNAs is selected from the group consisting of SEQ ID NOs: 1-1684 and 1830-1838. In yet other embodiments, a plurality of polypeptides (or proteins) is selected from the group consisting of SEQ ID NOs: 1685-1829.

In certain embodiments, specific probe sets comprise probes that are capable of detecting at least one RNA selected from the group consisting of SEQ ID NOs: 1, 2, 4-7, 24, 53, 64, 75, 78, 89, 103, 104, 109, 126, 132, 134, 189, 191, 194, 219, 222, 228, 239, 270, 279 283, 290, 291, 293, 299, 344, 347, 349, 371, 388, 400, 401, 413, 442, 449, 459, 471, 512, 516, 518, 519, 520, 522, 523, 525, 527-529, 531, 533, 534, 539, 541, 543, 548-552, 556, 562, 572, 582, 599, 618, 652, 653, 655, 656, 698, 702, 703, 722, 814, 844, 864, 885, 889, 914, 938, 954, 966, 985, 996, 1054, 1074, 1126, 1153, 1154, 1286, 1501, 1512, 1515, 1526, 1528, 1529, 1542, 1546-1548, 1555, 1561, 1562, 1568, 1584, 1597, 1605, 1607, 1610, 1627, 1637, 1649, 1652, 1662, 1665, 1677, 1832, 1834-1836 and 1838 for detecting or predicting or monitoring normal healing, slow healing or no healing of a fractured bone in a subject.

In certain embodiments, specific probe sets comprise probes that are capable of detecting at least one RNA selected from the group consisting of SEQ ID NOs: 1-1684 and 1830-1838.

In certain embodiments, a plurality of polypeptides (or proteins) selected from the aroup consisting of SEQ ID NOs: 1685-1829.

In yet other embodiments, the invention includes a set of preferred probes or primers, either labeled (e.g., fluorescer, quencher, and so forth) or unlabeled, that are useful for detecting or predicting or monitoring the ability of normal healing or slow healing of a nonunion fractured bone in a subject after a nonunion-mitigating treatment.

In certain embodiments, a plurality of RNAs is selected from the group consisting of SEQ ID NOs: 5, 109, 270, 283, 299, 344, 349, 371, 516, 534, 618, 702, 703, 814, 864, 889, 966, 985, 996, 1074, 1126, 1501, 1515, 1526, 1528, 1529, 1547, 1548, 1555, 1561, 1568, 1597, 1607, 1637, 1649, 1652, 1665, 1677, 1832, 1834, 1835, 1836 and 1838.

In other embodiments, specific probe sets comprise probes that are capable of detecting at least one RNA selected from the group consisting of SEQ ID NOs: 5, 109, 270, 283, 299, 344, 349, 371, 516, 534, 618, 702, 703, 814, 864, 889, 966, 985, 996, 1074, 1126 1501, 1515, 1526, 1528, 1529, 1547, 1548, 1555, 1561, 1568, 1597, 1607, 1637, 1649, 1652, 1665, 1677, 1832, 1834, 1835, 1836 and 1838 to measure the ability of normal healing or slow healing of a nonunion fractured bone in a subject after a nonunion-mitigating treatment.

In certain embodiments, the invention includes a set of preferred antibodies, RNA aptamers, or other protein binding molecules, either labeled or unlabeled, that are useful for detecting or predicting or monitoring the ability of normal healing, slow healing or no healing of a fractured bone in a subject.

In certain embodiments, a plurality of polypeptides or proteins is selected from the group consisting of ACY1, AMH, AMHR2, APOA1, BDNF, C1S, C2, CASP2, CAST, CCL15, CD209, CGA/TSHB, CST5, CTSA, CXCL2/CXCL3, CXCL6, DMP1, DSG2, EPHA1, EREG, ESAM, FAM107A, FCGR2A/FCGR2B, FCN2, FCRL3, FGF23, FGF4, FGF8, FGFR3, GAS1, GP6, GPC5, GZMCB2, HSPA8, ICAM3, IFNA2, IGHG1/IGHG2/IGHG3/IGHG4, IL12RB1, IL1RAPL2, IL20, LDHB, LEPR, LIN7B, LYVE1, MMP1, NCF, NGF, NTN4, OMD, PDE7A, PGD, PGLYRP1, PLG, PRLR, PRSS3, PTK6, PYY, RETN, SLC25A18, SPINT2, SPOCK2, TGFB2, TGFBI, TIMP1, TNF, TNFRS14, INFRS17, TNFRSF13C, and VWF.

In certain embodiments, a plurality of polypeptides or proteins is selected from the group consisting of ACY1, AMH, AMHR2, APOA1, BDNF, C1S, C2, CASP2, CAST, CCL15, CD209, CGA/TSHB, CST5, CTSA, CXCL2/CXCL3, CXCL6, DMP1, DSG2, EPHA1, EREG, ESAM, FAM107A, FCGR2A/FCGR2B, FCN2, FCRL3, FGF23, FGF4, FGF8, FGFR3, GAS1, GP6, GPC5, GZMCB2, HSPA8, ICAM3, IFNA2, IGHG1/IGHG2/IGHG3/IGHG4, IL12RB1, IL1RAPL2, IL20, LDHB, LEPR, LIN7B, LYVE1, MMP1, NCF, NGF, NTN4, OMD, PDE7A, PGD, PGLYRP1, PLG, PRLR, PRSS3, PTK6, PYY, RETN, SLC25A18, SPINT2, SPOCK2, TGFB2, TGFBI, TIMP1, TNF, TNFRS14, TNFRS17, TNFRSF13C, and VWF.

Kits

In certain embodiments, kits are provided. Commercially available kits for use in these methods are, in view of this specification, known to those of skill in the art. In general, kits will comprise a detection reagent that is suitable for detecting the presence of a polypeptide or nucleic acid, or RNA of interest.

In other embodiments, there is a panel of probe sets. Preferred probe sets are designed to detect expression of one or more RNAs or protein and provide information about the bone healing ability in an acutely injured subject. Probe sets are particularly useful because they are smaller and cheaper than probe sets that are intended to detect as many mRNAs, ncRNAs, miRNAs and proteins as possible in a particular genome. The probe sets are targeted at the detection of mRNAs, ncRNAs, miRNAs and proteins that are informative about diagnosis or prediction of normal, slow or no bone healing ability in an acutely injured subject. Probe sets may also comprise a large or small number of probes that detect RNAs or proteins that are not informative about bone healing ability in an acutely injured subject. Such probes are useful as controls and for normalization (e.g., spiked-in and endogenous markers). Probe sets may be a dry mixture or a mixture in solution. In certain embodiments, probe sets can be affixed to a solid substrate to form an array of probes. It is anticipated that probe sets may also be useful for multiplex PCR. The probes may be nucleic acids (e.g., DNA, RNA, chemically modified forms of DNA and RNA), LNAs (locked nucleic acids), or PNAs (peptide nucleic acids), amino acids, peptides, antibodies or any other polymeric compound capable of specifically interacting with the desired nucleic acid or amino acid sequences.

It is contemplated that kits may be designed for isolating and/or detecting RNA or protein in essentially any sample (e.g. blood, urine, and so forth), and a wide variety of reagents and methods are, in view of this specification, known in the art.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the experiments disclosed herein are now described.

Materials and Methods

Patient Enrollment:

Patients in the University of Pennsylvania Orthopaedic Trauma and Fracture Service, and healthy volunteers, were evaluated for inclusion/exclusion criteria and enrolled in an ongoing study approved by the Penn Institutional Review Board. Adult skeletally mature human subjects (age 18 or older) from three clinical categories (healthy, acute injury, and chronic nonunion) were recruited for this investigation. Healthy subjects were eligible if they had not suffered a fracture within 12 months of enrollment, and any prior fracture had healed completely in a normal time period. Acute injury subjects who underwent an inpatient stay provided blood samples once per day for up to 10 days while hospitalized, and nonunion subjects were enrolled and provided samples upon diagnosis. Additional blood samples from the same patients were collected during follow-up clinical visits.

RNA Extraction:

Whole blood collected in PAXgene Blood RNA tubes was processed according to the vendor's protocol (PreAnalytiX/Qiagen, Valencia Calif., USA) for purification of total RNA including miRNA. RNA quality and quantity were assessed by spectrophotometry, fluorometry (Qubit RNA HS, Life Technologies, Grand Island N.Y., USA) and Bioanalyzer RNA LabChips (Agilent Technologies, Santa Clara Calif., USA).

RNA Profiling by Microarrays:

RNA assays were conducted according to the vendors' instructions in the Penn Molecular Profiling Facility. Transcriptome amplification was perthrmed with 50 ng of total RNA using the Ovation WT Pico kit (NuGEN Technologies, San Carlos Calif., USA), providing linear expansion of all transcripts without interference from ribosomal or globin RNAs. The resulting cDNA was labeled with biotin and hybridized to Human Gene 2.0ST Arrays (Affymetrix, Santa Clara Calif., USA). Separately, 500 ng of total RNA was labeled with biotin using the FlashTag Biotin HSR kit (Affymetrix) for miRNA hybridization to GeneChip miRNA 4.0 Arrays (Affymetrix).

Microarray Data Analysis:

mRNA and miRNA data sets were independently analyzed using Partek Genomics Suite (Partek, St. Louis Mo., USA).

After normalization by the RMA algorithm (Irizarry et al., Biostatistics 2003; 4 (2):249-264) and log2 transformation, pairwise and multi-class ANOVA tests with multiple testing correction were used to identify ilaicroarray probesets that displayed differences between each clinical condition: acute injury which healed in a normal time (AInorm), healed slowly (AIslow), or did not heal and was later diagnosed as a nonunion (AInu). Thresholds for designating a difference as statistically significant were a p-value less than 0.05 and absolute value of signal fold-difference greater than 1.5. Normalized data outputs from the SomaScan serum protein assay (SomaLogic, Boulder Colo., USA) were similarly analyzed using Partek Genomics Suite. Gene lists were analyzed for enrichment of biological process categories using DAVID tools (Huang da et al., NatProtoc 2009; 4 (1):44-57; Huang da et al., Nucleic Acids Res 2009; 37 (1):1-13).

Protein Profiling:

Whole blood collected in BD Vacutainer Serum Separation Tubes (Fisher Scientific, Pittsburgh Pa., USA) was processed according to the manufacturer's instructions and the aliquoted serum samples were flash frozen before storage at −80° C. Serum samples were submitted to Soma-Logic, Inc. (Boulder Colo., USA) for protein screening using the SOMAscan assay (www.somalogic.com). Normalized data outputs from the SOMAscan assay were analyzed using Partek Genomics Suite using the same statistical approach described for microarray data.

Biomarker Panel Development:

Development of custom RNA biomarker panels and methods for high-throughput RT-qPCR screening are described in Baldwin et al. (J. Biomol. Tech. 2016; in press). Microarray data were analyzed for differential RNA expression between patients in different clinical categories. Biomarker candidates were ranked by false discovery rate adjusted p-values after multi-class ANOVA, and included 30 long mRNAs, 12 long noncoding RNAs, 22 microRNAs, and 5 short noncoding RNAs. The "short" class includes small nuclear and nucleolar RNAs (snRNA, snoRNA) that are typically longer than microRNAs and can be reverse transcribed by random priming. Two endogenous reference targets were added to the panel, human TBP for mRNA and RNU6-6P for short RNA, as well as two synthetic spike-in references, lacZ in *E. coli* plasmid pUC19 (New England BioLabs, Ipswich Mass., USA) and an oligonucleotide for human miRNA hsa-miR-450a-5p (IDT Integrated DNA Technologies, Coralville Iowa, USA). miR-450a-5p was chosen as a synthetic reference because it had not been detected in any of the blood RNA samples screened by microarrays. For RT-qPCR detection of the 73 targets, 60 TaqMan assays were ordered (Thermo Fisher Scientific) and 13 custom primer pairs with hydrolysis probes incorporating 5' 6-FAM/ZEN and 3' Iowa Black fluorescence quencher were synthesized (IDT).

Reverse Transcription:

These and subsequent reactions were assembled in 8-tube strips or 96-well plates by multi-channel pipetting, and performed in a PTC 225 Tetrad Thermal Cycler (MJ Research, now Bio-Rad Laboratories, Hercules Calif., USA). Long RNA targets were reverse transcribed by random priming, using up to 750 ng of total RNA and the High Capacity cDNA Reverse Transcription Kit (4374966, Thermo Fisher Scientific). A reaction master mix was assembled and added to each RNA sample along with sufficient water for a final volume of 10 ul, followed by incubation in a thermal cycler at 25° C. for 10 min, 37° C. for 120 min, 85° C. for 5 min and hold at 4° C. A no-template control (long NTC) that contained no RNA was included among these reverse transcription reactions.

miRNA targets were reverse transcribed with a pool of the RT primers taken from TaqMan Small RNA Assays (Thermo Fisher Scientific) and up to 350 ng of total RNA using the TaqMan MicroRNA Reverse Transcription Kit (4366596, Thermo Fisher Scientific). A reaction master mix was assembled, spiked with 0.05 fmole/reaction synthetic miR-450a-5p, and added to each RNA sample along with sufficient water for a final volume of 12 ul. Reactions were held on ice for at least 5 min, followed by incubation in a thermal cycler at 16° C. for 30 min, 42° C. for 30 min, 85° C. for 5 min and hold at 4° C. A micro-NTC that contained no sample RNA was included among these reverse transcription reactions. cDNA products from long and short RNA reverse transcription were stored at −20° C.

Pre-Assay cDNA Amplification:

Custom synthesized primer and probe oligonucleotides were combined in TE buffer to create assay mixes for each target, containing 18 uM of each of the two primers and 5 uM of the hydrolysis probe (equivalent to a 20× TaqMan assay mix). A diluted primer pool was created (also containing probes) by combining 10 ul of each long RNA assay and 6 ul of each miRNA assay for all targets in the panel. The resulting concentration of each assay was determined, and used to calculate the dilution factor necessary for a final concentration of 0.05× for long RNA primers and 0.03× for miRNA primers. cDNA amplifications were performed in 7 ul reactions using TaqMan PreAmp Master Mix (Thermo Fisher Scientific), 1.1 ul of the primer pool, 1.2 ul of long cDNA or reverse transcription long NTC and 1.2 ul of micro-cDNA or reverse transcription micro-NTC. The thermal cycler program was 95° C. for 10 min, 55° C. for 2 min and 72° C., for 2 min, followed by 15 cycles of 95° C. for 15 sec and 60° C. for 4 min, and completed with 99.9° C. for 10 min and hold at 4° C. A 5 ul aliquot of the amplification product was archived at −20° C. The remaining 2 ul were mixed with 29 pg of pUC19 (2 ul), and 16 ul of TE buffer was added to dilute the amplified cDNA 1:10 before storage at −20° C.

Quantitative PCR:

Real-time, quantitative fluorescence detection of PCR products was performed in a Fluidigm system consisting of a BioMark HD instrument, IFC MX and HX Controllers, and 48×48 or 96×96 Dynamic Arrays using the manufacturer's protocols for standard TaqMan assays (PN 68000089 H1, 68000130 D1 and 68000088 J1, Fluidigm, South San Francisco Calif., USA). A pilot 48×48 array (Fluidigm integrated fluidic circuit, IFC) tested a subset of the target panel, 47 amplified cDNA samples, and one NTC from pre-assay amplification. A set of 285 amplified cDNA samples (including the pilot 47, IFC 2-4), and a subsequent set of 631 amplified cDNA samples (including all previous samples, IFC 5-25), were assayed on 96×96 arrays with an NTC on each array. Assays on these arrays included "panel 1": the pilot 48 target panel supplemented with 25 additional candidate RNA biomarkers (IFC 5-11), or a separate "panel 2" of 192 candidate RNA biomarkers (IFC 12-25).

RT-qPCR Data Analysis:

BioMark HD data processing parameters were Linear (Derivative) for the baseline correction method and Auto (Global) for the Ct threshold method, software version 4.1.3. Technical performance was assessed using the Ct Value column from BioMark HD output tables (rawCt). RawCt values of 38 or higher were designated as no detection. Targets with rawCt<38 in at least 90% of cDNA samples were designated as consistently detected. Biomarker expression was normalized to reference genes by the ΔCt method (normCt) (Schmittgen T D and Livak K J, Nat Protoc 2008; 3 (6):1101-1108) and transfotmed to linear scale before statistical testing. ANOVA t-tests in Partek Genomics Suite (Partek, St. Louis Mo., USA) were used to test for likelihood of differences between healing outcome classes, and the significance threshold was set at 0.05 for unadjusted p-values and the stepup false discovery rate (FDR, an adjusted p-value incorporating multiple test correction).

The results of the experiments are now described in the following examples.

Example 1: Patient Demographics and Clinical Outcomes

Study enrollments include 127 acute injury (AI) subjects admitted to the hospital for bone fracture(s), 35 nonunion (NU) patients diagnosed with little to no healing of a fracture that occurred six to nine months before entering the study, and 56 healthy volunteers (HV). Subject age, gender, race/ethnicity and fracture locations are summarized in FIG. 17 in U.S. Provisional Patent Application No. 62/283,443. Approximately 64% of AI patients healed their fractures in a normal time (AI norm), while 7% reached a clinical diagnosis of nonunion (AI nu). The remaining 29% of AI subjects have been classified as slow healers (AI slow) that either resolved their fracture after substantially delayed healing or continue in the study with ongoing monitoring for suspected nonunion. Healing outcomes for NU patients after diagnosis and therapy for nonunion included successful healing (NUhealed) or no or slow healing (NUslow).

Example 2: Global RNA Screening to Identify Panel 1 Biomarkers

As a preliminary screen to characterize blood samples obtained soon after the study was opened, microarray hybridizations were performed to quantify the expression levels of all annotated human genes and microRNAs. Multiple samples from each of seven AI patients and two NU patients were used, along with samples from two of the AI patients taken after their fractures had healed. The resulting RNA profiles were compared to blood RNA expression levels in 23 HV. Principal component analysis indicated that summarized mRNA expression patterns distinguish AI and NU samples from HV, and post-healing samples from AI patients produced profiles more like HV than the within-subject counterparts collected soon after fracture (FIG. 1A in U.S. Provisional Patent Application No. 62/283,443). Global miRNA profiles did not separate AI from HV samples, but NU samples formed a clearly distinct cluster (FIG. 1B in U.S. Provisional Patent Application No. 62/283,443).

Multi-class and pairwise ANOVA with correction for multiple testing was used to identify RNAs with significantly different blood expression levels in the microarray data sets. At a fold-difference threshold of 1.5 and false discovery rate <10%, 508 mRNAs were altered in samples from AI only, AI and NU, or NU only compared to HV (FIGS. 18-20 in U.S. Provisional Patent Application No. 62/283,443).

A similar data analysis strategy was used for miRNA array data, and identified 34 miRNAs that were differentially expressed in AI only or NU only compared to HV (FIGS. 22-23 in U.S. Provisional Patent Application No. 62/283, 443).

As predicted by principal components analysis, the lists of AI and NU genes that are significantly different from HV include a shared but small subset, and the AI and NU micmRNA sets have no overlap (FIG. 1C in U.S. Provisional Patent Application No. 62/283,443). No RNAs from the healed fracture samples were significantly different from HV. Lists of AI and NU candidate biomarker mRNAs derived with a higher significance threshold (false discovery rate <5%) were used for over-representation analysis of Gene Ontology biological process categories. Seventeen biological processes are enriched with statistical significance among the biomarker mRNA annotations, and the process categories are for the most part unique to AI or NU. Acute injury genes are predominantly involved in immune and wound responses, while nonunion genes are distributed into more generalized categories for macromolecular metabolism and transport (FIG. 25 in U.S. Provisional Patent Application No. 62/283,443).

Example 3: Healing Time Course Profiling of Panel 1 RNA Biomarkers

The preliminary microarray screening produced three classes of potential biomarkers: AI-only, which are over- or under-expressed compared to HV in the week following fracture, may return to HV levels with healing, and may show delayed changes in patients with slow or no healing; NU-only, which are not different from HV immediately after injury but become different at some later time, perhaps only in nonunion cases, and AI+NU, which are different from HV after injury and may have divergent expression profiles during normal vs. slow/no healing. Candidate RNA biomarkers were therefore selected for RT-gPCR profiling of AI blood prospectively collected throughout the healing time course.

Blood samples from 88 AI subjects who were not included in the microarray screening (FIG. 17 in U.S. Provisional Patent Application No. 62/283,443) generated 240 RNA samples distributed over seven or more months of healing and divided into eight time periods (FIG. 2A in U.S. Provisional Patent Application No. 62/283,443). Subject enrollments and fracture locations were evenly distributed across calendar months and weather seasons (FIG. 13A-13B in U.S. Provisional Patent Application No. 62/283,443). To control for variations in input RNA and reaction efficiency, each RT-qPCR assay was normalized to endogenous TBP mRNA levels or RNU6-6P short RNA levels in each sample. Samples were also spiked with synthetic templates for the *E. coli* lacZ gene and human miR-450a-5p, a microRNA not detected by microarrays in any of the previously profiled blood samples. RT-qPCR data for these four controls showed no significant differences across time or between subject categories which would introduce artifactual changes in normalized biomarker profiles (FIG. 2B in U.S. Provisional Patent Application No. 62/283,443). The multi-class ANOVA p-values for differences between time periods or patient outcomes, or a time and outcome interaction, were respectively 0.98, 0.77 and 0.47 for TBP, 0.84, 0.62 and 0.34 for lacZ, 0.85, 0.58 and 0.50 for RNU6-6P, and 0.83, 0.68 and 0.19 for miR-450a-5p.

Data for 47 mRNAs and 27 miRNAs were tested by ANOVA in two analysis strategies. First, average expression levels were calculated for all AI norm, AIslow and AInu samples within a time period and tested for significant differences (p<0.05) between AI outcome categories. A second analysis was performed by determining the within-subject change in expression over various time intervals, calculating the average change across patients in each AI category, and testing each time interval for significant differences between categories. Test results were then summarized in plots of average expression levels (normalized cycle threshold, Ctn) at each time period for AInorm and AIslow (linear scale fold-difference=2^[Ctn difference]). Six AI patients, five of whom provided samples during more than one time period, were later diagnosed with nonunions, and individual data points for these AI nu samples were overlayed on the summary plots (FIGS. 3-4 in U.S. Provisional Patent Application No. 62/283,443). Some candidate biomarkers showed significant differences early or late in the time course (reflecting the design of the microarray screening experiment), but had generally similar profiles over healing time. However, 37 mRNAs (FIG. 1) and 18 miRNAs (FIG. 2) were differentially expressed between AI slow and AI norm at one or more time periods, often during or before the fourth month of healing. Some of these RNAs were also different in AI nu compared to AI norm at time periods 1a, 4 or 7 (which had sufficient AI nu samples to power ANOVA tests), and ARPP19 and several miRNAs could discriminate AI nu from AI slow.

Many RNA expression levels naturally vary across the human population, so averages within a healing time period may be difficult to translate into prognostic biomarkers applicable to individual patients if their baseline expression starts at an outlier value. Within-subject between-time analyses control for such variation by measuring the direction and magnitude of change, metrics that are independent of the expression levels' distances from population averages. Each patient's RNA expression changes were measured over a variety of time intervals, and the average fold-change was calculated for each subject category. Twenty-eight mRNAs changed during one or more intervals in the first four months of healing and had average changes that were significantly different comparing AInorm to AIslow (FIG. 3). FIG. 4 describes a similar analysis fiver miRNAs, five of which had different profiles in AInorm vs. AIslow within the first three months of healing. Overall expression behavior across a time course can be modeled using spline-based methods (Storey et al., Proc Natl Acad Sci USA 2005; 102 (36):12837-12842), so the EDGE analysis tool was applied to test for profile differences between AInorm and AIslow. Five mRNAs (IL2RB, FAM83A, LDHB, IRF8, IFIT1B) and two miRNAs (hsa-miR-1255b-5p, hsa-miR-664a-5p) were significantly different with EDGE p-values ranging from 0.014 to 0.052.

Examination of the profile summary graphs for all RNAs tested revealed notable patterns. Average mRNA levels for ANKRD22, ANXA3 and LDHB appear to cycle between low and high amounts over time in AI norm, and the cycle phasing is offset by one to two months in AI slow. The RNA from which the miR-29 precursor stem-loop is cleaved was consistently elevated in AIslow and AInu compared to AInorm, and its mature product hsa-miR-29a-3p was detected at higher levels in AI than HV by microarrays (FIG. 22 in U.S. Provisional Patent Application No. 62/283,443). Other mature miRNAs such as hsa-miR-1270 and hsa-miR-18a-5p were significantly different between AIslow and AInorm at early time periods, and had diminished or missing changes in AIslow during the time intervals that showed more dynamic expression in AInorm. Three miRNAs, hsa-let-7f-5p, hsa-miR-1228-5p and hsa-miR-182-3p, demonstrated large and sustained differences between AIslow and AInorm and/or large differences between AInu and AInorm. The average values for these miRNAs were heavily influenced by lack of detection at any measurable amount in a number of blood samples, suggesting "on or off" expression states. The data were therefore transformed into binary classes of detected (at any level) or undetected for each sample, and subjects were similarly classified by detection (in at least one sample from any time) or no detection. Chi-square tests were then performed for differences in the outcome distributions of these binary classes (FIG. 5). Detection rates for miR-182-3p were significantly different (p<0.05) in all AI subjects vs. HV, but significance was lost at the sample level because most AI subjects had expression in only one or a few of their samples. Subjects and samples were both significantly different between AInorm and AIslow for miR-1228-5p detection, with expression occurring more often in AIslow. Detection rates were not as dramatically different among samples for hsa-let-7f-5p and detection occurred more often in AInorm, but all AI subjects combined were much more likely to show let-7f expression than were HV.

Biomarker panel 1 targets were also measured by RT-qPCR in fracture patients after they were diagnosed with nonunion and received an initial therapeutic intervention. Twelve mRNAs and one miRNA were expressed at significantly different levels in blood from NUslow subjects compared to NUhealed subjects (FIG. 6).

The average AInorm expression levels for sixteen miRNAs produced time course profiles that share an "M" shape, centered around healing month four (FIG. 5 in U.S. Provisional Patent Application No. 62/283,443). While individual miRNAs have different magnitudes of change, the general pattern suggests early increases of expression between time periods 1a and 1b, followed by reductions to levels at or below the starting point, and then a second increase/decrease cycle around time period 6. The "M" profiles are flattened in AIslow, with early increases that persist into months two and three and overall expression levels that remain elevated relative to their starting points.

Example 4: Interpretation and Use of Panel 1 RNA Biomarkers

Interpretation of long-term time course data collected from human subjects can be challenging due to the many environmental, genetic and epigenetic variables that may affect a phenotype, and due to the inability to control, or even account for, these variables. Blood RNA biomarkers that appear to cycle in abundance with periodicities of one or more months were observed. Circadian rhythm genes are perhaps the best-characterized time-related molecular system in humans, but most patient samples were drawn during appointments scheduled throughout normal business hours on weekdays and this system seems unlikely to have influenced the fracture healing biomarkers. The menstrual cycle roughly operates with monthly periodicity, but no gender effect was observed in data analyses and synchronized menstruation among AInorm patients but different from AIslow patients is also unlikely. The sole synchronizing event experienced by all of the AI patients was bone fracture, and the fractures occurred throughout the range of seasonal conditions typical for the Northeast region. If fracture healing outcomes were influenced by season (e.g. ice slip and fall, reduced exercise in winter, organized sports schedules), the dates of injury and healing might be biased toward different months among AInorm vs. AIslow, but this was not observed (FIG. 13A in U.S. Provisional Patent Application No. 62/283,443). The months in which blood samples were drawn also appear to have similar distributions for AI norm and AI slow (FIG. 13B in U.S. Provisional Patent Application No. 62/283,443), as do gender, age and race (FIG. 17 in U.S. Provisional Patent Application No. 62/283,443).

RNA biomarker candidates were chosen after microarray screening of blood samples taken soon after injury or after chronic non-healing compared to healthy volunteers. RT-qPCR time course profiling mostly confirmed differences from the HV average at time periods 1a or 7, but expression levels across time were within the same range observed for HV. This might be expected for RNAs that naturally cycle; a group of randomly sampled, unsynchronized HV should produce levels that reflect the cycle's amplitude range, and the difference between AInorm and AIslow is less due to aberrant magnitudes of expression and more influenced by altered timing after injury. Other RNAs (ANKRD22 and ANXA3 in AInu, miR-182-3p in all AI) had expression levels outside the HV range and may reflect injury-specific responses. Without wishing to be limited by any theory, in either case, altered tuning or induced/repressed expression may be the result of transcription regulation mechanisms that could be investigated by promoter analyses of the genes reported here. Without wishing to be limited by any theory, miRNAs may also be subject to regulatory events that coordinate expression after fracture, including precursor transcript production, splicing and maturation, and perhaps release into blood as extracellular RNA. Without wishing to be limited by any theory, one or more of these mechanisms may be altered in patients who heal slowly, and for some RNAs it appears that nonunion is a condition distinct from both normal and slow healing.

Time course profiling of miR-27a-3p confirmed that early expression in AInorm and AIslow was higher than in HY and indicated that during healing week 1, miR-27a-3p was lower in AIslow than in AInorm but became higher than AInorm in months 2 and 3 (FIG. 2). The miR-23a-27a-24-2 cluster inhibits osteoblast differentiation, so the initial induction observed in response to injury may repress normal osteoblast differentiation, allowing a pool of precursor cells to accumulate and be recruited to the fracture site. Subsequent drops in miR-27a-3p levels would release this repression and promote differentiation at the fracture where osteoblasts are needed, and this process is delayed or attenuated in slow healers. Similarly, miR-93-5p inhibits osteoblast differentiation and showed less expression in AIslow than AInorm at week 1 but greater expression in month 7.

This invention is the first to prospectively profile patients' blood RNA collected during the bone fracture healing time course. The resulting candidate biomarkers for rate of healing can now be examined for prognostic efficacy, whether individually, in combined biomarker panels, or integrated with other biochemical or clinical metrics. For example, discrimination of AIslow from AInorm is demonstrated using a score that combines LDHB and ANXA3 expression measures (FIG. 6A in U.S. Provisional Patent Application No. 62/283,443). This score incorporates within-patient changes in expression over time, an attractive strategy that avoids comparison of a patient's data to the population averages of unrelated people. However, comparisons of averages can also be useful, especially for biomarkers that exhibit detected/undetected states and as shown for the combination of pre-miR-29 and miR-1228-5p to discriminate AI nu from AI norm (FIG. 6B in U.S. Provisional Patent Application No. 62/283,443). The utility of the candidate biomarkers may extend to related applications; RT-qPCR profiling of NU at enrollment and after revision therapy suggests that a score combining ANXA3 and miR-182-3p expression levels can discriminate nonunion patients who will heal their fractures from those who will continue to experience slow or no healing (FIGS. 6C-6D in U.S. Provisional Patent Application No. 62/283,443).

Orthopaedic genomics studies and the availability of RNA or protein biomarkers should improve test performance, as would integration with clinical measures (for example hospital length-of-stay for AI, FIG. 17 in U.S. Provisional Patent Application No. 62/283,443) and advanced imaging. The biomarkers of the present invention allow an early assessment of risk for nonunion, especially those with signals within the first two months of healing, and offer a means to more rapidly evaluate how well new drugs or therapeutic treatments are promoting positive healing outcomes.

Example 5: Global RNA and Protein Screening to Identify Panel 2 Biomarkers

RNA and proteins circulating in blood were prospectively collected from patients with recent fractures, and screened for differences between subjects who healed normally and those who showed delayed healing or were later diagnosed with nonunion. Twenty-four serum samples from 12 subjects were tested, as were 51 RNA samples from 21 subjects. Twenty-five serum proteins, 213 microRNAs, and 915 mRNAs (857 genes) were identified by SomaLogic SOMAscan protein profiling or Affymetrix GeneChip microarray RNA profiling respectively. The biomarkers exhibited differences between patient outcomes within one or more healing times, and/or differences in the abundance changes that occur between healing times. See FIG. 7, as well as U.S. Provisional Patent Application No. 62/231,935 and U.S. Provisional Patent Application No. 62/283,443, for further details on the data and annotations of these biomarkers.

Example 6: Healing Time Course Profiling of Panel 2 RNA Biomarkers

Reverse transcription quantitative PCR (RT-qPCR) was completed for a subset of candidate RNA biomarkers discovered by microarray screening described herein. These results used an independent measurement method to confirm the differences in blood RNA abundances between fracture healing outcomes initially observed by microarray assays, and extended the findings to additional patient samples. RT-qPCR assays for 122 mRNAs, 18 long noncoding RNAs, 7 short noncoding RNAs, and 111 microRNAs were performed on each of the blood RNA samples recited in FIG. 8.

Of the 258 biomarker RNAs tested, 234 showed a significant difference in at least one relevant healing outcome comparison: AInorm vs. AIslow, AInorm vs. AInu, or NUhealed vs. NUslow. Differences were observed for various subsets of biomarkers within each time period, and in the magnitudes by which biomarker levels changed between time periods (FIGS. 9A-12B). In certain embodiments, the remaining 24 RNAs, other microarray RNAs not tested by RT-qPCR, and serum proteins recited in U.S. Provisional Patent Application Nos. 62/231,935 and 62/283,443 are further candidate biomarkers. In other embodiments, these are added to the diagnostic test panel to replace the primary biomarkers listed in this example.

RNA expression measurements were normalized by two methods. In the first approach, the average of all qPCR signals for all detected targets across all samples was determined, and each target's signal within a sample was multiplied by a scale factor that adjusted the sample's average to the global average. This method provides a robust normalization that is not sensitive to fluctuations in a reference gene, but requires a sufficiently large number of target measurements per sample and may be less effective for diagnostic testing of individual samples and a limited target panel. The second approach was normalization of long RNA signals to the endogenous reference gene TBP and of microRNA signals to the synthetic spike-in reference hsa-miR-450a-5p. This more traditional method of qPCR normalization can increase measurement noise due to fluctuations of the reference analyte and differences in qPCR amplification efficiency, but provides a within-sample normalization that can be applied each time an individual diagnostic test is performed. For the large majority of results described here, the two normalization methods produced similar data.

Two hundred twenty-eight RNAs showed blood expression differences among acute injury patients (FIGS. 9A-10Q). Seventy-six RNAs showed blood expression differences among diagnosed nonunion patients, (FIGS. 11A-12B), of which 71 were in common with the acute injury biomarkers.

The disclosures of each and every patent, patent application, and publication cited herein are hereby incorporated herein by reference in their entireties.

While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11339436B2). An electronic copy of the "Sequence Listing" will also be available from the USPTO upon request and payment of the fee set forth in 37 CFR 1.19(b)(3).

What is claimed is:

1. A method of promoting bone healing in a subject with a fractured bone, the method comprising
   providing a nonunion-mitigating intervention to the subject when a difference in the level, or a difference in change of the level, of a panel of RNA biomarkers in a subject's sample as compared to the level of the panel of RNA biomarkers in a reference sample is indicative of a nonunion or slow healing of the fractured bone in the subject, wherein the difference in level or the difference in change of level of the panel of RNA biomarkers is determined by:
   (a) comparing the level of a panel of RNA biomarkers in a sample from the subject to a baseline level of the panel of RNA biomarkers in a reference sample, wherein a difference in the level of the panel of RNA biomarkers in the subject's sample as compared to the level in the reference sample is indicative of a nonunion or slow healing of the fractured bone in the subject; or,
      comparing the change of the level of the panel of RNA biomarkers between samples collected from the subject at two or more different times to a baseline change of the level of the panel of RNA biomarkers in corresponding reference samples, wherein a difference in the amount of change of the level of the panel of RNA biomarkers in the subject's samples as compared to the level in the corresponding reference samples is indicative of a nonunion or slow healing of the fractured bone in the subject; and
   wherein the panel of RNA biomarkers is selected from the group consisting of:
   (i) a panel of RNA biomarkers comprising SEQ ID NOs: 1, 2, 3, 4, 5, 6, 7, 30, 31, 53, 64, 75, 78, 89, 104, 106, 109, 126, 132, 134, 189, 191, 194, 228, 233, 239, 270, 279, 283, 290, 291, 293, 299, 344, 347, 349, 371, 388, 400, 401, 408, 413, 442, 449, 453, 459, 471, 497, 512, 513, 515, 518, 519, 520, 521, 522, 523, 525, 527, 528, 529, 531, 533, 539, 540, 541, 543, 548, 549, 550, 551, 552, 554, 556, 618, 654, 677, 702, 1520, 1549 and 1838; and,
   (ii) a panel of RNA biomarkers comprising SEQ ID NOs: 9, 24, 45, 103, 124, 164, 219, 314, 351, 516, 517, 526, 534, 535, 542, 553, 562, 563, 572, 573, 582, 598, 599, 602, 609, 619, 620, 624, 625, 634, 652, 653, 655, 656, 676, 682, 698, 700, 701, 703, 721, 722, 723, 724, 725, 729, 753, 759, 760, 762, 764, 765, 766, 768, 769, 770, 771, 777, 781, 785, 789, 791, 794, 806, 814, 816, 824, 844, 850, 855, 862, 864, 867, 885, 889, 910, 911, 912, 914, 915, 917, 918, 931, 934, 938, 954, 958, 961, 962, 966, 968, 985, 996, 1004, 1024, 1027, 1030, 1032, 1035, 1051, 1054, 1063, 1066, 1068, 1069, 1070, 1071, 1073, 1074, 1075, 1080, 1086, 1087, 1096, 1100, 1109, 1110, 1111, 1114, 1115, 1126, 1141, 1151, 1153, 1154, 1180, 1201, 1216, 1228, 1244, 1245, 1277, 1279, 1281, 1283, 1286, 1288, 1293, 1318, 1337, 1363, 1382, 1405, 1406, 1431, 1437, 1489, 1493, 1499, 1500, 1501, 1502, 1506, 1508, 1512, 1513, 1514, 1515, 1516, 1517, 1522, 1523, 1524, 1526, 1527, 1528, 1529, 1531, 1532, 1533, 1534, 1535, 1536, 1539, 1541, 1542, 1543, 1544, 1546, 1547, 1548, 1551, 1552, 1554, 1555, 1561, 1562, 1565, 1568, 1575, 1576, 1579, 1582, 1584, 1585, 1597, 1598, 1599, 1600, 1601, 1605, 1607, 1608, 1609, 1610, 1626, 1627, 1628, 1637, 1640, 1643, 1645, 1648, 1649, 1652, 1654, 1656, 1657, 1662, 1665, 1677, 1830, 1831, 1832, 1833, 1834, 1835, 1836, and 1837.

2. The method of claim 1, further comprising determining the level of the panel of RNA biomarker molecules in a sample from the subject before performing step (a).

3. The method of claim 1, wherein the level, or change in the level, of the panel of RNA biomarkers is at least 1.1-fold higher or lower than the level, or change in the level, of the panel of RNA biomarkers in the reference sample.

4. The method of claim 1, wherein the bone healing does not occur or initiate for a period selected from the group consisting of: about 9 months or less after injury or after a nonunion-mitigating intervention, about 4 months or less after injury or after a nonunion-mitigating intervention, and about 2 weeks after injury or after a nonunion-mitigating intervention.

5. The method of claim 1, wherein the bone healing is assessed at one or more time periods, and wherein the assessment is done during or before the fourth month of healing.

6. The method of claim 1, wherein the nonunion-mitigating intervention comprises at least one treatment selected from the group consisting of:
   (a) an invasive surgical treatment comprising bone graft, removal of scar tissue, application of therapeutic drugs or biologics, or immobilization of the fracture with metal plates, rods or pins, and
   (b) a non-invasive treatment comprising electrical stimulation, ultrasound, treatment with therapeutic drugs or biologics, or immobilization of the fracture with specialized braces.

7. The method of claim 1, wherein the RNA in the panel of RNA biomarkers is at least one selected from the group consisting of a messenger RNA, a non-coding RNA, and a microRNA.

8. The method of claim 1, wherein when the level of the panel of RNA biomarkers in either (i) or (ii) is at least 1.1-fold higher or lower than the level of the corresponding RNA in the panel of RNA biomarkers in the reference sample, nonunion, slow healing or normal healing after acute injury is indicated, or successful, no or slow healing after a nonunion-mitigating intervention is indicated.

9. The method of claim 1, wherein a change of expression over time of the panel of RNA biomarkers in either (i) or (ii) indicates nonunion, slow healing or normal healing after acute injury, or indicates successful, no or slow healing after a nonunion-mitigating intervention.

10. The method of claim 9, wherein when the change in the level of expression over time of the panel of RNA biomarkers over time is at least 1.1-fold higher or lower than the change in the level of expression over time of the corresponding panel of RNA biomarkers in the reference sample, then nonunion, slow healing or normal healing after acute injury is indicated, or successful, no or slow healing after a nonunion-mitigating intervention is indicated.

11. The method of claim 1, wherein the panel of RNA biomarkers comprises a panel of mRNA or ncRNA biomarkers.

12. The method of claim 1, wherein the panel of RNA biomarkers comprises a panel of miRNA biomarkers.

13. The method of claim 1, wherein at least one of the following applies:
   (a) the subject is a mammal;
   (b) the subject is a human;
   (c) determining the level of the panel of RNA biomarkers comprises at least one technique selected from the group consisting of reverse transcription, PCR, microarray, next generation sequencing, nuclease protection, probe hybridization, pyrosequencing, and primer extension;
   (d) the subject's sample is at least one selected from the group consisting of blood, peripheral blood, serum, plasma, urine, stool samples, saliva, biological fluid gathered from an anatomic area in proximity to the fractured bone, biological fluid from fractured bone, primary cells, and cultured cells;
   (e) the comparison of the level of RNA expression is computed using at least one statistical method selected from the group consisting of pairwise and multi-class ANOVA tests, t-tests, chi-square tests, Bayesian tests, machine learning algorithms, and Extraction of Differential Gene Expression (EDGE) tool analysis;
   (f) the ratios, sums, products or other mathematical combinations of expression level of at least two RNAs as compared to the corresponding expression levels in reference samples are used to calculate a score or composite score that characterizes the bone healing in the subject.

* * * * *